(12) United States Patent
Konno et al.

(10) Patent No.: US 11,219,417 B2
(45) Date of Patent: Jan. 11, 2022

(54) TOMOSYNTHESIS IMAGING APPARATUS

(71) Applicant: FUJIFILM Corporation, Tokyo (JP)

(72) Inventors: Shinichiro Konno, Kanagawa (JP); Takeyasu Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/988,860

(22) Filed: Aug. 10, 2020

(65) Prior Publication Data

US 2021/0068770 A1 Mar. 11, 2021

(51) Int. Cl.
*A61B 6/03* (2006.01)
*A61B 6/02* (2006.01)
*A61B 6/00* (2006.01)
*A61B 6/04* (2006.01)
*A61B 6/06* (2006.01)

(52) U.S. Cl.
CPC ............ *A61B 6/025* (2013.01); *A61B 6/0492* (2013.01); *A61B 6/06* (2013.01); *A61B 6/4007* (2013.01); *A61B 6/0414* (2013.01); *A61B 6/502* (2013.01)

(58) Field of Classification Search
CPC ..... A61B 6/035; A61B 6/4007; A61B 6/4435; A61B 6/025; A61B 6/0414; A61B 6/502; A61B 6/06; A61B 6/08; A61B 6/032; A61N 5/1081; A61N 5/1084; A61N 2005/1061
See application file for complete search history.

(56) References Cited

U.S. PATENT DOCUMENTS

2016/0310086 A1* 10/2016 Besson ................ A61B 6/5205

FOREIGN PATENT DOCUMENTS

JP 2014-087697 A 5/2014

* cited by examiner

*Primary Examiner* — Don K Wong
(74) *Attorney, Agent, or Firm* — Studebaker & Brackett PC

(57) ABSTRACT

Fifteen radiation tubes are arranged in a radiation source of the mammography apparatus. An irradiation field limiter has a plurality of first irradiation opening portions which are provided in an X direction and each of which is configured by a pair of a first opening and a second opening facing each other in an irradiation direction of radiation and defines an irradiation field of the radiation. The irradiation field limiter includes a first rotating member that is rotated to a first rotation position and a second rotation position about a rotating shaft parallel to the X direction. At the first rotation position and the second rotation position, the first irradiation opening portions which are arranged at an interval of one radiation tube face the radiation tubes in the irradiation direction. The first irradiation opening portions deviate from each other in the X direction. Among 15 radiation tubes, at least some of second radiation tubes, which are other than first radiation tubes facing the first irradiation opening portions at the first rotation position and do not face the first irradiation opening portions, face the first irradiation opening portions at the second rotation position.

12 Claims, 47 Drawing Sheets

FIG. 10
(A)
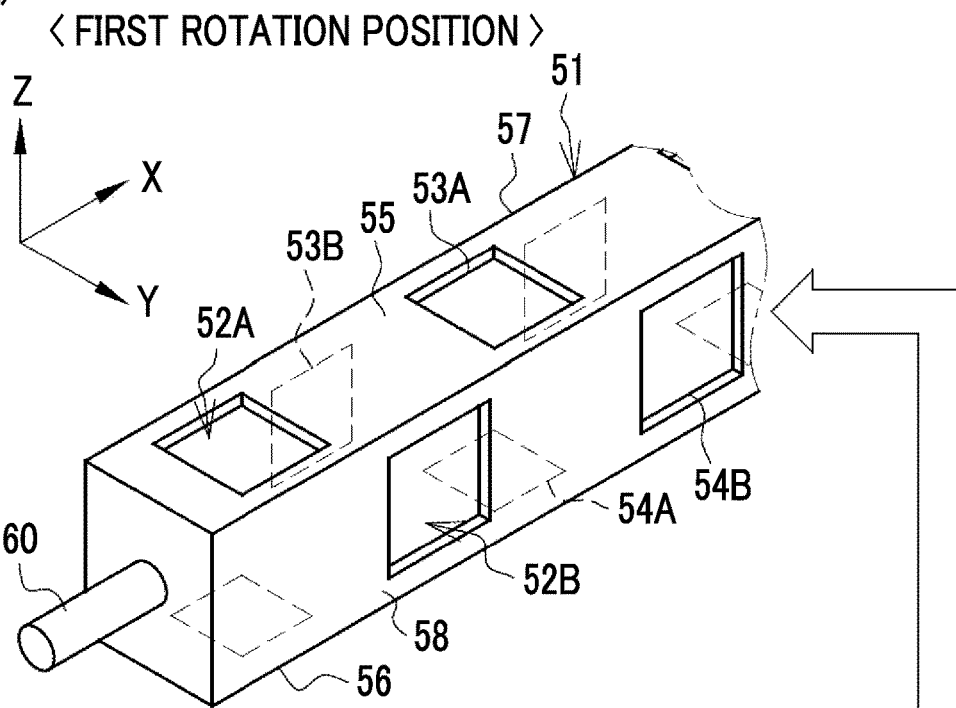
(B)
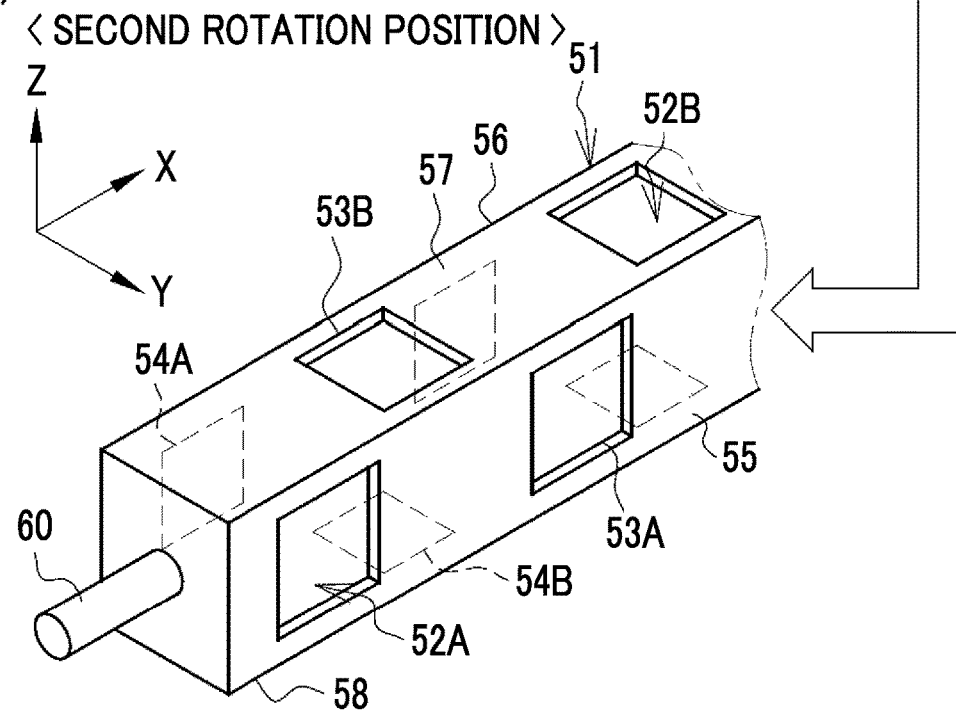

FIG. 13
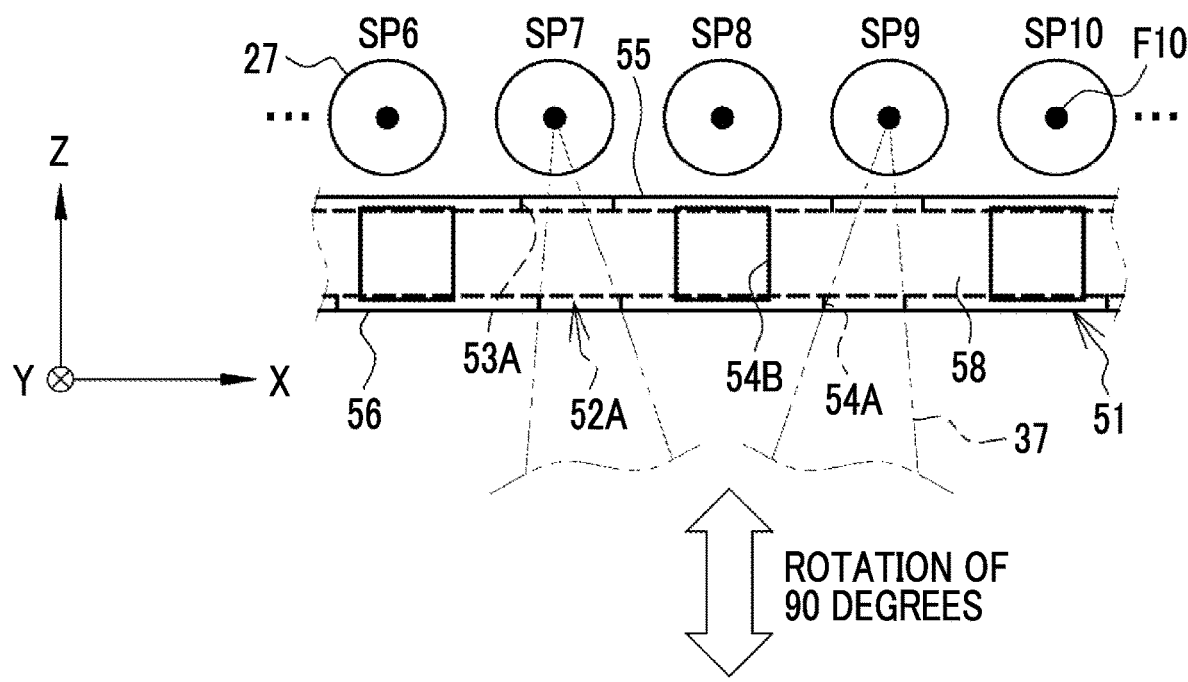
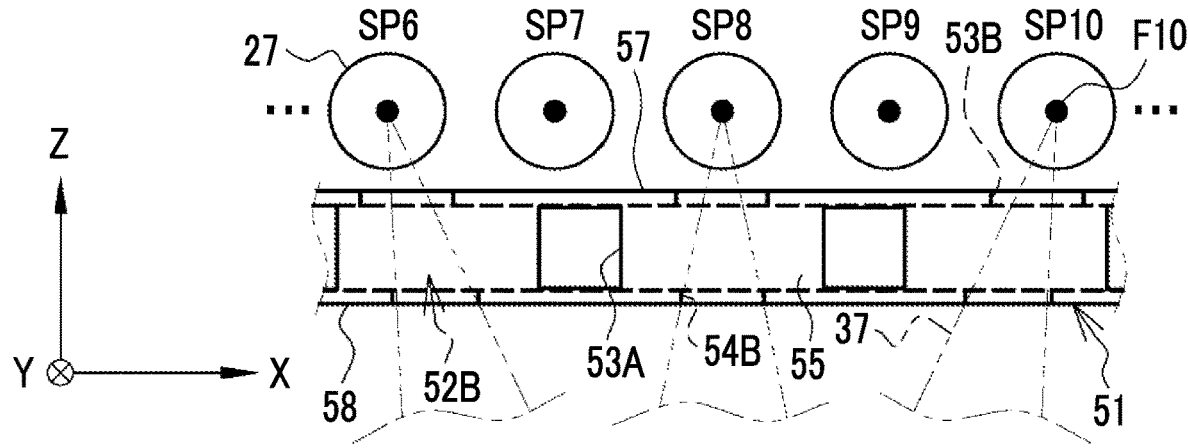

FIG. 17

| COMPRESSION PLATE USED | IMAGING MODE | RADIATION TUBE USED |
|---|---|---|
| COMPRESSION PLATE A | IMAGE QUALITY PRIORITY MODE | RT01 TO RT15 (SP1 TO SP15) |
| COMPRESSION PLATE A | EXPOSURE REDUCTION MODE | RT01, RT03, RT04, RT06, RT08, RT10, RT12, RT13, RT15 (SP1, SP3, SP4, SP6, SP8, SP10, SP12, SP13, SP15) |
| COMPRESSION PLATE B | IMAGE QUALITY PRIORITY MODE | RT02 TO RT14 (SP2 TO SP14) |
| COMPRESSION PLATE B | EXPOSURE REDUCTION MODE | RT02, RT04, RT06, RT08, RT10, RT12, RT14 (SP2, SP4, SP6, SP8, SP10, SP12, SP14) |
| ... | | |

SETTING TABLE

FIG. 18

| OPERATING CONDITIONS | | | 88 |
|---|---|---|---|
| IRRADIATION NUMBER | RADIATION TUBE | ROTATION POSITION | |
| 1 | RT03 (SP3) | FIRST ROTATION POSITION | |
| 2 | RT05 (SP5) | FIRST ROTATION POSITION | |
| 3 | RT07 (SP7) | FIRST ROTATION POSITION | |
| 4 | RT09 (SP9) | FIRST ROTATION POSITION | |
| 5 | RT11 (SP11) | FIRST ROTATION POSITION | |
| 6 | RT13 (SP13) | FIRST ROTATION POSITION | |
| 7 | RT02 (SP2) | SECOND ROTATION POSITION | ROTATION OF 90 DEGREES |
| 8 | RT04 (SP4) | SECOND ROTATION POSITION | |
| 9 | RT06 (SP6) | SECOND ROTATION POSITION | |
| 10 | RT08 (SP8) | SECOND ROTATION POSITION | |
| 11 | RT10 (SP10) | SECOND ROTATION POSITION | |
| 12 | RT12 (SP12) | SECOND ROTATION POSITION | |
| 13 | RT14 (SP14) | SECOND ROTATION POSITION | |

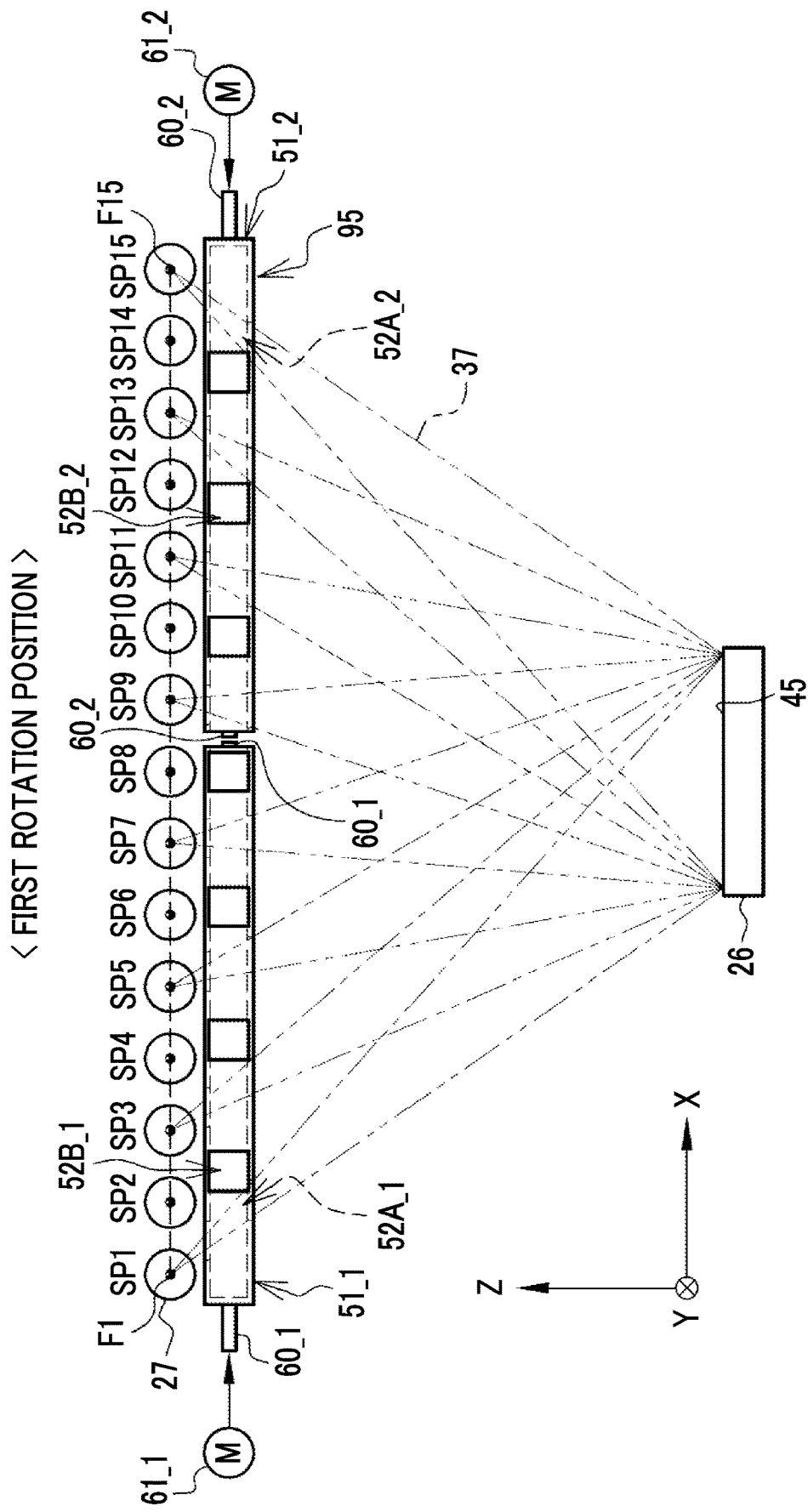

FIG. 22

| FIRST ROTATING MEMBER (LEFT) | FIRST ROTATING MEMBER (RIGHT) |
|---|---|
| EMISSION OF RADIATION AT FIRST ROTATION POSITION | WAITING AT FIRST ROTATION POSITION |
| ROTATION TO SECOND ROTATION POSITION AND WAITING | EMISSION OF RADIATION AT FIRST ROTATION POSITION |
| EMISSION OF RADIATION AT SECOND ROTATION POSITION | ROTATION TO SECOND ROTATION POSITION AND WAITING |
|  | EMISSION OF RADIATION AT SECOND ROTATION POSITION |

98

FIG. 27
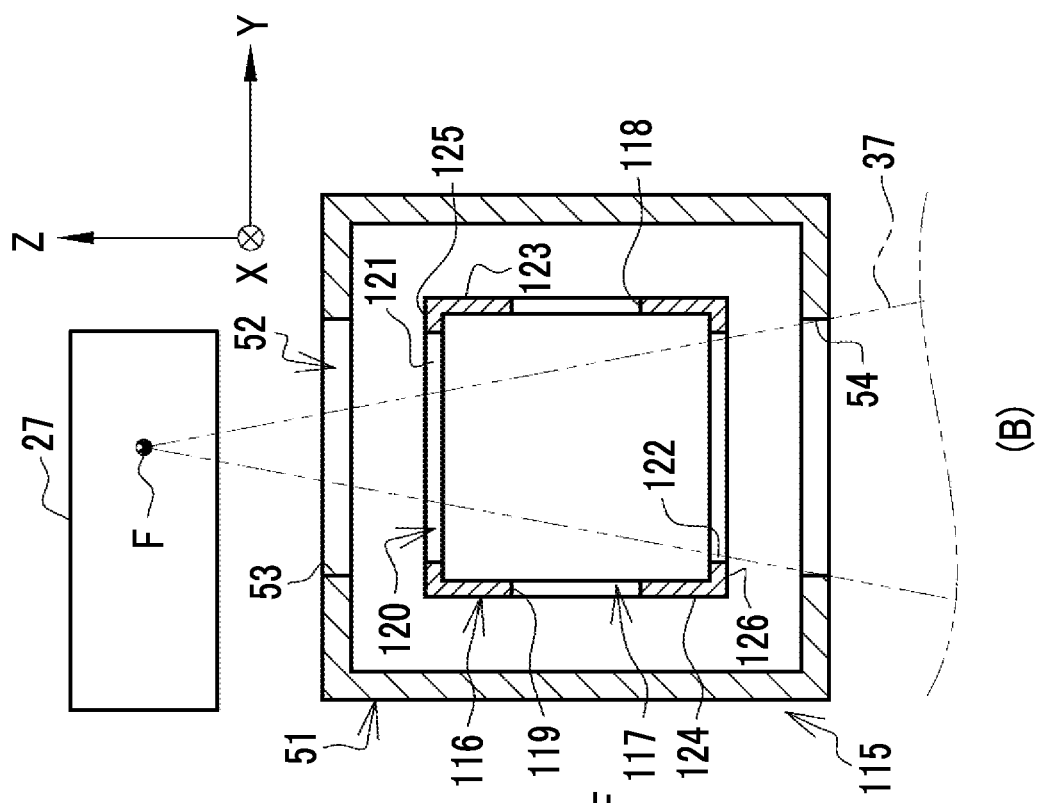
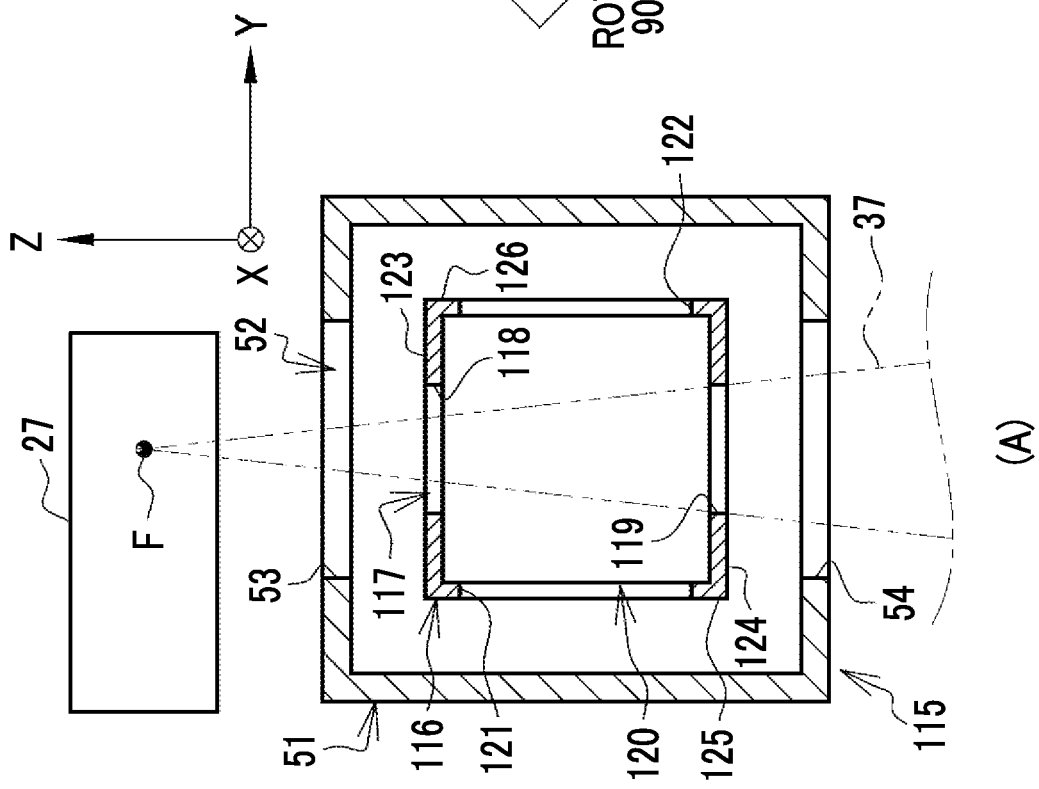

FIG. 30
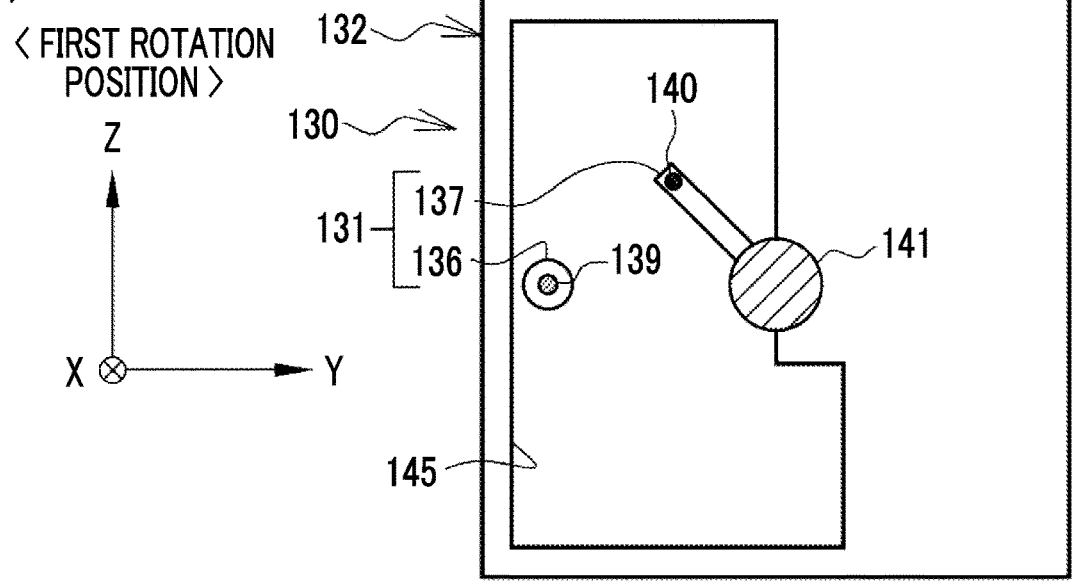
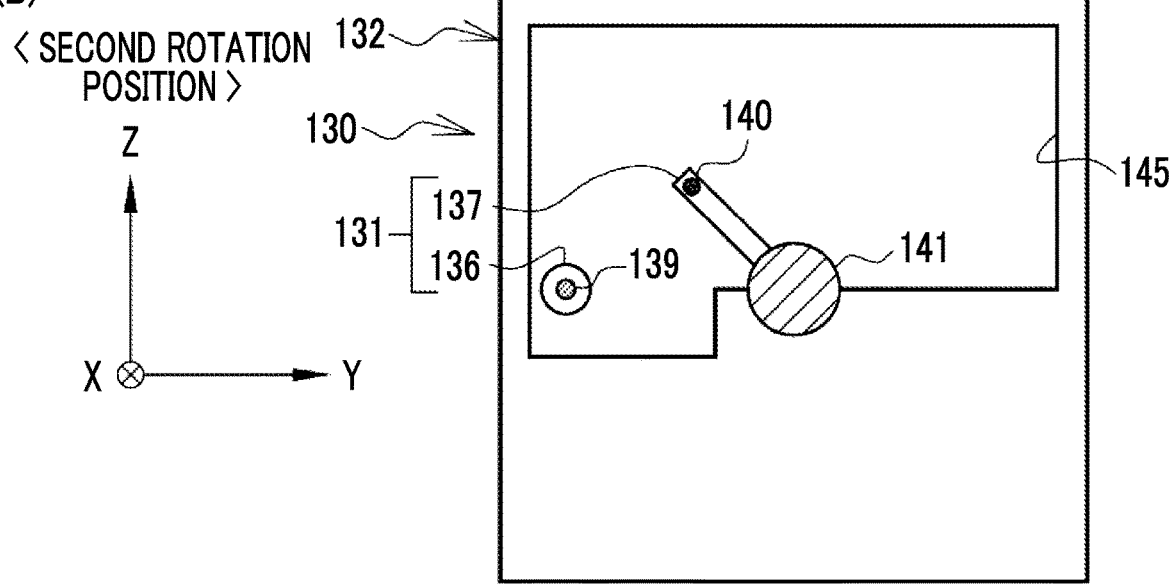

FIG. 35

| ROTATION POSITION | RADIATION TUBE |
|---|---|
| FIRST ROTATION POSITION | RT01, RT04, RT07, RT10, RT13 (SP1, SP4, SP7, SP10, SP13) |
| SECOND ROTATION POSITION | RT02, RT05, RT08, RT11, RT14 (SP2, SP5, SP8, SP11, SP14) |
| THIRD ROTATION POSITION | RT03, RT06, RT09, RT12, RT15 (SP3, SP6, SP9, SP12, SP15) |

168

- - → FIRST RADIATION TUBE
- - → SECOND RADIATION TUBE
- - → THIRD RADIATION TUBE

FIG. 38

| ROTATION POSITION | RADIATION TUBE |
|---|---|
| FIRST ROTATION POSITION | RT01, RT05, RT09, RT13 (SP1, SP5, SP9, SP13) |
| SECOND ROTATION POSITION | RT02, RT06, RT10, RT14 (SP2, SP6, SP10, SP14) |
| THIRD ROTATION POSITION | RT03, RT07, RT11, RT15 (SP3, SP7, SP11, SP15) |
| FOURTH ROTATION POSITION | RT04, RT08, RT12 (SP4, SP8, SP12) |

178

← FIRST RADIATION TUBE
← SECOND RADIATION TUBE
← THIRD RADIATION TUBE
← FOURTH RADIATION TUBE

FIG. 41

| ROTATION POSITION | RADIATION TUBE | |
|---|---|---|
| First Rotation Position | RT01, RT06, RT11 (SP1, SP6, SP11) | ← FIRST RADIATION TUBE |
| Second Rotation Position | RT02, RT07, RT12 (SP2, SP7, SP12) | ← SECOND RADIATION TUBE |
| Third Rotation Position | RT03, RT08, RT13 (SP3, SP8, SP13) | ← THIRD RADIATION TUBE |
| Fourth Rotation Position | RT04, RT09, RT14 (SP4, SP9, SP14) | ← FOURTH RADIATION TUBE |
| Fifth Rotation Position | RT05, RT10, RT15 (SP5, SP10, SP15) | ← FIFTH RADIATION TUBE |

188

FIG. 46
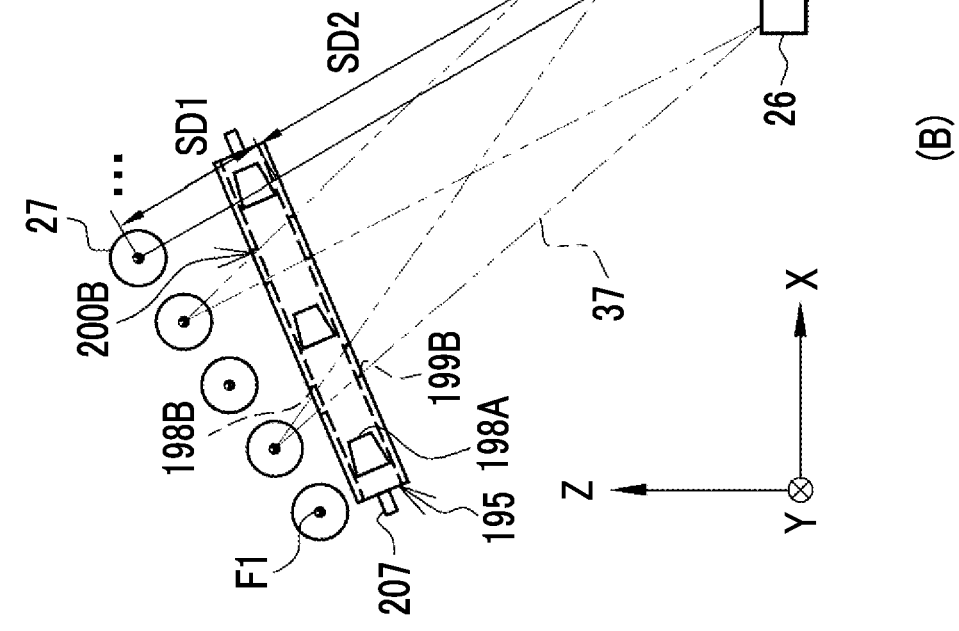
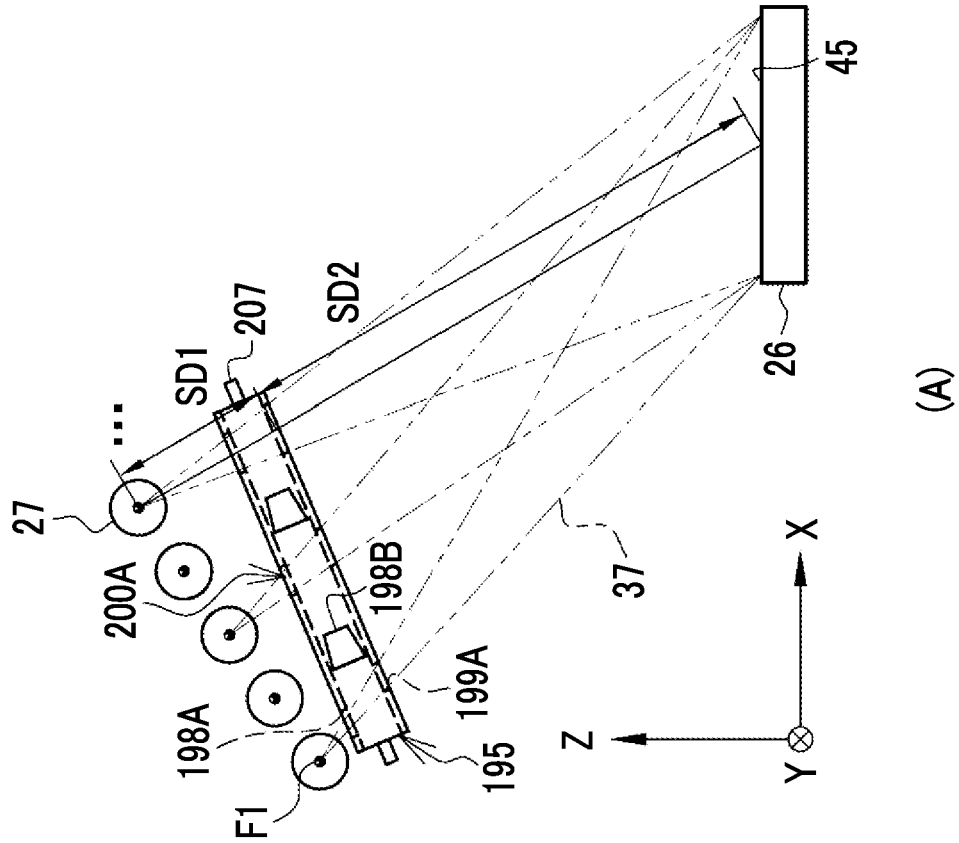

TOMOSYNTHESIS IMAGING APPARATUS

CROSS-REFERENCE TO RELATED APPLICATIONS

The present application claims priority under 35 U.S.C. § 119 to Japanese Patent Application No. 2019-162950 filed on Sep. 6, 2019. The above application is hereby expressly incorporated by reference, in its entirety, into the present application.

BACKGROUND

1. Technical Field

The technology of the present disclosure relates to a tomosynthesis imaging apparatus.

2. Description of the Related Art

Tomosynthesis imaging has been known which irradiates an object with radiation at a plurality of different irradiation angles in order to generate a tomographic image in any tomographic plane of the object. JP2014-087697A discloses a tomosynthesis imaging apparatus that performs tomosynthesis imaging using a radiation source in which a plurality of focuses where radiation is emitted are arranged. The tomosynthesis imaging apparatus disclosed in JP2014-087697A has an irradiation field limiter in which irradiation openings for radiation which define the irradiation field of radiation are formed so as to correspond to each of a plurality of focuses.

SUMMARY

The inventors have studied a technique in which three or more radiation tubes, each of which has one or more focuses, are used and adjacent radiation tubes are brought close to each other to improve the signal-noise (SN) ratio of a tomographic image. In this configuration, in a case in which an irradiation field limiter having irradiation openings formed so as to correspond to each of a plurality of radiation tubes is applied and radiation is emitted from a certain radiation tube, the radiation leaks from the irradiation openings corresponding to adjacent radiation tubes, which may cause unnecessary exposure.

An object of the technology of the present disclosure is to provide a tomosynthesis imaging apparatus that can prevent unnecessary exposure.

In order to achieve the above object, according to the present disclosure, there is provided a tomosynthesis imaging apparatus comprising: a radiation source in which three or more radiation tubes emitting radiation are arranged to perform tomosynthesis imaging which irradiates an object with the radiation at a plurality of different irradiation angles; and an irradiation field limiter having a plurality of first irradiation opening portions which are provided along a direction of a straight line connecting focuses of the radiation tubes at both ends where the radiation is emitted and each of which is configured by a pair of a first opening and a second opening facing each other in an irradiation direction of the radiation and defines an irradiation field of the radiation. The irradiation field limiter includes a first rotating member that is rotated to a plurality of rotation positions including at least a first rotation position and a second rotation position about a rotating shaft that is parallel to the direction of the straight line. At the rotation positions, two or more of the first irradiation opening portions which are arranged at an interval of at least one radiation tube face the radiation tubes in the irradiation direction. The first irradiation opening portions deviate from each other in the direction of the straight line. Among the three or more radiation tubes, at least some of second radiation tubes, which are other than first radiation tubes facing the first irradiation opening portions at the first rotation position and do not face the first irradiation opening portions, face the first irradiation opening portions at the second rotation position.

Preferably, the irradiation field is defined by the first opening or the second opening.

Preferably, a plurality of the first rotating members are arranged along the direction of the straight line and are independently rotated.

Preferably, the first rotating member has a regular N-gonal shape in a cross-sectional view taken along a lateral direction, and N is an even number that is equal to or greater than 4. In this case, preferably, the rotation positions are positions corresponding to 360°/N.

Preferably, the first rotating member has a circular shape in a cross-sectional view taken along a lateral direction.

Preferably, the first opening and the second opening have different sizes.

Preferably, the first rotating member is hollow.

Preferably, the irradiation field limiter has a configuration in which a second rotating member that is rotated about a rotating shaft parallel to the direction of the straight line independently of the first rotating member and has a second irradiation opening portion with a size different from that of the first irradiation opening portion is provided in the first rotating member.

Preferably, the irradiation field limiter has a configuration in which a visible light emitting unit that emits visible light indicating the irradiation field is provided in the first rotating member.

Preferably, the rotating shaft of the first rotating member is offset from centers of the first and second openings in a plan view from the direction of the straight line.

Preferably, the plurality of radiation tubes are arranged at equal intervals in a linear shape or an arc shape.

According to the technique of the present disclosure, it is possible to provide a tomosynthesis imaging apparatus that can prevent unnecessary exposure.

BRIEF DESCRIPTION OF THE DRAWINGS

Exemplary embodiments according to the technique of the present disclosure will be described in detail based on the following figures, wherein:

FIG. 10 is a diagram illustrating a first rotating member at each rotation position. (A) of FIG. 10 illustrates a first rotation position and (B) of FIG. 10 illustrates a second rotation position;

FIG. 13 is a diagram summarizing content illustrated in FIG. 11 and FIG. 12. (A) of FIG. 13 illustrates a main portion in the case of the first rotation position illustrated in FIG. 11 and (B) of FIG. 13 illustrates a main portion in the case of the second rotation position illustrated in FIG. 12;

FIG. 17 is a diagram illustrating a setting table;

FIG. 18 is a diagram illustrating operating conditions;

FIG. 21 is a diagram illustrating an example in which two first rotating members are used;

FIG. 22 is a table illustrating an operation procedure in the case of FIG. 21;

FIG. 27 is a diagram illustrating the second rotating member at each rotation position. (A) of FIG. 27 illustrates the first rotation position and (B) of FIG. 27 illustrates the second rotation position;

FIG. 30 is a plan view illustrating the first rotating member as viewed from the X direction. (A) of FIG. 30 illustrates a case in which the first rotating member is disposed at the first rotation position and (B) of FIG. 30 illustrates a case in which the first rotating member is disposed at the second rotation position;

FIG. 35 is a table illustrating the radiation tube IDs of the radiation tubes that emit radiation at each rotation position;

FIG. 38 is a table illustrating the radiation tube IDs of radiation tubes that emit radiation at each rotation position;

FIG. 41 is a table illustrating the radiation tube IDs of the radiation tubes that emit radiation at each rotation position;

FIGS. 46A and 46B are diagrams illustrating another example of the sizes and shapes of the first opening and the second opening of the first rotating member in the first group. FIG. 46A illustrates a first rotation position and FIG. 46B illustrates a second rotation position;

DETAILED DESCRIPTION

First Embodiment

Figure 1:
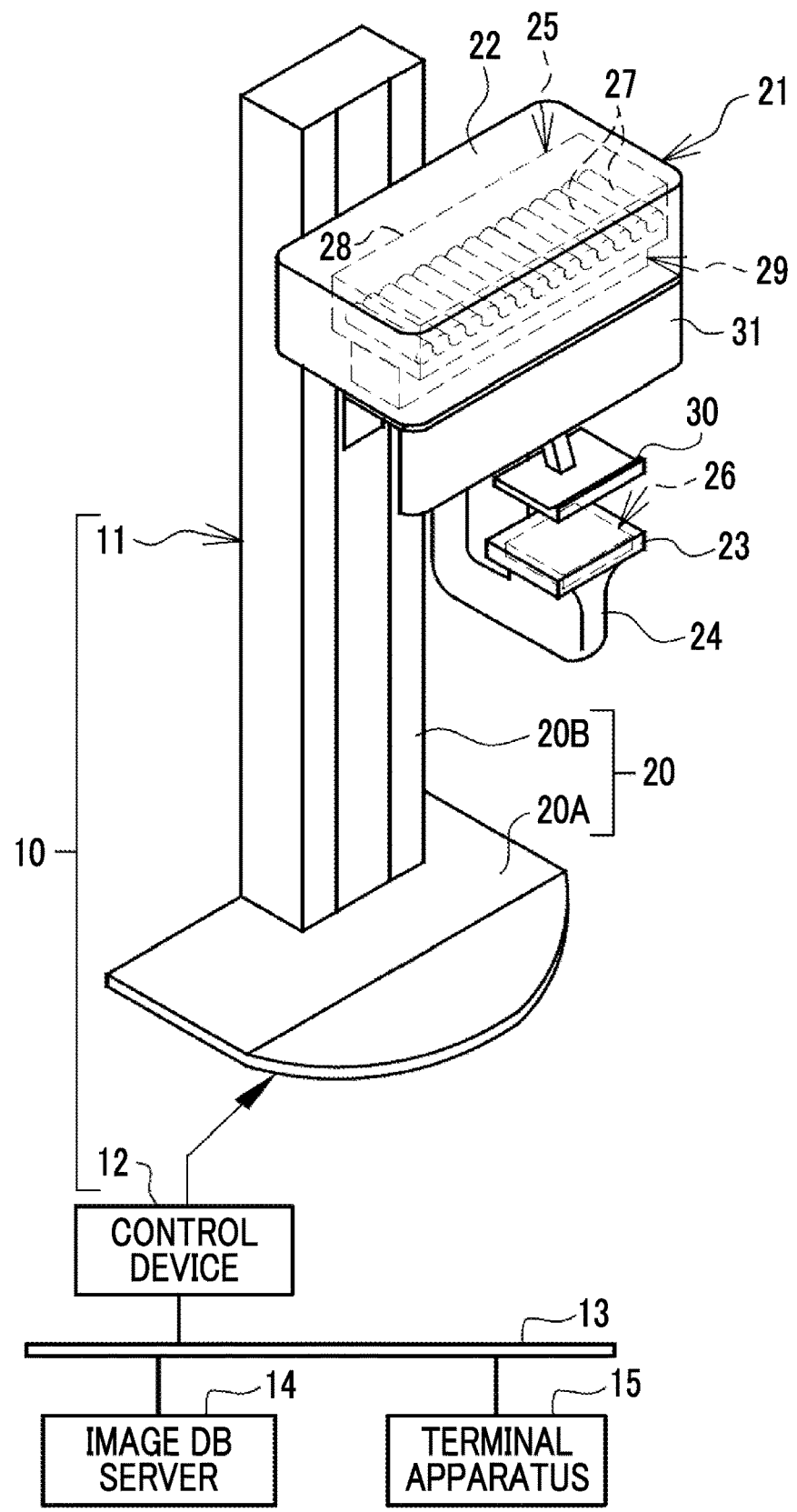
FIG. 1 is a diagram illustrating, for example, a mammography apparatus.
Figure 2:
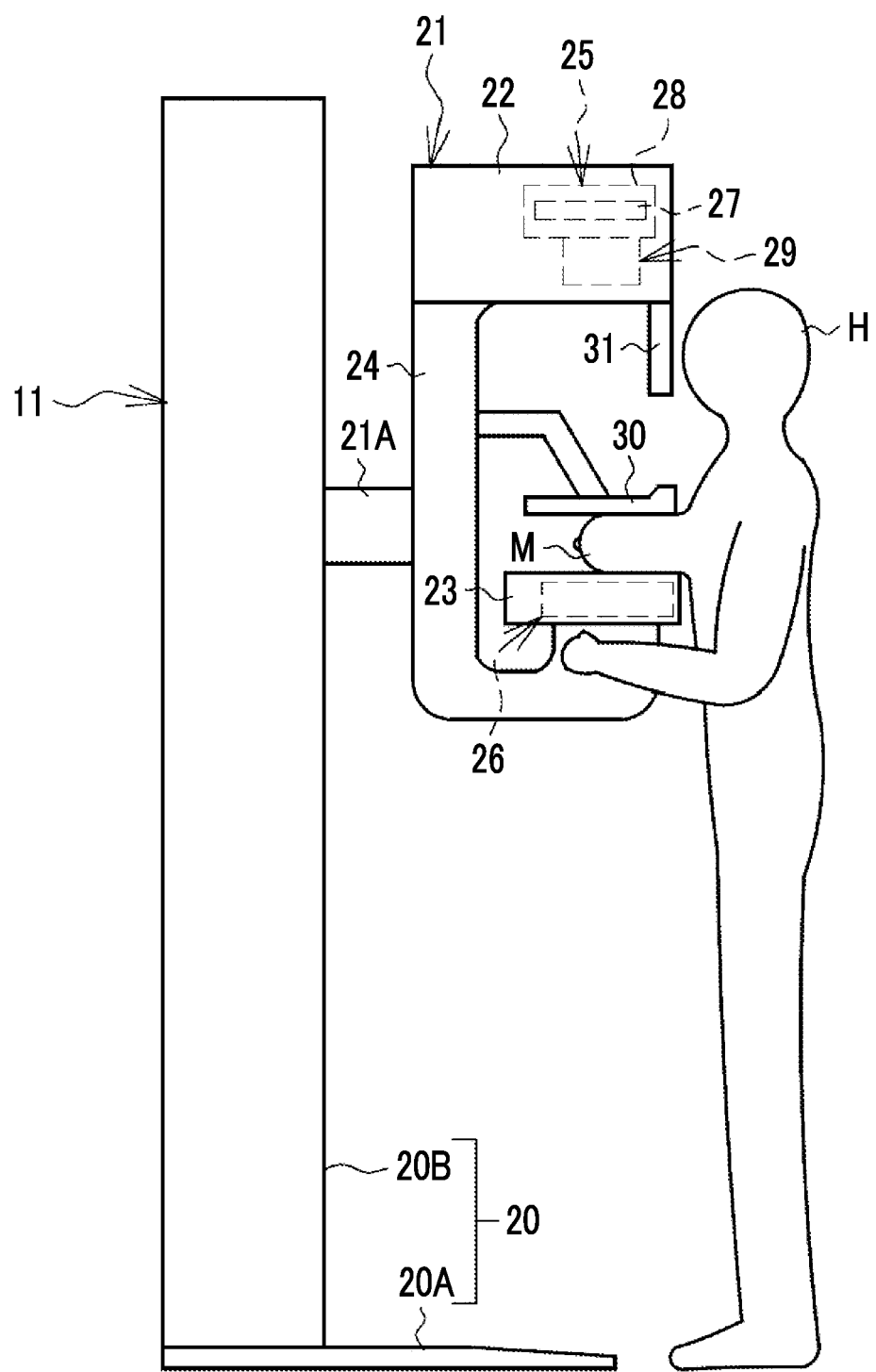
FIG. 2 is a diagram illustrating an apparatus main body of the mammography apparatus.

In FIGS. 1 and 2, a mammography apparatus 10 is an example of a "tomosynthesis imaging apparatus" according to the technique of the present disclosure and a breast M of a subject H is an object. The mammography apparatus 10 irradiates the breast M with radiation 37 (see, for example, FIG. 3), such as X-rays or y-rays, to capture a radiographic image of the breast M.

The mammography apparatus 10 includes an apparatus main body 11 and a control device 12. The apparatus main body 11 is installed, for example, in a radiography room of a medical facility. The control device 12 is installed, for example, in a control room next to the radiography room. The control device 12 is, for example, a desktop personal computer. The control device 12 is connected to an image database (hereinafter, referred to as a DB) server 14 through a network 13, such as a local area network (LAN), such that it can communicate with the image DB server 14. The image DB server 14 is, for example, a picture archiving and communication system (PACS) server, receives a radiographic image from the mammography apparatus 10, stores the radiographic image, and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotating shaft perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes a plurality of radiation tubes 27, for example, 15 radiation tubes 27 and a housing 28 that accommodates the radiation tubes 27. The housing 28 is filled with insulating oil. The radiation tubes 27 are used for tomosynthesis imaging which captures a plurality of projection images P (see FIG. 7) of the breast M at different irradiation angles as radiographic images. The radiation detector 26 detects the radiation 37 transmitted through the breast M and outputs a radiographic image. In addition, the number of radiation tubes 27 is not limited to 15 in the above example. The number of radiation tubes 27 may be three or more.

The radiation source accommodation portion 22 accommodates an irradiation field limiter 29 in addition to the radiation source 25. The irradiation field limiter 29 is attached to a lower part of the radiation source 25. The irradiation field limiter 29 is also called a collimator and defines the irradiation field of the radiation 37 in an imaging surface 45 (see FIG. 4) of the radiation detector 26.

A compression plate 30 is attached between the radiation source accommodation portion 22 and the detector accommodation portion 23 in the main body portion 24. The compression plate 30 is made of a material that transmits the radiation 37. The compression plate 30 is disposed so as to face the detector accommodation portion 23. The compression plate 30 can be moved in a direction toward the detector accommodation portion 23 and a direction away from the detector accommodation portion 23. The compression plate 30 is moved toward the detector accommodation portion 23 and compresses the breast M interposed between the detector accommodation portion 23 and the compression plate 30. There are a plurality of types of compression plates 30 which are interchanged according to, for example, the size of the breast M.

A face guard 31 is attached to a lower part of the front surface of the radiation source accommodation portion 22. The face guard 31 protects the face of the subject H from the radiation 37.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
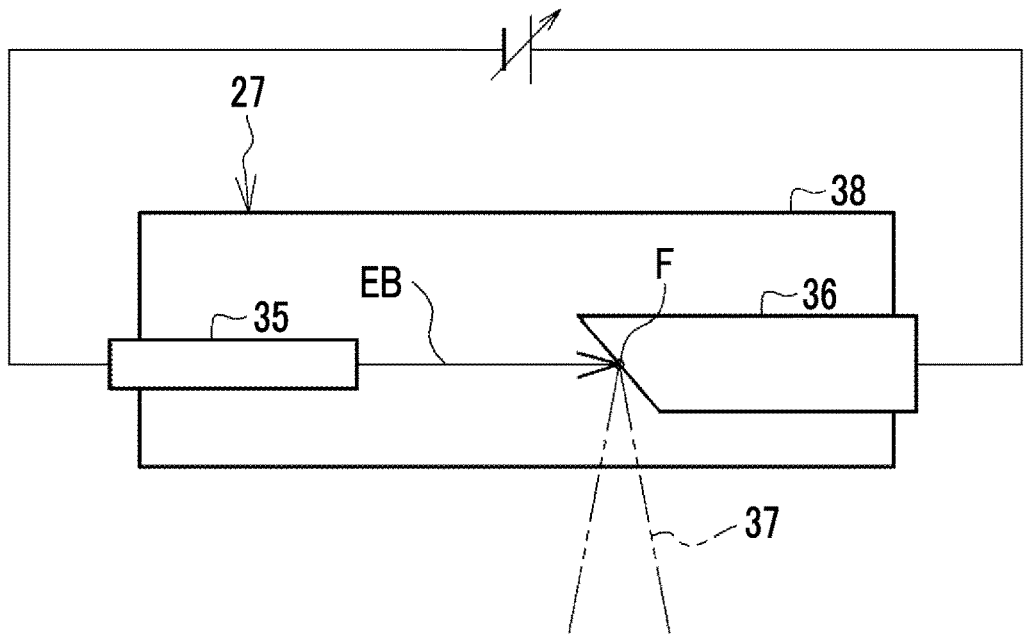
FIG. 3 is a diagram illustrating a radiation tube.

In FIG. 3, the radiation tube 27 includes a cathode 35 and an anode 36. The cathode 35 emits electrons. The electrons collide with the anode 36 and the anode 36 emits the radiation 37. The cathode 35 and the anode 36 are accommodated in a vacuum glass tube 38 with a substantially cylindrical shape. The cathode 35 is a cold cathode. Specifically, the cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides.

Figure 4:
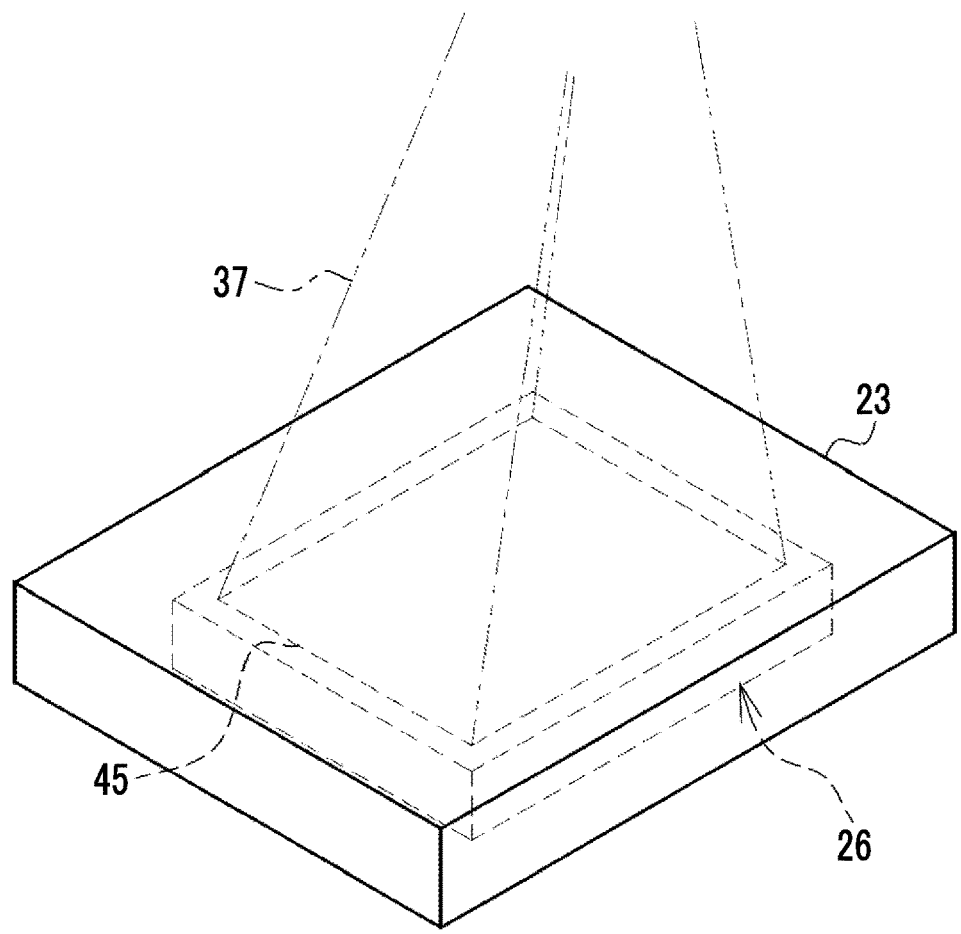
FIG. 4 is a diagram illustrating a detector accommodation portion.

In FIG. 4 illustrating the detector accommodation portion 23, the radiation detector 26 has the imaging surface 45. The imaging surface 45 detects the radiation 37 transmitted through the breast M and captures the projection image P of the breast M. Specifically, the imaging surface 45 is a two-dimensional plane in which pixels converting the radiation 37 into an electric signal are two-dimensionally arranged. The radiation detector 26 is called a flat panel detector (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal.

Figure 5:
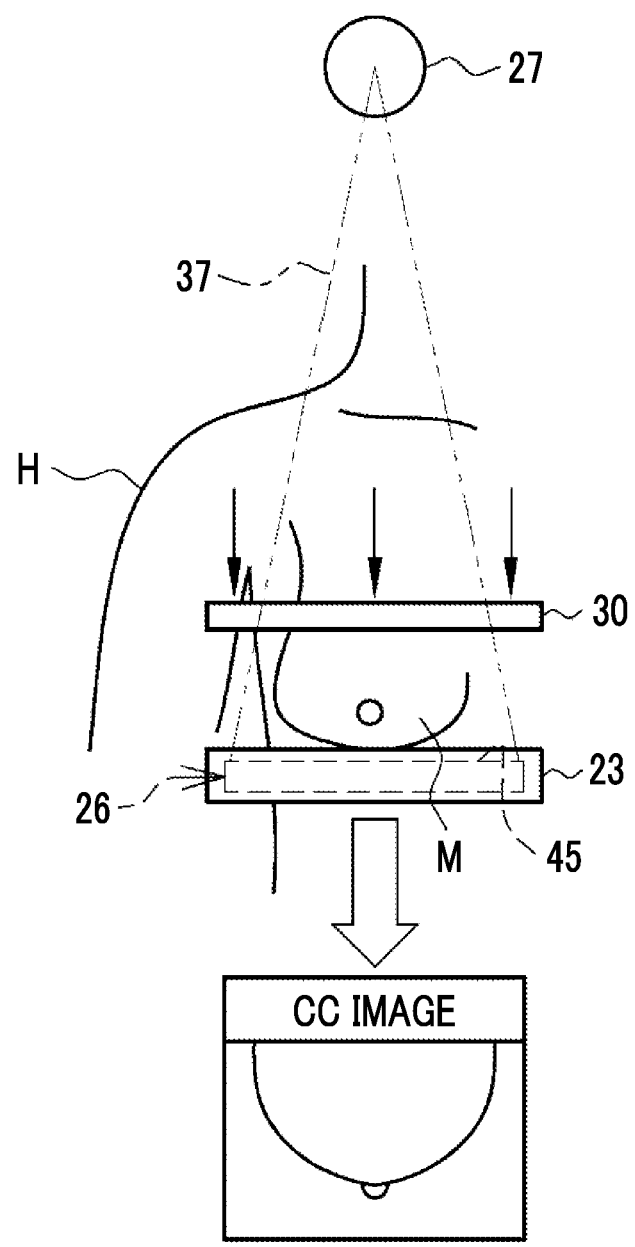
FIG. 5 is a diagram illustrating an aspect of CC imaging.
Figure 6:
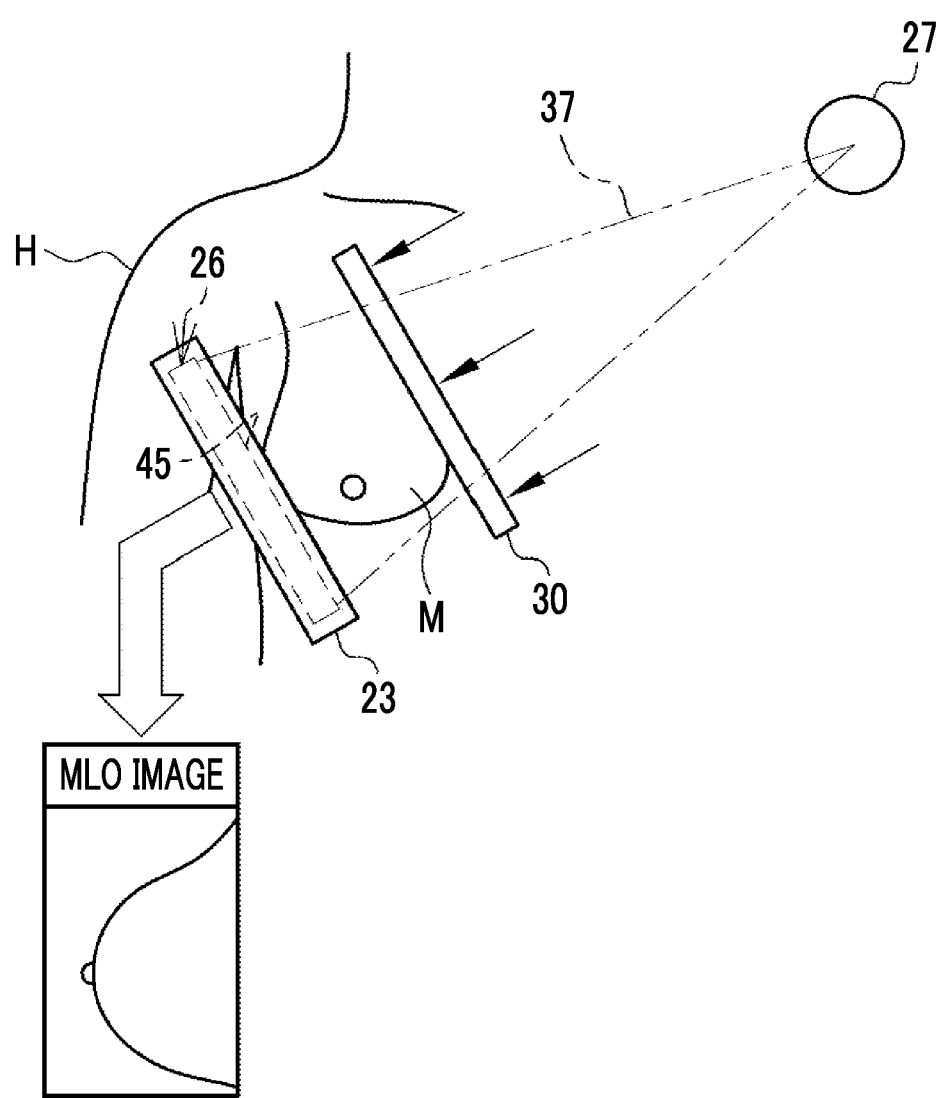
FIG. 6 is a diagram illustrating an aspect of MLO imaging.

FIGS. 5 and 6 illustrate a method for capturing an image of the breast M in the mammography apparatus 10. FIG. 5 illustrates craniocaudal view (CC) imaging and FIG. 6 illustrates mediolateral oblique view (MLO) imaging. The CC imaging is an imaging method which captures an image while compressing the breast M interposed between the detector accommodation portion 23 and the compression plate 30 in the vertical direction. In this case, the radiation detector 26 outputs a CC image as the projection image P. In contrast, the MLO imaging is an imaging method which captures an image while compressing the breast M interposed between the detector accommodation portion 23 and the compression plate 30 at an inclination angle of about 60°. In this case, the radiation detector 26 outputs an MLO image as the projection image P. In addition, FIGS. 5 and 6 illustrate only one radiation tube 27 for simplicity of illustration. Further, FIGS. 5 and 6 illustrate the right breast M. However, an image of the left breast M may be captured.

Figure 7:
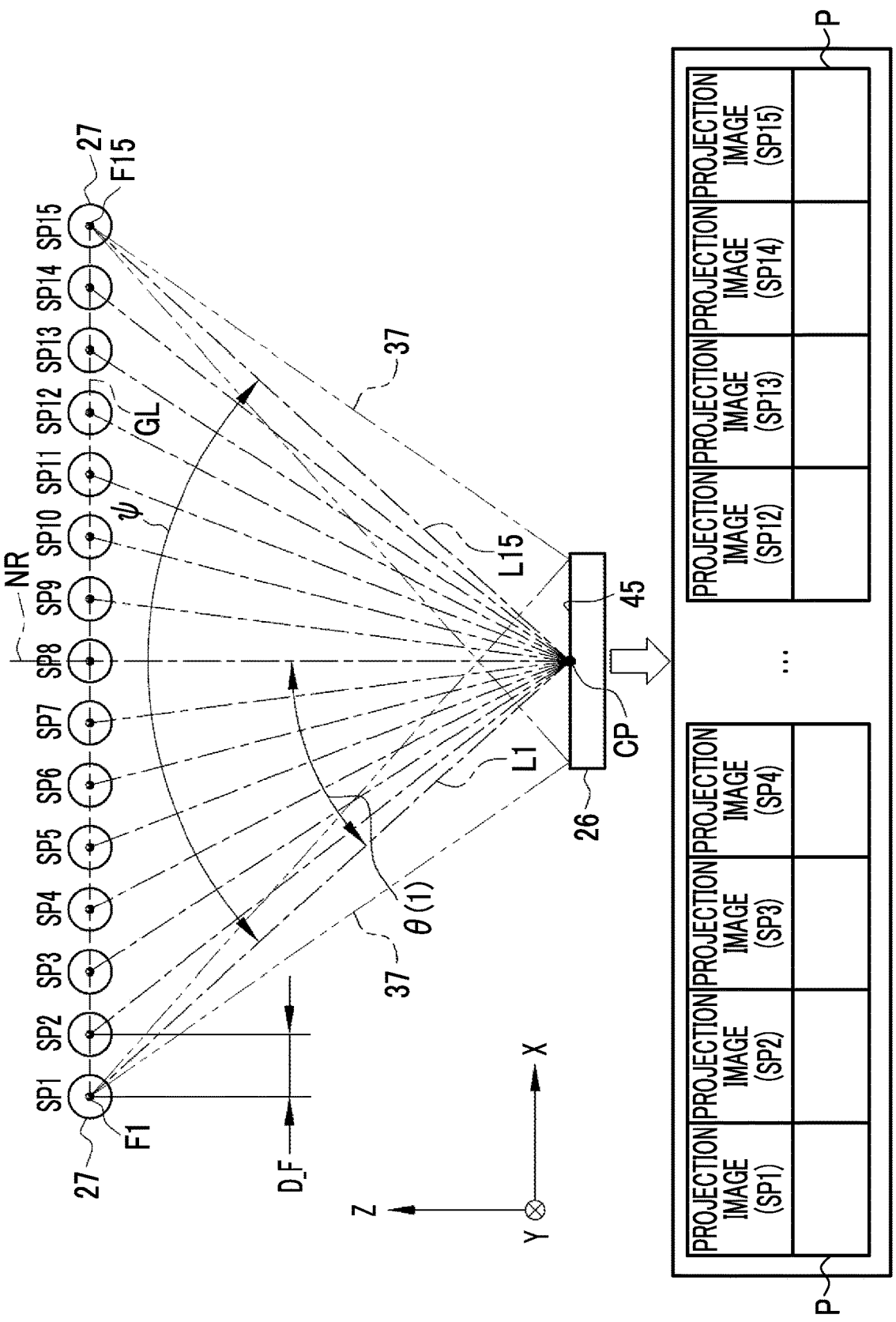
FIG. 7 is a diagram illustrating an aspect of tomosynthesis imaging.

In FIG. 7 which is a plan view illustrating the radiation source 25 and the radiation detector 26 as viewed from the support 20B, it is assumed that the direction of a normal line to the imaging surface 45 is the Z direction, a direction along a side of the imaging surface 45 is the X direction, and a depth direction of the imaging surface 45 which is perpendicular to the Z direction and the X direction is the Y direction. The radiation tubes 27 are provided at a total of 15 positions SP1, SP2, . . . , SP14, and SP15 where the radiation 37 is emitted to the imaging surface 45 at different irradiation angles. The focuses F1 to F15 of the radiation 37 in the radiation tubes 27 at the positions SP1 to SP15 are arranged in a linear shape at equal intervals D_F.

Further, the position SP8 is disposed on a normal line NR to the imaging surface 45 which extends from a center point CP of the side of the imaging surface 45 in the X direction. Positions other than the position SP8 are set so as to be bilaterally symmetric with respect to the normal line NR such that the positions SP1 to SP7 are disposed on the left side of the normal line NR and the positions SP9 to SP15 are disposed on the right side of the normal line NR. That is, the radiation tubes 27 at the positions SP1 to SP7 and the radiation tubes 27 at the positions SP9 to SP15 are disposed at positions that are symmetric with respect to a line.

Here, the focus F1 of the radiation tube 27 at the position SP1 and the focus F15 of the radiation tube 27 at the position SP15 are an example of "focuses of the radiation tubes at both ends where radiation is emitted" according to the technique of the present disclosure. Here, a straight line GL which connects the focuses F1 to F15 arranged in a straight line and on which the positions SP1 to SP15 are set is parallel to the side of the imaging surface 45 in the X direction in a plan view of the radiation source 25 and the radiation detector 26 from the Z direction. That is, the X direction is an example of "a direction of a straight line connecting the focuses of the radiation tubes at both ends where radiation is emitted" according to the technique of the present disclosure. The straight line GL is offset to the front side (a side opposite to the support 20B) in the Y direction. The present disclosure is not limited to a case in which the intervals D_F between the focuses F1 to F15 are exactly equal to each other. For example, an error of ±5% is allowed in the interval D_F.

The irradiation angle of the radiation 37 is an angle formed between the normal line NR and a line connecting the center point CP and each of the focuses F1 to F15 of the radiation 37 in the radiation tubes 27 at the positions SP1 to SP15. Therefore, the irradiation angle at the position SP8 aligned with the normal line NR is 0°. FIG. 7 illustrates a line L1 connecting the focus F1 at the position SP1 and the center point CP and an irradiation angle θ(1) formed between the normal line NR and the line L1 as an example.

An angle represented by a symbol Ψ is the maximum scanning angle of tomosynthesis imaging. The maximum scanning angle Ψ is defined by the positions SP1 and SP15 at both ends among the positions SP1 to SP15. Specifically, the maximum scanning angle Ψ is an angle formed between the line L1 connecting the focus F1 at the position SP1 and the center point CP and a line L15 connecting the focus F15 at the position SP15 and the center point CP.

In one normal tomosynthesis imaging operation, each of the radiation tubes 27 at the positions SP1 to SP15 is operated to emit the radiation 37 to the breast M at each of the positions SP1 to SP15. The radiation detector 26 detects the radiation 37 emitted at each of the positions SP1 to SP15 whenever the radiation 37 is emitted and outputs the projection images P at the positions SP1 to SP15. The tomosynthesis imaging can be performed by both the CC imaging method illustrated in FIG. 5 and the MLO imaging method illustrated in FIG. 6. In the case of simple imaging in which the CC imaging illustrated in FIG. 5 and the MLO imaging illustrated in FIG. 6 are independently performed, only the radiation tube 27 disposed at the position SP8 where the irradiation angle is 0° is operated.

Figure 8:
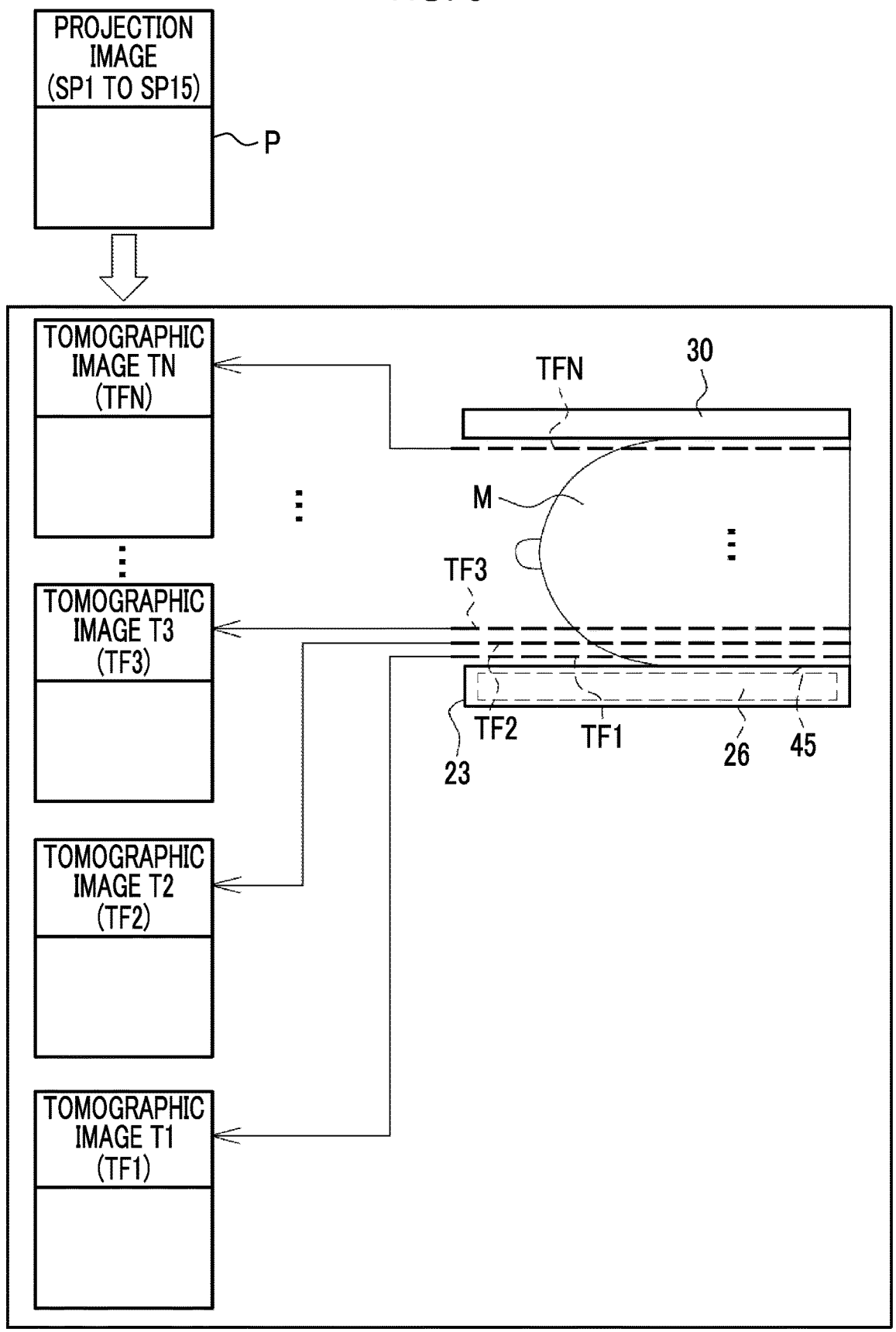
FIG. 8 is a diagram illustrating an aspect in which tomographic images are generated from a plurality of projection images obtained by the tomosynthesis imaging.

As illustrated in FIG. 8, in general, the mammography apparatus 10 generates tomographic images T1 to TN corresponding to any tomographic planes TF1 to TFN of the breast M from the plurality of projection images P at the plurality of positions SP1 to SP15 obtained by the tomosynthesis imaging illustrated in FIG. 7. The mammography apparatus 10 generates the tomographic images T1 to TN using a known method such as a filtered back projection method. The tomographic images T1 to TN are images in which structures in the tomographic planes TF1 to TFN have been highlighted. Adjacent radiation tubes 27 are disposed close to each other at a distance of, for example, several centimeters to several tens of centimeters in order to improve the SN ratio of the tomographic image T.

Figure 9:
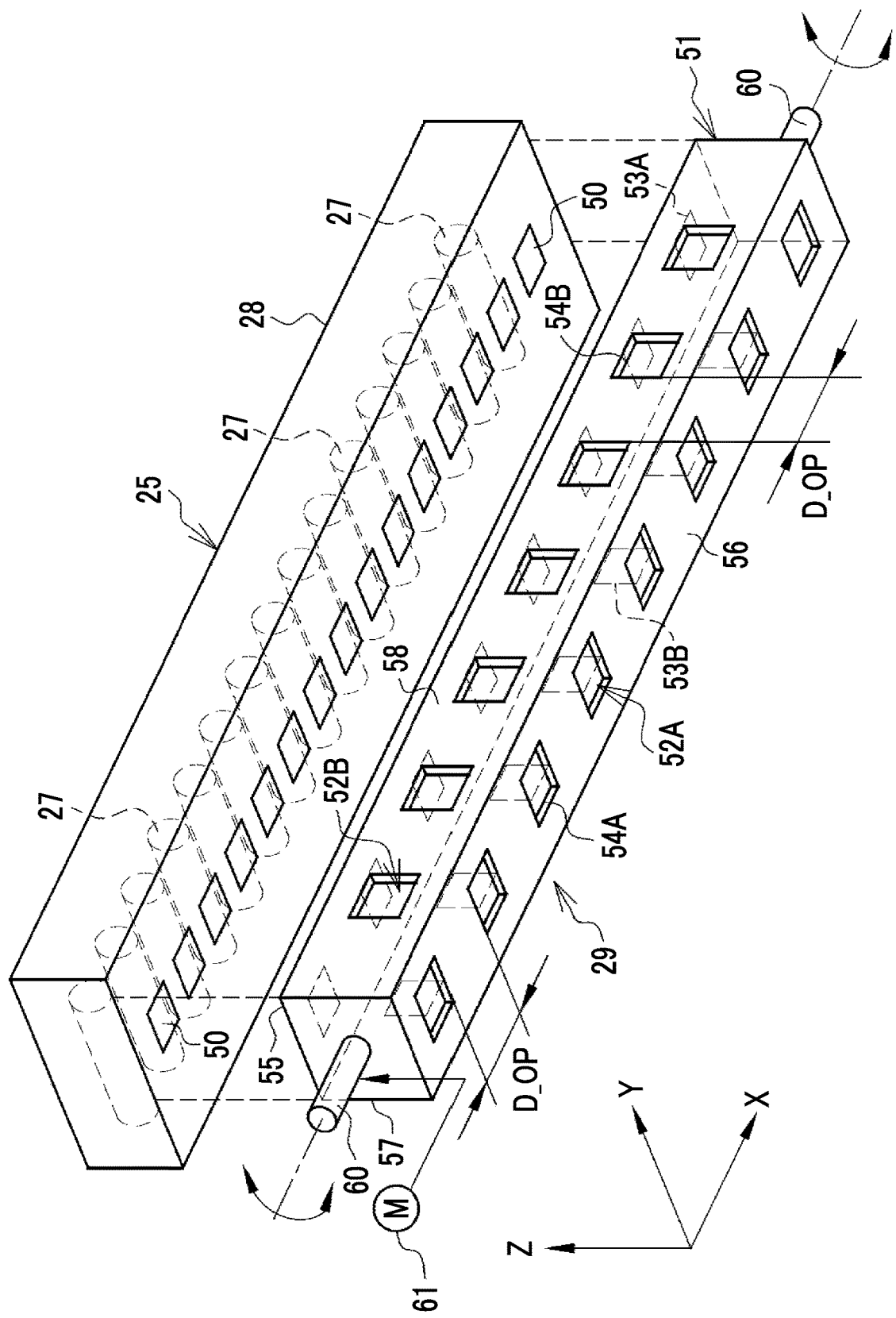
FIG. 9 is an exploded perspective view illustrating a radiation source and an irradiation field limiter.

As illustrated in FIG. 9, radiation transmission windows 50 that transmit the radiation 37 are provided in the lower surface of the housing 28 at corresponding positions immediately below each radiation tube 27. The radiation 37 emitted from each radiation tube 27 is emitted to the outside of the housing 28 through the radiation transmission windows 50.

The irradiation field limiter 29 includes a first rotating member 51. The outward appearance of the first rotating member 51 is a square prism that is long in the X direction and has a square shape (N=4) in a cross-sectional view taken along the Y direction which is the lateral direction. The first rotating member 51 is hollow. The first rotating member 51 is made of a material shielding the radiation 37 such as lead.

A total of 15 first irradiation opening portions 52 whose number is equal to the number of radiation tubes 27 are formed in the first rotating member 51 along the X direction. The first irradiation opening portion 52 is configured by a pair of a first opening 53 and a second opening 54 and defines the irradiation field of the radiation 37.

The first irradiation opening portions 52 include eight first irradiation opening portions 52A and seven first irradiation opening portions 52B. The first irradiation opening portion 52A is configured by a pair of a first opening 53A and a second opening 54A and the first irradiation opening portion 52B is configured by a pair of a first opening 53B and a second opening 54B. The first opening 53A and the second opening 54A are formed at positions opposite to each other in the irradiation direction of the radiation 37 in first and second surfaces 55 and 56 of the first rotating member 51 which have a rectangular shape and are opposite to each other, respectively. Further, the first opening 53B and the second opening 54B are formed at positions opposite to each other in the irradiation direction of the radiation 37 in third and fourth surfaces 57 and 58 of the first rotating member 51 which have a rectangular shape and are opposite to each other, respectively. The first opening 53A and the second opening 54A forming one first irradiation opening portion 52A have the same size. Similarly, the first opening 53B and the second opening 54B forming one first irradiation opening portion 52B have the same size.

The first irradiation opening portions 52A adjacent to each other are separated by an interval D_OP. Similarly, the first irradiation opening portions 52B adjacent to each other are separated by the interval D_OP. The interval D_OP is nearly equal to an interval of one radiation tube 27. Further, the first irradiation opening portion 52A and the second irradiation opening portion 52B deviate from each other in the X direction and are alternately arranged in the X direction.

A pair of rotating shafts 60 parallel to the X direction are attached to the centers of two side surfaces of the first rotating member 51 which are opposite to each other in the X direction. A motor 61 is connected to the rotating shaft 60. The first rotating member 51 is rotated about the rotating shaft 60 by the operation of the motor 61. The rotating shafts 60 are not limited to a configuration in which the rotating shafts 60 are completely parallel in the X direction. For example, an error of ±5% is allowed.

As illustrated in FIG. 10, the first rotating member 51 is rotated to two rotation positions of a first rotation position ((A) of FIG. 10) and a second rotation position ((B) of FIG. 10). At the first rotation position illustrated in (A) of FIG. 10, the first surface 55 faces the radiation tubes 27, the second surface 56 faces the radiation detector 26, and the first irradiation opening portion 52A faces the radiation tube 27. In contrast, the second rotation position illustrated in (B) of FIG. 10 is a position which is rotated by 90° (=360°/4) from the first rotation position and where the third surface 57 faces the radiation tube 27, the fourth surface 58 faces the radiation detector 26, and the first irradiation opening portion 52B faces the radiation tube 27. As described above, the first irradiation opening portion 52A and the first irradiation opening portion 52B deviate from each other in the X direction so as to face different radiation tubes 27 in the irradiation direction of the radiation 37 at the first rotation position and the second rotation position.

At the first rotation position, the radiation 37 is incident through the first opening 53A and exits through the second opening 54A. That is, the first opening 53A is an incident opening and the second opening 54A is an exit opening. At the second rotation position, the radiation 37 is incident through the first opening 53B and exits through the second opening 54B. That is, the first opening 53B is an incident opening and the second opening 54B is an exit opening.

Figure 11:
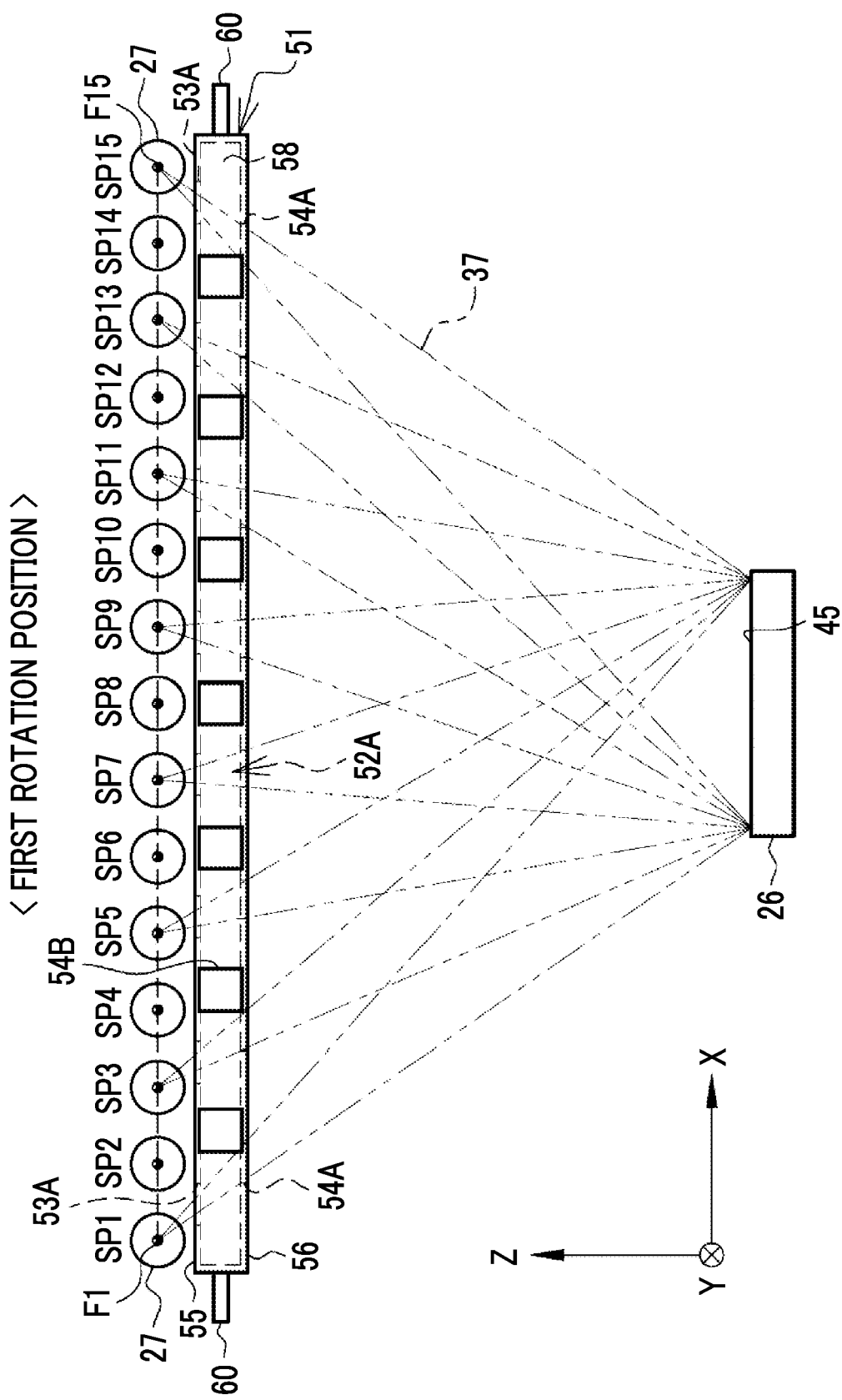
FIG. 11 is a diagram illustrating an aspect of the tomosynthesis imaging at the first rotation position.

As illustrated in FIG. 11, at the first rotation position, the first irradiation opening portions 52A define the irradiation field of the radiation 37 emitted from the radiation tubes 27 disposed at the positions SP1, SP3, SP5, SP7, SP9, SP11, SP13, and SP15. In contrast, as illustrated in FIG. 12, at the second rotation position, the first irradiation opening portions 52B define the irradiation field of the radiation 37 emitted from the radiation tubes 27 disposed at the positions SP2, SP4, SP6, SP8, SP10, SP12, and SP14.

As illustrated in FIG. 9, adjacent first irradiation opening portions 52A and adjacent first irradiation opening portions 52B are separated from each other by the interval D_OP which is nearly equal to an interval of one radiation tube 27. Therefore, at the first rotation position, the first irradiation opening portions 52A do not face the radiation tubes 27 disposed at the positions SP2, SP4, SP6, SP8, SP10, SP12, and SP14. Further, at the second rotation position, the first irradiation opening portions 52B do not face the radiation tubes 27 disposed at the positions SP1, SP3, SP5, SP7, SP9, SP11, SP13, and SP15.

Figure 12:
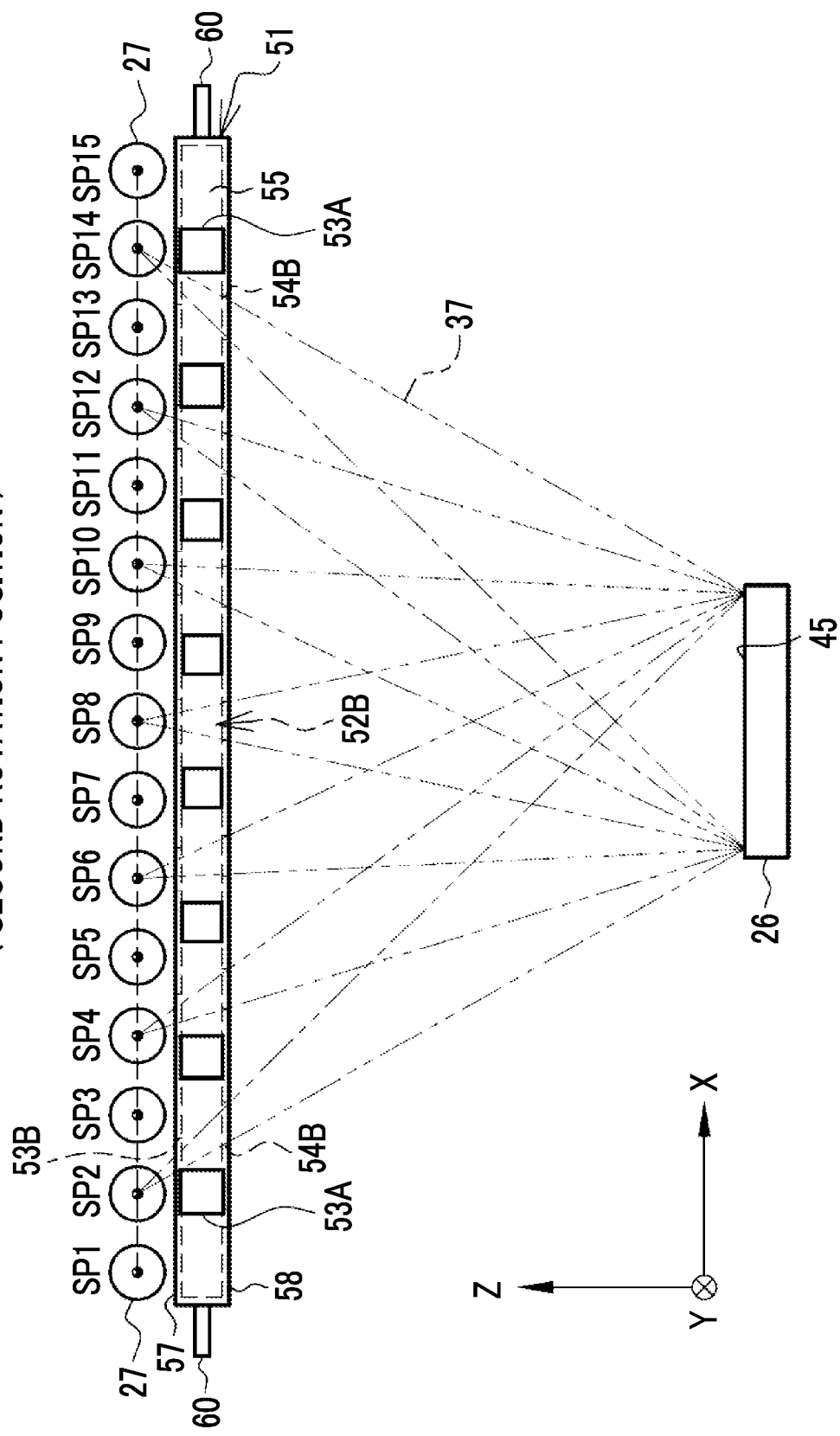
FIG. 12 is a diagram illustrating an aspect of the tomosynthesis imaging at the second rotation position.

FIG. 13 illustrates a summary of the content illustrated in FIGS. 11 and 12. (A) of FIG. 13 illustrates a main portion in the case of the first rotation position illustrated in FIG. 11. In contrast, (B) of FIG. 13 illustrates a main portion in the case of the second rotation position illustrated in FIG. 12. As described above, the first opening 53 and the second opening 54 are formed at positions that face each other in the irradiation direction of the radiation 37. In addition, the first opening 53 and the second opening 54 forming one first irradiation opening portion 52 have the same size. Therefore, at both the first rotation position and the second rotation position, the irradiation field is defined by the second openings 54A and 54B disposed on the side of the radiation detector 26.

Figure 14:
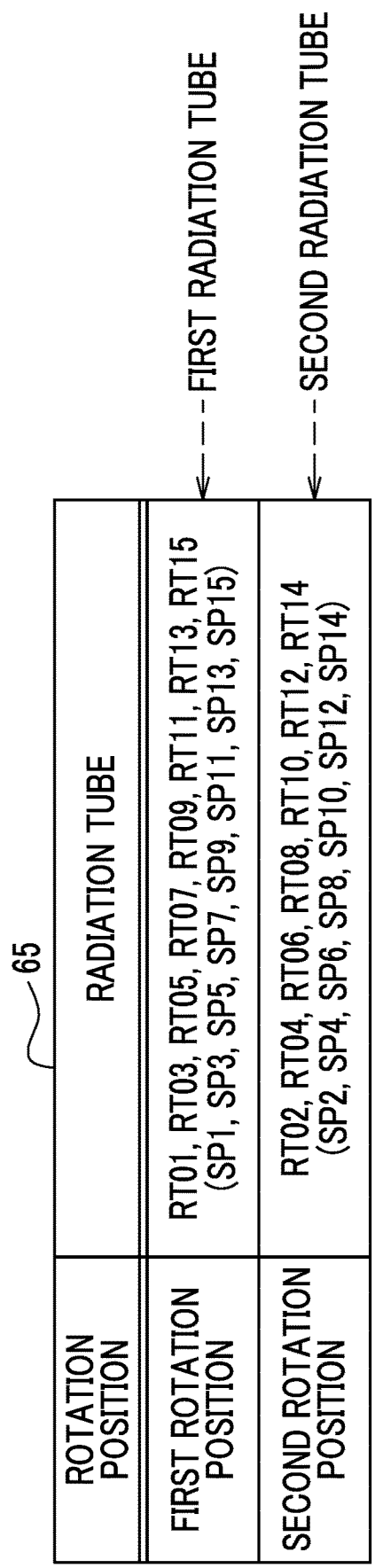
FIG. 14 is a table illustrating the radiation tube IDs of the radiation tubes that emit radiation at each rotation position.

FIG. 14 illustrates a table 65 showing the radiation tube identification data (ID) of the radiation tubes 27 that emit the radiation 37 at each of the first rotation position and the second rotation position. For the radiation tube ID, numbers are linked to each of the positions SP1 to SP15. For example, the radiation tube 27 disposed at the position SP1 is represented by RT01, the radiation tube 27 disposed at the position SP2 is represented by RT02, . . . , the radiation tube 27 disposed at the position SP14 is represented by RT14, and the radiation tube 27 disposed at the position SP15 is represented by RT15.

At the first rotation position, the radiation tubes 27 having the radiation tube IDs RT01, RT03, RT05, RT07, RT09, RT11, RT13, and RT15 face the first irradiation opening portions 52A and the radiation 37 is emitted from these radiation tubes 27. That is, the radiation tubes 27 having the radiation tube IDs RT01, RT03, RT05, RT07, RT09, RT11, RT13, and RT15 are an example of "the first radiation tubes facing the first irradiation opening portions at the first rotation position" according to the technique of the present disclosure.

In contrast, at the second rotation position, the radiation tubes 27 having the radiation tube IDs RT02, RT04, RT06, RT08, RT10, RT12, and RT14 face the first irradiation opening portions 52B and the radiation 37 is emitted from these radiation tubes 27. That is, the radiation tubes 27 having the radiation tube IDs RT02, RT04, RT06, RT08, RT10, RT12, and RT14 are an example of "the second radiation tubes that do not face the first irradiation opening portions and are other than the first radiation tubes facing the first irradiation opening portions at the first rotation position" according to the technique of the present disclosure.

Figure 15:
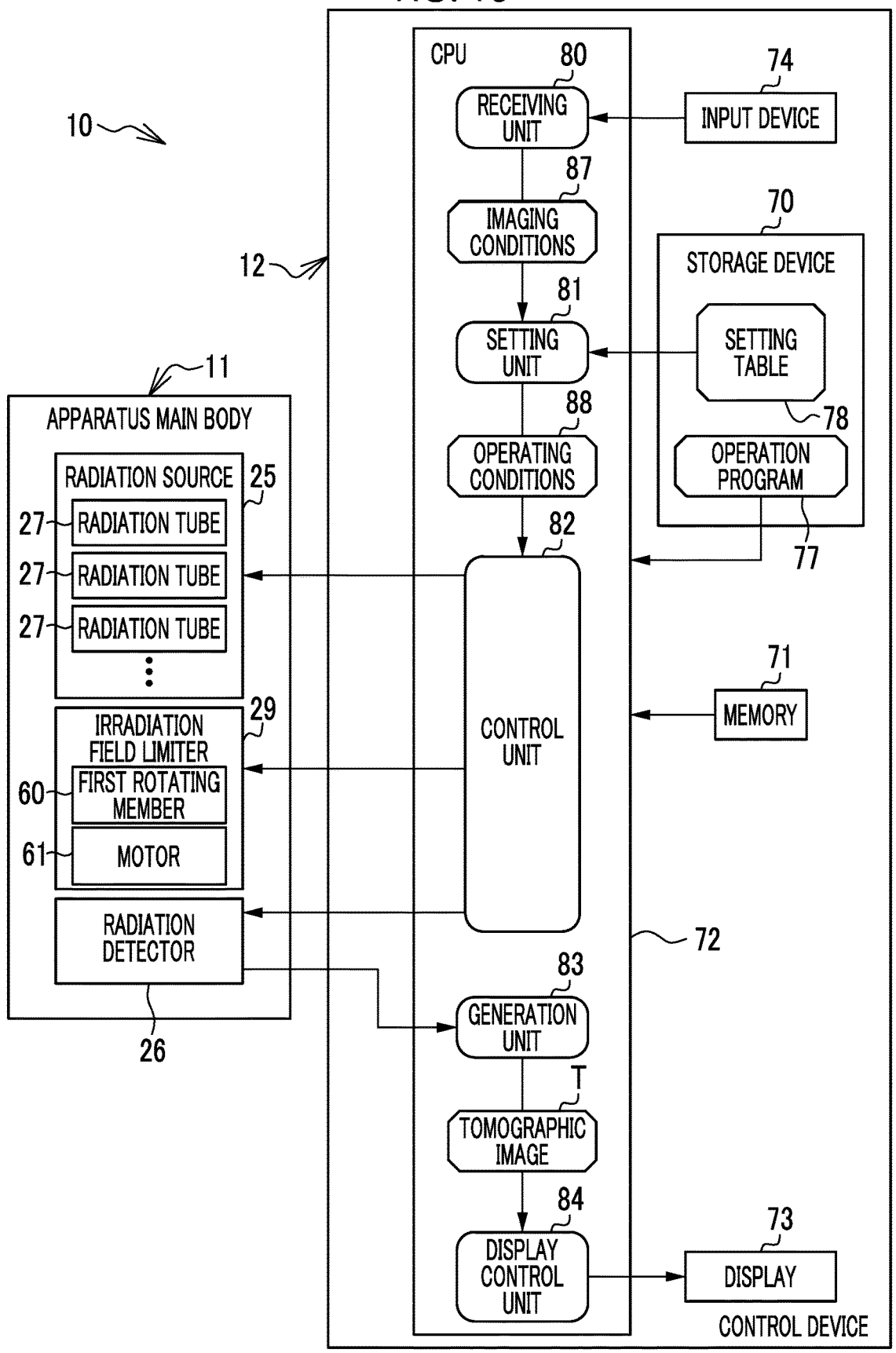
FIG. 15 is a block diagram mainly illustrating a processing unit of a CPU of a control device.

In FIG. 15, the computer forming the control device 12 comprises, for example, a storage device 70, a memory 71, a central processing unit (CPU) 72, a display 73, and an input device 74.

The storage device 70 is a hard disk drive that is provided in the computer forming the control device 12 or is connected to the computer through a cable or a network. Alternatively, the storage device 70 is a disk array in which a plurality of hard disk drives are connected. The storage device 70 stores a control program, such as an operating system, various application programs, and various kinds of data associated with these programs. In addition, a solid state drive may be used instead of the hard disk drive.

The memory 71 is a work memory used by the CPU 72 to perform processes. The CPU 72 loads the program stored in the storage device 70 to the memory 71 and performs a process corresponding to the program to control the overall operation of each unit of the computer.

The display 73 displays various screens. The various screens have operation functions by a graphical user interface (GUI). The computer forming the control device 12 receives operation commands input from the input device 74 through various screens. The input device 74 is, for example, a keyboard, a mouse, or a touch panel.

An operation program 77 is stored in the storage device 70. The operation program 77 is an application program for causing the computer to function as the control device 12. The storage device 70 stores a setting table 78 in addition to the operation program 77.

In a case in which the operation program 77 is started, the CPU 72 of the control device 12 functions as a receiving unit 80, a setting unit 81, a control unit 82, a generation unit 83, and a display control unit 84 in cooperation with, for example, the memory 71.

The receiving unit 80 receives imaging conditions 87 input by the operator through the input device 74. The receiving unit 80 outputs the imaging conditions 87 to the setting unit 81.

The setting unit 81 receives the imaging conditions 87 from the receiving unit 80. In addition, the setting unit 81 reads out the setting table 78 from the storage device 70. The setting unit 81 sets operating conditions 88 of the radiation tubes 27 and the motor 61 on the basis of the imaging conditions 87 and the setting table 78. The setting unit 81 outputs the operating conditions 88 to the control unit 82.

The control unit 82 controls the operation of the radiation source 25, the radiation detector 26, and the irradiation field limiter 29. The control unit 82 receives the operating conditions 88 from the setting unit 81. The control unit 82 operates the radiation tubes 27 and the motor 61 on the basis of the operating conditions 88 such that the radiation 37 is emitted from the radiation tubes 27. The control unit 82 recognizes whether the first rotating member 51 is at the first rotation position or the second rotation position on the basis of, for example, a detection signal of a rotary encoder. The control unit 82 outputs the projection image P detected by the radiation detector 26 by the emission of the radiation 37 from the radiation detector 26 to the generation unit 83.

The generation unit 83 receives the plurality of projection images P from the radiation detector 26. The generation unit 83 generates tomographic images T on the basis of the plurality of projection images P. The generation unit 83 outputs the tomographic images T to the display control unit 84.

The display control unit 84 receives the tomographic images T from the generation unit 83. The display control unit 84 performs control to display the received tomographic images T on the display 73.

Figure 16:
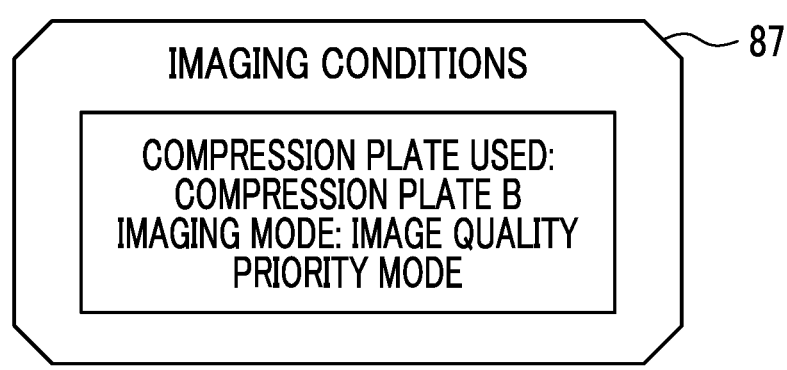
FIG. 16 is a diagram illustrating imaging conditions.

As illustrated in FIG. 16, the imaging conditions 87 include the compression plate 30 used (described as a compression plate used in FIG. 16) and an imaging mode. As described above, the compression plate 30 is interchanged according to, for example, the size of the breast M. In the tomosynthesis imaging, the radiation tube 27 that emits the radiation 37 varies depending on the compression plate 30 used (see FIG. 17). Therefore, the compression plate 30 used is included in the imaging conditions 87.

The imaging mode includes an image quality priority mode and an exposure reduction mode (see FIG. 17). The image quality priority mode is a mode in which the radiation 37 is emitted from as many radiation tubes 27 as possible to increase the SN ratio of the tomographic image. In contrast, the exposure reduction mode is a mode in which the minimum amount of radiation 37 is emitted to reduce the exposure of the subject H as much as possible. Since the radiation tube 27 that emits the radiation 37 varies depending on each of the imaging modes (see FIG. 17), the imaging mode is included in the imaging conditions 87.

FIG. 16 illustrates imaging conditions 87 in which a compression plate B is registered as the compression plate 30 used and the image quality priority mode is registered as the imaging mode. In addition to the compression plate 30 used and the imaging mode, information for changing the radiation tube 27 that emits the radiation 37 may be added to the imaging conditions 87.

As illustrated in FIG. 17, in the setting table 78, the radiation tube IDs of the radiation tubes 27 (described as the radiation tubes used in FIG. 17) that emit the radiation 37 are registered for each combination of the compression plate 30 used and the imaging mode.

In the exposure reduction mode, the number of radiation tubes 27 that emit the radiation 37 is smaller than that in the image quality priority mode. For example, in a case in which the compression plate 30 used is the compression plate B, a total of 13 radiation tubes 27 having the radiation tube IDs RT02 to RT14 are registered in the image quality priority mode. In contrast, in the exposure reduction mode, a total of seven radiation tubes 27 having the radiation tube IDs RT02, RT04, RT06, RT08, RT10, RT12, and RT14 are registered.

In FIG. 18, in the operating conditions 88, the radiation tube ID of the radiation tube 27, and the rotation position of the first rotating member 51 are registered for each irradiation number of the radiation 37. FIG. 18 illustrates the operating conditions 88 in a case in which the content of the imaging conditions 87 is as illustrated in FIG. 16, that is, is that the compression plate 30 used is the compression plate B and the imaging mode is the image quality priority mode. In a case in which the content of the imaging conditions 87 is as illustrated in FIG. 16, the setting table 78 illustrated in FIG. 17 shows that the radiation tubes 27 with the radiation tube IDs RT02 to RT14 emit the radiation 37. Therefore, in the operating conditions 88, first, for irradiation numbers 1 to 6, RT03, RT05, RT07, RT09, RT11, and RT13 are registered as the radiation tube IDs and the first rotation position is registered as the rotation position of the first rotating member 51. Then, for irradiation numbers 7 to 13, RT02, RT04, RT06, RT08, RT10, RT12, and RT14 are registered as the radiation tube IDs and the second rotation position is registered as the rotation position of the first rotating member 51.

In the case of the operating conditions 88 illustrated in FIG. 18, the control unit 82 performs control such that the radiation tubes 27 with the radiation tube IDs RT03, RT05, RT07, RT09, RT11, RT13, RT02, RT04, RT06, RT08, RT10, RT12, and RT14 emit the radiation 37 in this order. Further, the control unit 82 operates the motor 61 between irradiation number 6 and irradiation number 7 to rotate the first rotating member 51 by 90° such that the rotation position of the first rotating member 51 is changed from the first rotation position to the second rotation position.

As another example, a case is considered in which the content of the imaging conditions 87 is that the compression plate 30 used is the compression plate B and the imaging mode is the exposure reduction mode. In this case, according to the setting table 78, the radiation tubes 27 with the radiation tube IDs RT02, RT04, RT06, RT08, RT10, RT12, and RT14 emit the radiation 37. Therefore, in this case, the rotation position of the first rotating member 51 is maintained as the second rotation position from beginning to end.

Figure 19:
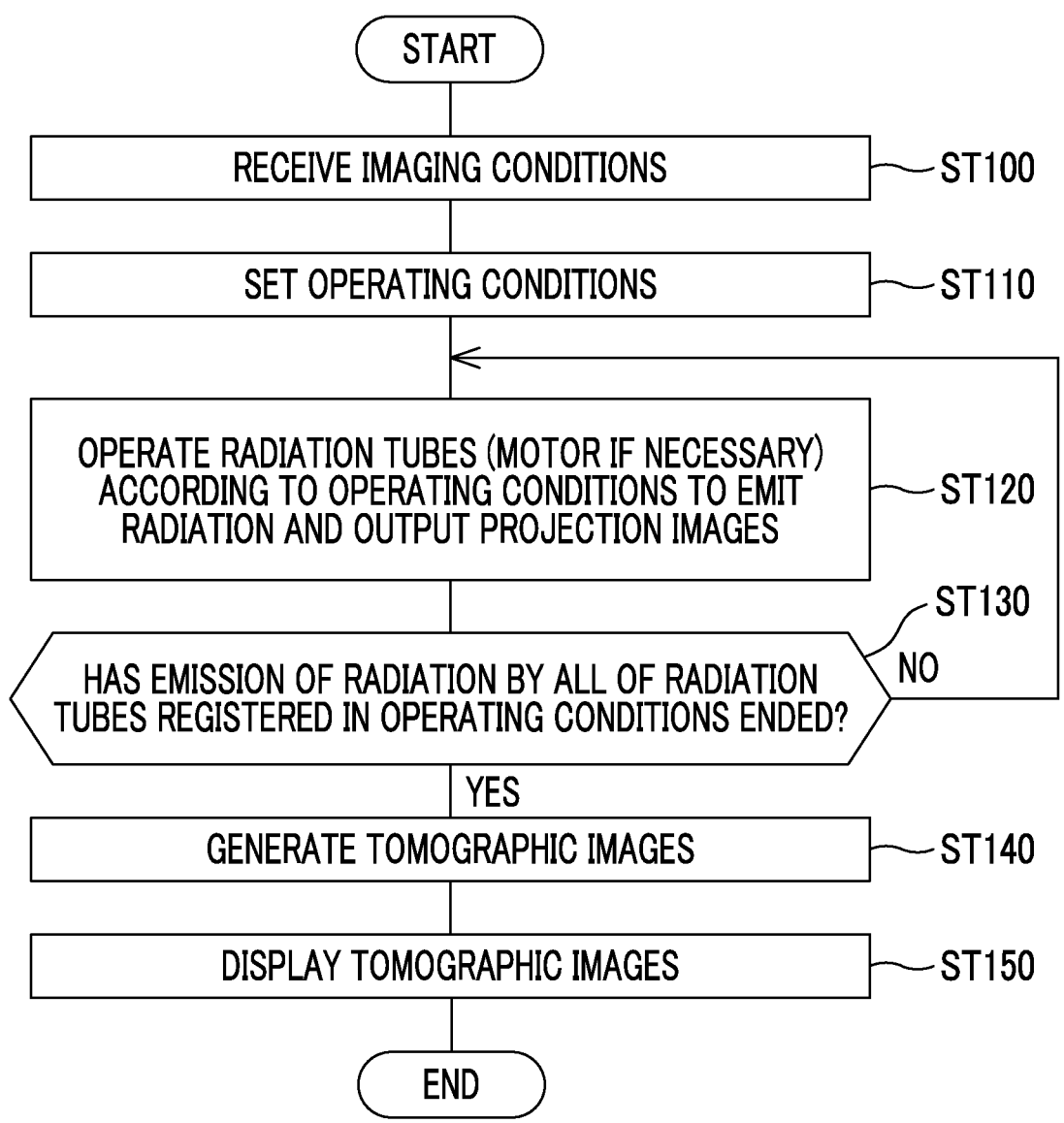
FIG. 19 is a flowchart illustrating a process procedure of the control device.

Next, the operation of the above-mentioned configuration will be described with reference to a flowchart illustrated in FIG. 19. In a case in which the operation program 77 is started, the CPU 72 of the control device 12 functions as the receiving unit 80, the setting unit 81, the control unit 82, the generation unit 83, and the display control unit 84 as illustrated in FIG. 15.

First, the receiving unit 80 receives the imaging conditions 87 (Step ST100). The imaging conditions 87 are output from the receiving unit 80 to the setting unit 81. Then, the setting unit 81 sets the operating conditions 88 on the basis of the imaging conditions 87 and the setting table 78 (Step ST110). The operating conditions 88 are output from the setting unit 81 to the control unit 82.

In Step ST120, the control unit 82 operates the radiation tubes 27 according to the operating conditions 88. The radiation 37 emitted from the radiation tube 27 is incident on the irradiation field limiter 29 through the radiation transmission window 50. The radiation 37 incident on the irradiation field limiter 29 passes through the first irradiation opening portion 52 of the first rotating member 51. The irradiation field of the radiation 37 is defined in this way. As illustrated in FIG. 9, the first irradiation opening portions 52 are arranged at the interval D_OP that is nearly equal to an interval of one radiation tube 27. Therefore, in a case in which the radiation 37 is emitted from a certain radiation tube 27, the leakage of the radiation 37 from the adjacent first irradiation opening portions 52 is suppressed.

In Step ST120, the control unit 82 operates the motor 61 on the basis of the operating conditions 88 to rotate the first rotating member 51 to the first rotation position or the second rotation position, if necessary. As illustrated in, for example, FIG. 9, the first irradiation opening portions 52A that face the radiation tubes 27 at the first rotation position and the first irradiation opening portions 52B that face the radiation tubes 27 at the second rotation position deviate from each other in the X direction. As a result, as illustrated in FIGS. 11 to 14, the radiation tubes 27 facing the first irradiation opening portions 52 are different between the first rotation position and the second rotation position.

The radiation 37 of which the irradiation field has been defined by the first irradiation opening portion 52 and which has been emitted to the breast M is detected by the radiation detector 26. Then, the projection images P are output from the radiation detector 26 to the generation unit 83. Step ST120 is repeatedly performed in a case in which the emission of the radiation 37 by all of the radiation tubes 27 registered in the operating conditions 88 does not end (NO in Step ST130).

In a case in which the emission of the radiation 37 by all of the radiation tubes 27 registered in the operating conditions 88 ends (YES in Step ST130), the generation unit 83 generates the tomographic images T on the basis of the projection images P from the radiation detector 26 (Step ST140). The tomographic images T are output from the generation unit 83 to the display control unit 84. The tomographic images T are displayed on the display 73 by the display control unit 84 and are provided for the operator to browse (Step ST150).

As described above, the mammography apparatus 10 uses the irradiation field limiter 29 including the first rotating member 51 that is rotated to the first rotation position and the second rotation position about the rotating shaft 60 parallel to the X direction with respect to the radiation source 25 having three or more radiation tubes 27. At the first rotation position and the second rotation position, the first irradiation opening portions 52 which are arranged at the interval D_OP corresponding to at least one radiation tube 27 face the radiation tubes 27 in the irradiation direction of the radiation 37. The first irradiation opening portions 52 deviate from each other in the X direction. Among three or more radiation tubes 27, at least some of the radiation tubes 27 that do not face the first irradiation opening portions 52 except the radiation tubes 27 facing the first irradiation opening portions 52 at the first rotation position face the first irradiation opening portions at the second rotation position. Therefore, it is possible to prevent unnecessary exposure.

The following methods can be considered as other methods for preventing unnecessary exposure. That is, a plate-like member in which openings are formed at the interval D_OP corresponding to at least one radiation tube 27 is disposed immediately below the radiation tubes 27. Then, the plate-like member is moved along the direction (X direction) of a straight line connecting the focuses F of the radiation tubes 27 at both ends. Therefore, one opening is shared by two or more radiation tubes 27. However, since this method requires a space for allowing the movement of the plate-like member, the size of the irradiation field limiter increases. In contrast, according to the technique of the present disclosure, it is possible to avoid an increase in the size of the irradiation field limiter.

As illustrated in, for example, FIG. 13, in this embodiment, the irradiation field is defined by the second opening 54. Therefore, the size and shape of the first opening 53 may be relatively rough and unnecessary labor is not required to form the first opening 53.

The first rotating member 51 has a square shape in a cross-sectional view taken along the lateral direction. Therefore, it is easy to manufacture the first rotating member 51 in a simple shape. Further, the rotation positions are positions corresponding to 90 degrees (=360°/4). Therefore, it is easy to control the operation of the motor 61 by the control unit 82.

The first rotating member 51 is hollow. Therefore, the first irradiation opening portion 52 can be formed more easily than that in a case in which a solid rotating member is used and it is possible to suppress an increase in manufacturing costs. Further, the first rotating member 51 is lighter than the solid rotating member and is easier to rotate than the solid rotating member. Therefore, it is possible to reduce the operation load of the motor 61. Of course, the first rotating member 51 may be solid.

Figure 20:
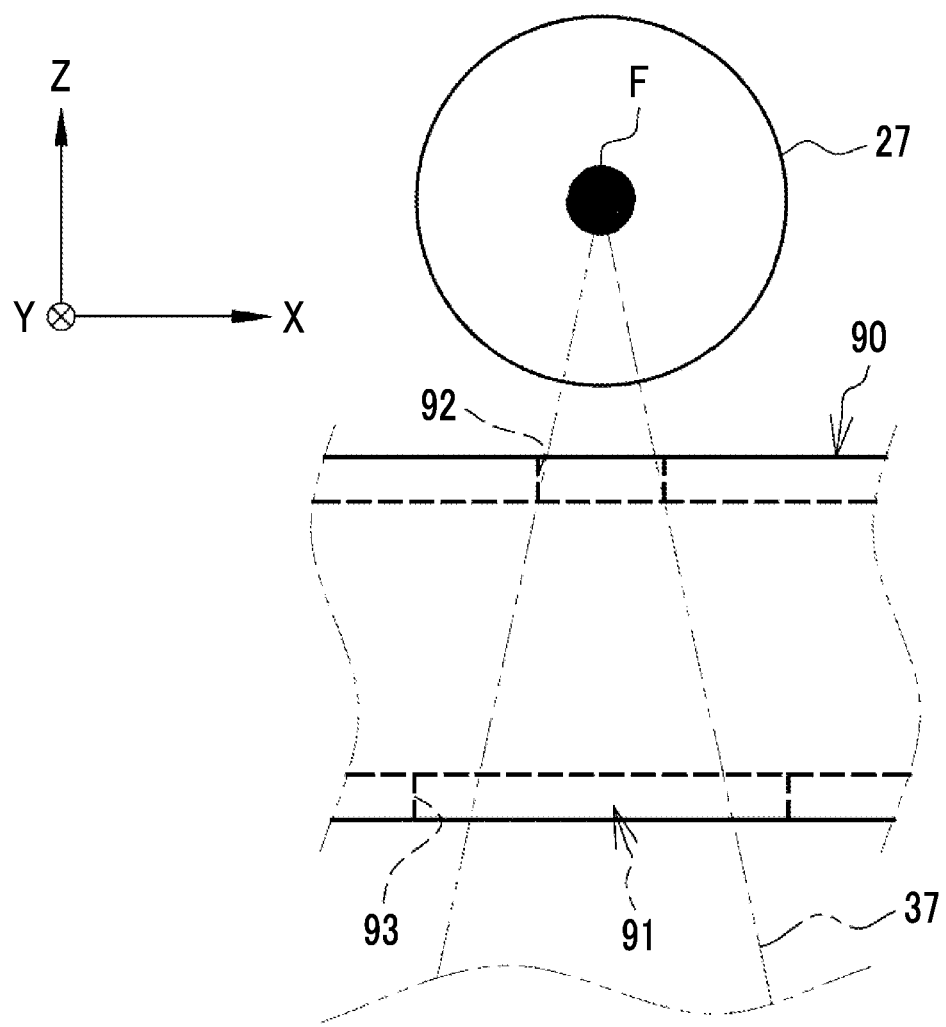
FIG. 20 is a diagram illustrating an example in which an irradiation field is defined by a first opening.

As in a first rotating member 90 illustrated in FIG. 20, the size of a first opening 92 forming the first irradiation opening portion 91 may be reduced and the size of a second opening 93 may be increased such that the irradiation field is defined by the first opening 92.

The following embodiments will be described on the premise that 15 radiation tubes 27 are disposed at the positions SP1 to SP15 as in the first embodiment.

Second Embodiment

In a second embodiment illustrated in FIGS. 21 and 22, an irradiation field limiter 95 is used in which the first rotating member 51 is divided into two rotating members, that is, a first rotating member 51_1 and a first rotating member 51_2.

In FIG. 21, a pair of rotating shafts 60_1 parallel to the X direction are attached to the centers of both side surfaces of the first rotating member 51_1 which are opposite to each other in the X direction. A motor 61_1 is connected to the rotating shaft 60_1. The first rotating member 51_1 is rotated about the rotating shaft 60_1 by the operation of the motor 61_1. Similarly, a pair of rotating shafts 60_2 parallel to the X direction are attached to the centers of both side surfaces of the first rotating member 51_2 which are opposite to each other in the X direction. A motor 61_2 is connected to the rotating shaft 60_2. The first rotating member 51_2 is rotated about the rotating shaft 60_2 by the operation of the motor 61_2. That is, the first rotating members 51_1 and 51_2 are independently rotated.

The first rotating member 51_1 defines the irradiation field of the radiation 37 emitted from the radiation tubes 27 disposed at the positions SP1 to SP8. In addition, the first rotating member 51_2 defines the irradiation field of the radiation 37 emitted from the radiation tubes 27 disposed at the positions SP9 to SP15.

Specifically, first irradiation opening portions 52A_1 of the first rotating member 51_1 define the irradiation field of the radiation 37 emitted from the radiation tubes 27 disposed at the positions SP1, SP3, SP5, and SP7 at the first rotation position illustrated in FIG. 21. In contrast, first irradiation opening portions 52B_1 of the first rotating member 51_1 define the irradiation field of the radiation 37 emitted from the radiation tubes 27 disposed at the positions SP2, SP4, SP6, and SP8 at the second rotation position (not illustrated). Further, first irradiation opening portions 52A_2 of the first rotating member 51_2 define the irradiation field of the radiation 37 emitted from the radiation tubes 27 disposed at the positions SP9, SP11, SP13, and SP15 at the first rotation position. In contrast, first irradiation opening portions 52B_2 of the first rotating member 51_2 define the irradiation field of the radiation 37 emitted from the radiation tubes 27 disposed at the positions SP10, SP12, and SP14 at the second rotation position.

This disposition of two first rotating members 51_1 and 51_2 along the X direction makes it possible to perform the tomosynthesis imaging illustrated in Table 98 of FIG. 22. That is, while the radiation 37 is being emitted with the first rotating member 51_2 (described as the first rotating member (right) in FIG. 22) disposed at the first rotation position, the first rotating member 51_1 (described as the first rotating member (left) in FIG. 22) can be rotated to the second rotation position. In addition, while the radiation 37 is being emitted with the first rotating member 51_1 disposed at the second rotation position, the first rotating member 51_2 can be rotated to the second rotation position.

In the first embodiment, the emission of the radiation 37 and the rotation of the first rotating member 51 need to be performed separately. In contrast, according to the irradiation field limiter 95 of the second embodiment, the emission of the radiation 37 and the rotation of the first rotating member 51 can be performed together and the imaging time can be reduced.

The first rotating member 51 may be divided into three or more rotating members.

Third Embodiment

Figure 23:
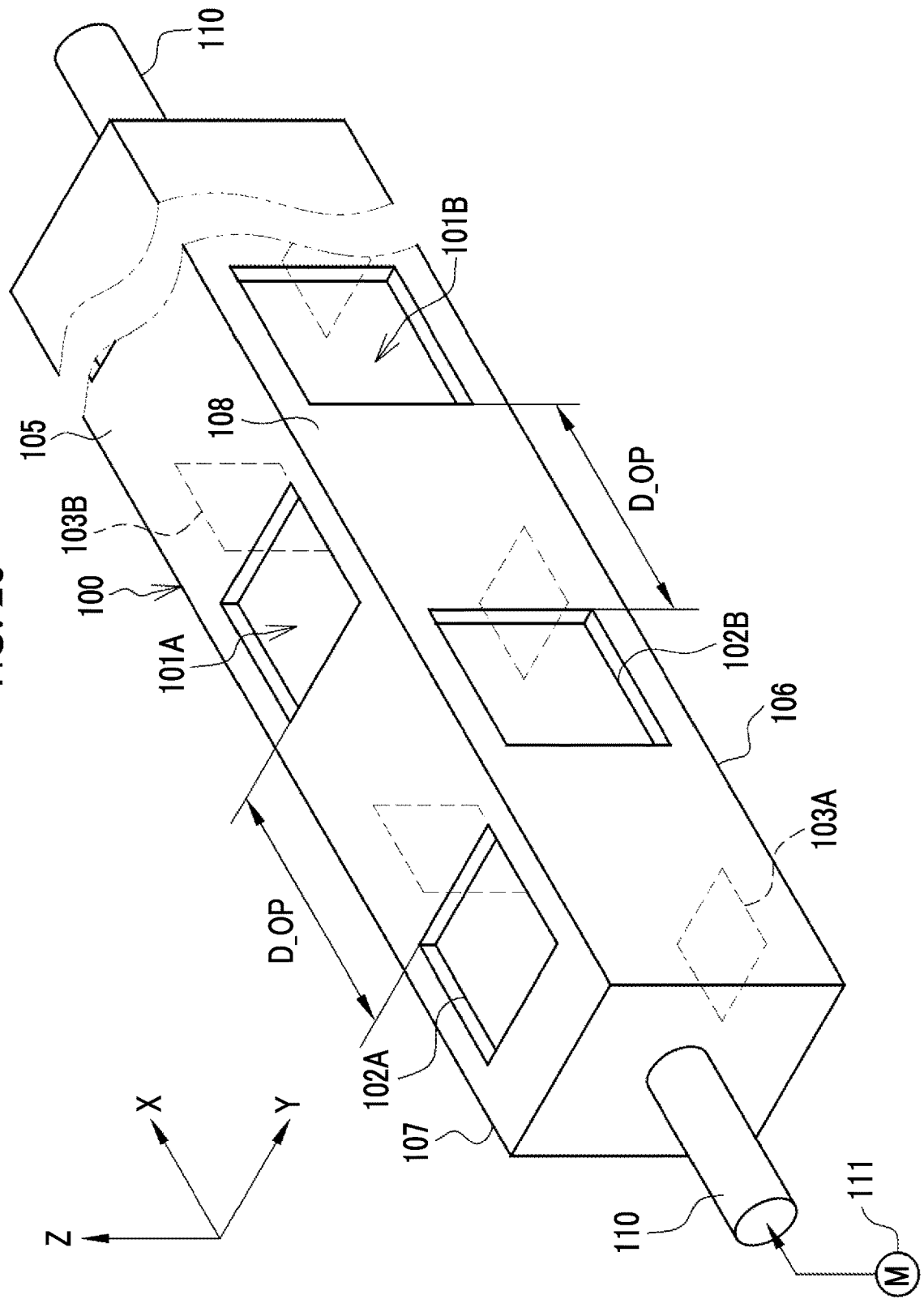
FIG. 23 is a perspective view illustrating a first rotating member having a first irradiation opening portion in which a first opening and a second opening have different sizes.
Figure 24:
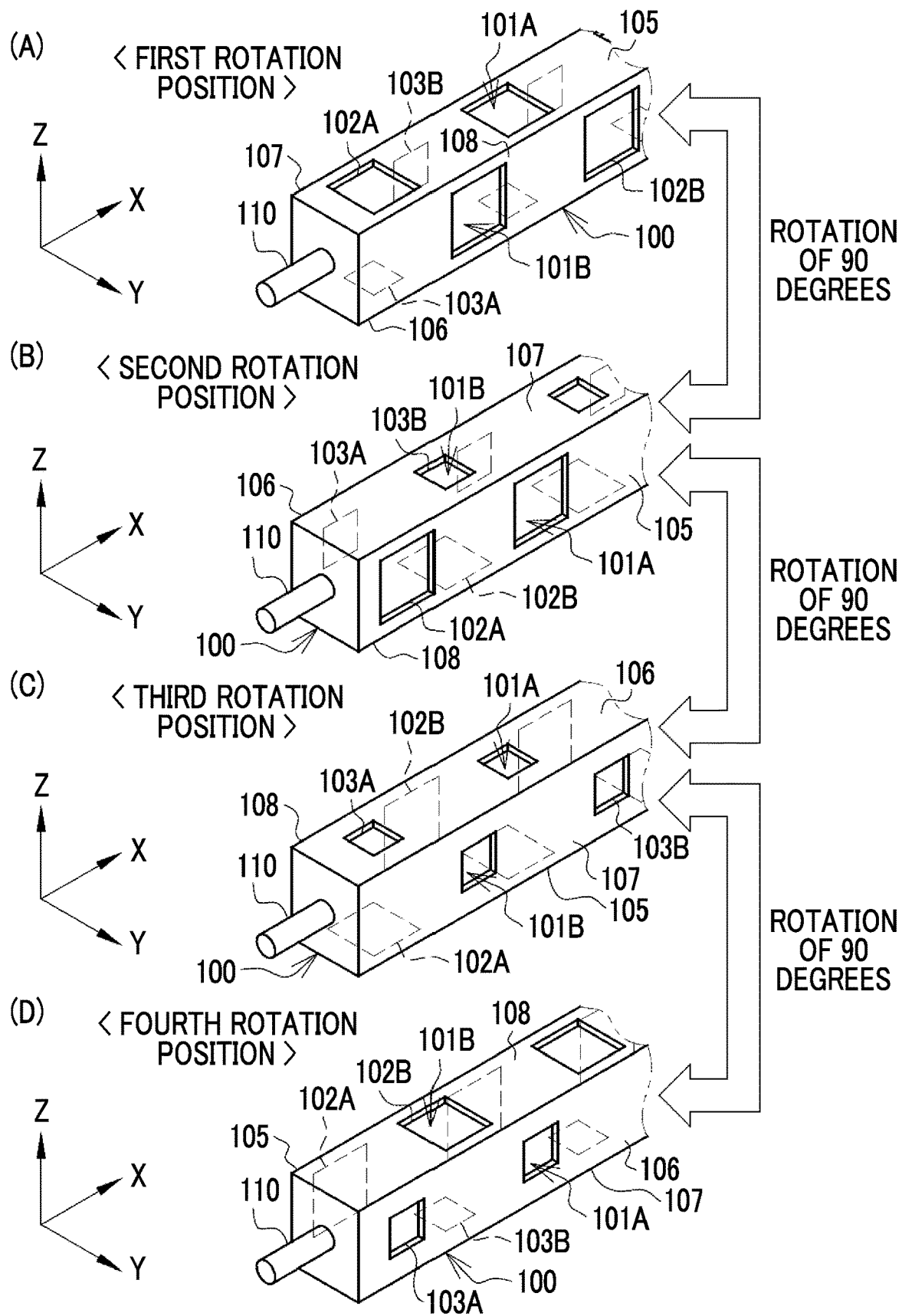
FIG. 24 is a diagram illustrating the first rotating member at each rotation position. (A) of FIG. 24 illustrates a first rotation position, (B) of FIG. 24 illustrates a second rotation position, (C) of FIG. 24 illustrates a third rotation position, and (D) of FIG. 24 illustrates a fourth rotation position.
Figure 25:
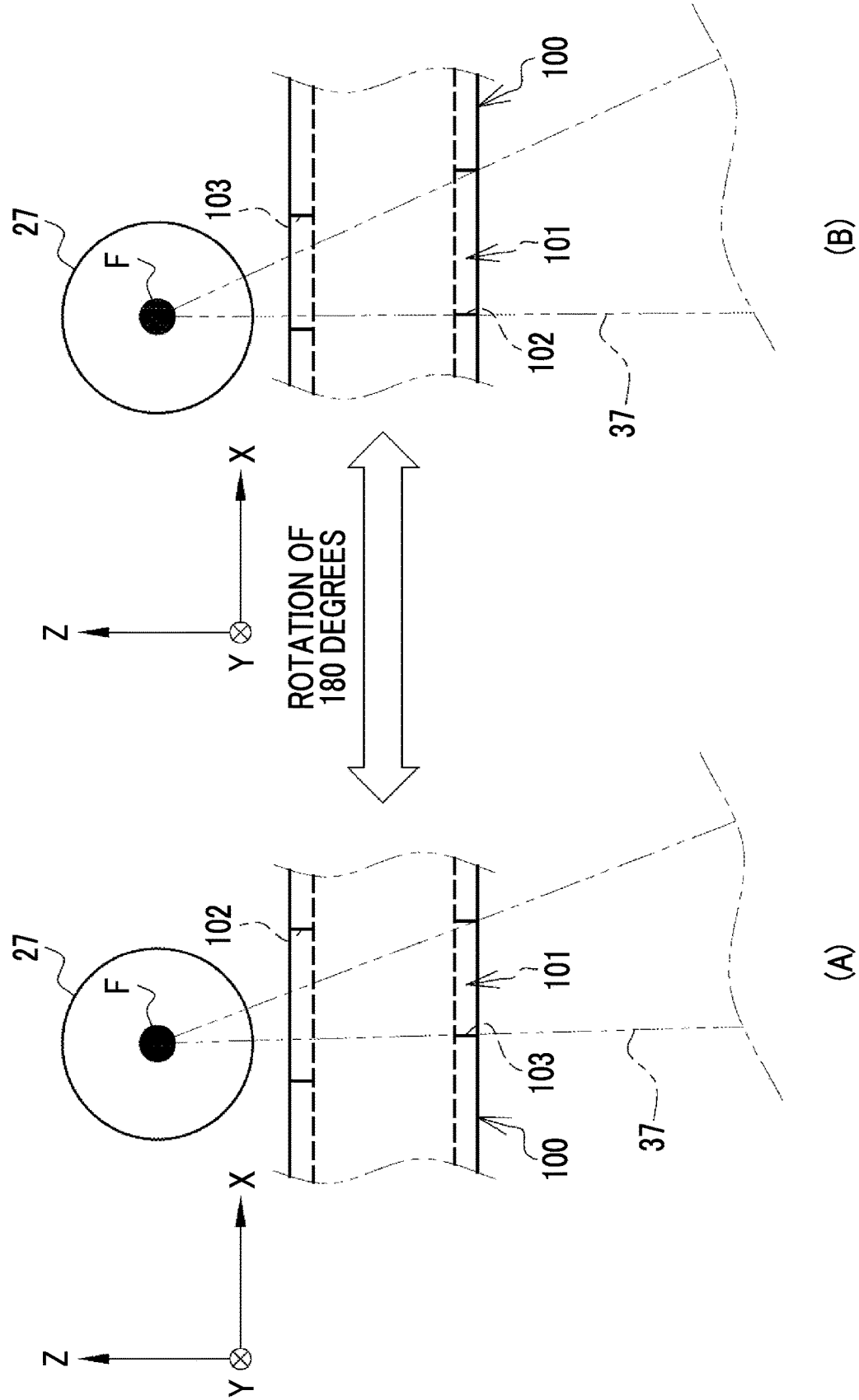
FIG. 25 is a diagram illustrating a relationship between one radiation tube and the first irradiation opening portion. (A) of FIG. 25 illustrates the first rotation position or the fourth rotation position and (B) of FIG. 25 illustrates the second rotation position or the third rotation position.

In a third embodiment illustrated in FIGS. 23 to 25, a first rotating member 100 having a first irradiation opening portion 101 in which a first opening 102 and a second opening 103 have different sizes is used.

In FIG. 23, the first rotating member 100 has first irradiation opening portions 101A and 101B. The first irradiation opening portion 101A is configured by a pair of a first opening 102A and a second opening 103A. The first irradiation opening portion 101B is configured by a pair of a first opening 102B and a second opening 103B. The first opening 102A and the second opening 103A are formed in a rectangular first surface 105 and a rectangular second surface 106 of the first rotating member 100 at positions that face each other in the irradiation direction of the radiation 37, respectively. In addition, the first opening 102B and the second opening 103B are formed in a rectangular third surface 107 and a rectangular fourth surface 108 of the first rotating member 100 at positions that face each other in the irradiation direction of the radiation 37, respectively. The size of the first opening 102A is slightly larger than that of the second opening 103A. Similarly, the size of the first opening 102B is slightly larger than that of the second opening 103B.

Adjacent first irradiation opening portions 101A are separated from each other by an interval D_OP. Similarly, adjacent first irradiation opening portions 101B are separated from each other by the interval D_OP. The interval D_OP is nearly equal to an interval of one radiation tube 27. Further, the first irradiation opening portion 101A and the second irradiation opening portion 101B deviate from each other in the X direction and are alternately arranged in the X direction.

A pair of rotating shafts 110 parallel to the X direction are attached to the centers of both side surfaces of the first rotating member 100 which are opposite to each other in the X direction. A motor 111 is connected to the rotating shaft 110. The first rotating member 100 is rotated about the rotating shaft 110 by the operation of the motor 111.

As illustrated in FIG. 24, the first rotating member 100 is rotated to four rotation positions, that is, a first rotation position ((A) of FIG. 24), a second rotation position ((B) of FIG. 24), a third rotation position ((C) of FIG. 24), and a fourth rotation position ((D) of FIG. 24). At the first rotation position illustrated in (A) of FIG. 24, the first surface 105 faces the radiation tubes 27, the second surface 106 faces the radiation detector 26, and the first irradiation opening portions 101A face the radiation tubes 27. The second rotation position illustrated in (B) of FIG. 24 is a position which is rotated by 90° from the first rotation position and where the third surface 107 faces the radiation tubes 27, the fourth surface 108 faces the radiation detector 26, and the first irradiation opening portions 101B face the radiation tubes 27. The third rotation position illustrated in (C) of FIG. 24 is a position which is rotated by 90° from the second rotation position and is rotated by 180° from the first rotation position and where the second surface 106 faces the radiation tubes 27, the first surface 105 faces the radiation detector 26, and the first irradiation opening portions 101A face the radiation tubes 27. The fourth rotation position illustrated in (C) FIG. 24 is a position which is rotated by 90° from the third rotation position and is rotated by 180° from the second rotation position and where the fourth surface 108 faces the radiation tubes 27, the third surface 107 faces the radiation detector 26, and the first irradiation opening portions 101B face the radiation tubes 27.

At the first rotation position, the radiation 37 is incident through the first opening 102A and exits through the second opening 103A. That is, the first opening 102A is an incident opening and the second opening 103A is an exit opening. At the second rotation position, the radiation 37 is incident through the second opening 103B and exits through the first opening 102B. That is, the second opening 103B is an incident opening and the first opening 102B is an exit opening. At the third rotation position, the radiation 37 is incident through the second opening 103A and exits through the first opening 102A. That is, contrary to the first rotation position, the second opening 103A is an incident opening and the first opening 102A is an exit opening. At the fourth rotation position, the radiation 37 is incident through the first opening 102B and exits through the second opening 103B. That is, contrary to the second rotation position, the first opening 102B is an incident opening and the second opening 103B is an exit opening.

FIG. 25 illustrates the relationship between one radiation tube 27 and the first irradiation opening portion 101. (A) of FIG. 25 illustrates the case of the first rotation position or the fourth rotation position and (B) of FIG. 25 illustrates the case of the second rotation position or the third rotation position. In the case of the first rotation position or the fourth rotation position, the irradiation field is defined by the second opening 103 disposed on the side of the radiation detector 26. In contrast, in the case of the second rotation position and the third rotation position, the irradiation field is defined by the first opening 102 disposed on the side of the radiation detector 26. As described above, the size of the first opening 102 is slightly larger than the size of the second opening 103. Therefore, the size of the irradiation field at the first rotation position or the fourth rotation position is larger than that at the second rotation position and the third rotation position.

As described above, in the third embodiment, the first rotating member 100 in which the first opening 102 and the second opening 103 have different sizes is used. Therefore, it is possible to change the size of the irradiation field as illustrated in FIG. 25.

Fourth Embodiment

Figure 26:
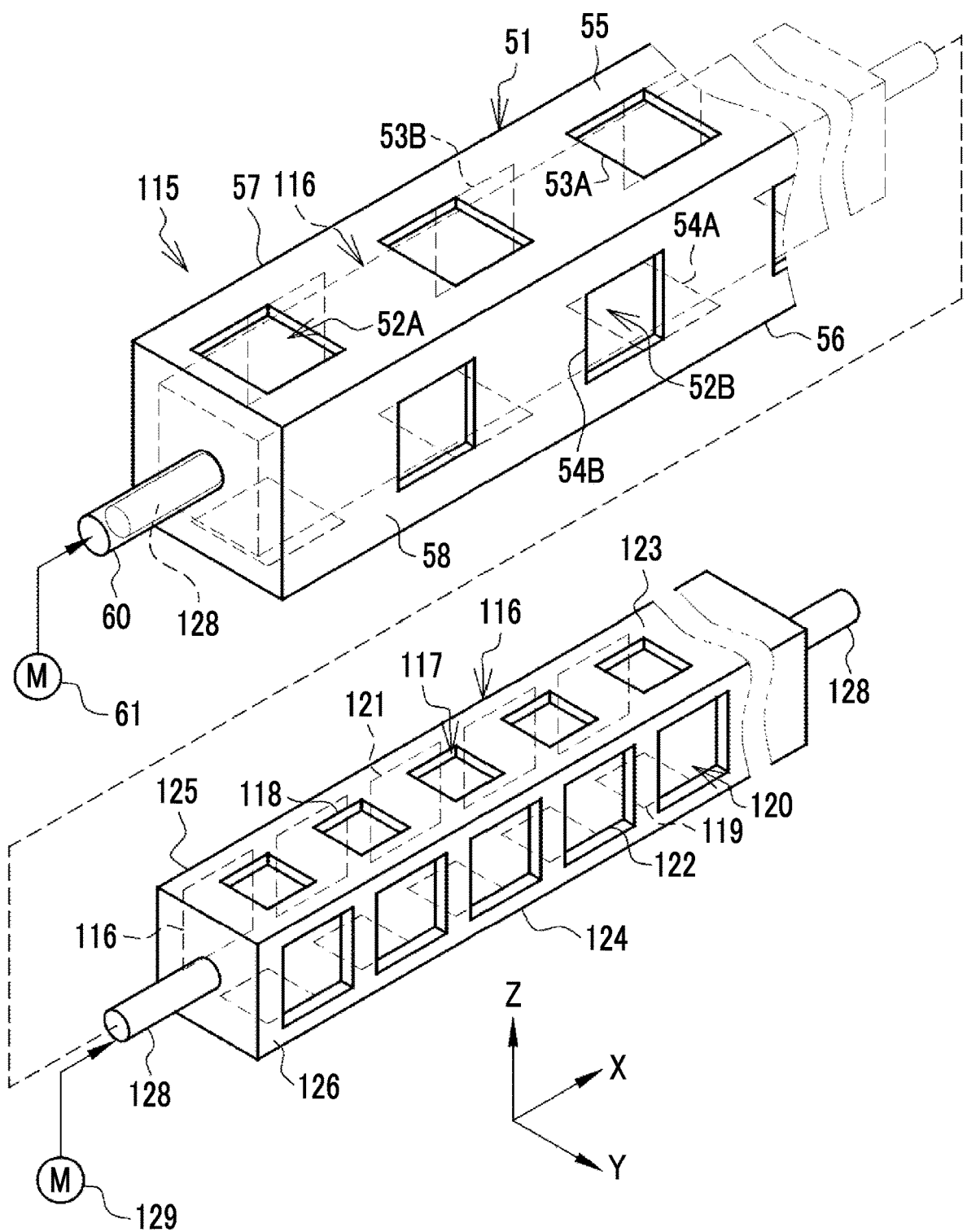
FIG. 26 is a diagram illustrating an irradiation field limiter in which a second rotating member is provided in a first rotating member.

In a fourth embodiment illustrated in FIGS. 26 and 27, an irradiation field limiter 115 in which a second rotating member 116 is disposed in a first rotating member 51 is used.

In FIG. 26, similarly to the first rotating member 51, the outward appearance of the second rotating member 116 is a square prism that is long in the X direction and has a square shape in a cross-sectional view taken along the Y direction. The second rotating member 116 has a size that is slightly smaller than the size of the first rotating member 51 and is disposed in the first rotating member 51. That is, the irradiation field limiter 115 has a nested structure. Similarly to the first rotating member 51, the second rotating member 116 is hollow and is made of a material shielding the radiation 37, such as lead.

A total of 15 second irradiation opening portions 117 whose number is equal to the number of radiation tubes 27 are formed in the second rotating member 116 along the X direction. The second irradiation opening portion 117 is configured by a pair of a first opening 118 and a second opening 119 and defines the irradiation field of the radiation 37 (see (A) of FIG. 27). Further, a total of 15 opening portions 120 whose number is equal to the number of radiation tubes 27 are formed in the second rotating member 116 along the X direction. The opening portion 120 is configured by a pair of a first opening 121 and a second opening 122. Unlike the second irradiation opening portion 117, the opening portion 120 does not define the irradiation field of the radiation 37 (see (B) of FIG. 27). The openings 118, 119, 121, and 122 are formed so as to surround the second rotating member 116 in a circumferential direction.

The first opening 118 and the second opening 119 forming the second irradiation opening portion 117 are formed in a rectangular first surface 123 and a rectangular second surface 124 of the second rotating member 116 at positions that face to each other in the irradiation direction of the radiation 37, respectively. The first opening 121 and the second opening 122 forming the opening portion 120 are formed at substantially the same positions as the first opening 118 and the second opening 119 in third and fourth surfaces 125 and 126 of the second rotating member 116 which have a rectangular shape and are opposite to each other, respectively. The first opening 118 and the second opening 119 forming one second irradiation opening portion 117 have the same size. In addition, the first opening 121 and the second opening 122 forming one opening portion 120 have the same size. The first opening 118 and the second opening 119 have a size that is slightly smaller than the size of the first opening 53 and the second opening 54 of the first irradiation opening portion 52 in the first rotating member 51. In contrast, the first opening 121 and the second opening 122 have substantially the same size as the first opening 53 and the second opening 54.

A pair of rotating shafts 128 parallel to the X direction are attached to the centers of both side surfaces of the second rotating member 116 which are opposite to each other in the X direction. A motor 129 is connected to the rotating shaft 128. The second rotating member 116 is rotated about the rotating shaft 128 by the operation of the motor 129. That is, the second rotating member 116 is rotated in the first rotating member 51 independently of the first rotating member 51.

As illustrated in FIG. 27, the second rotating member 116 is rotated to two rotation positions, that is, a first rotation position ((A) of FIG. 27) and a second rotation position ((B) of FIG. 27), similarly to the first rotating member 51. At the first rotation position illustrated in (A) of FIG. 27, the first surface 123 faces the radiation tubes 27, the second surface 124 faces the radiation detector 26, and the second irradiation opening portions 117 face the radiation tubes 27. In contrast, the second rotation position illustrated in (B) of FIG. 27 is a position which is rotated by 90° from the first rotation position and where the third surface 125 faces the radiation tubes 27, the fourth surface 126 faces the radiation detector 26, and the opening portions 120 face the radiation tubes 27.

At the first rotation position, the irradiation field is defined by the second opening 119 of the second irradiation opening portion 117 in the second rotating member 116. In contrast, at the second rotation position, the irradiation opening is defined by the second opening 54 of the first irradiation opening portion 52 in the first rotating member 51. As described above, the second opening 119 of the second irradiation opening portion 117 has a size that is slightly smaller than the size of the second opening 54 of the first irradiation opening portion 52. Therefore, the size of the irradiation field at the second rotation position is larger than that at the first rotation position.

As described above, in the fourth embodiment, the irradiation field limiter 115 in which the second rotating member 116 that is rotated about the rotating shaft 128 parallel to the X direction independently of the first rotating member 51 is provided is used. The second rotating member 116 has the second irradiation opening portion 117 having a size different from that of the first irradiation opening portion 52. Therefore, the size of the irradiation field can be changed by rotating the second rotating member 116 as illustrated in FIG. 27 while effectively utilizing the space inside the first rotating member 51.

The second rotating member 116 may be divided into two rotating members such as the first rotating members 51_1 and 51_2 according to the second embodiment. Further, the first opening 118 and the second opening 119 of the second irradiation opening portion 117 in the second rotating member 116 may have different sizes like the first opening 102 and the second opening 103 according to the third embodiment, Fifth Embodiment In a fifth embodiment illustrated in FIGS. 28 to 30, an irradiation field limiter 130 in which a visible light emitting unit 131 is disposed in a first rotating member 132 is used.

Figure 28:
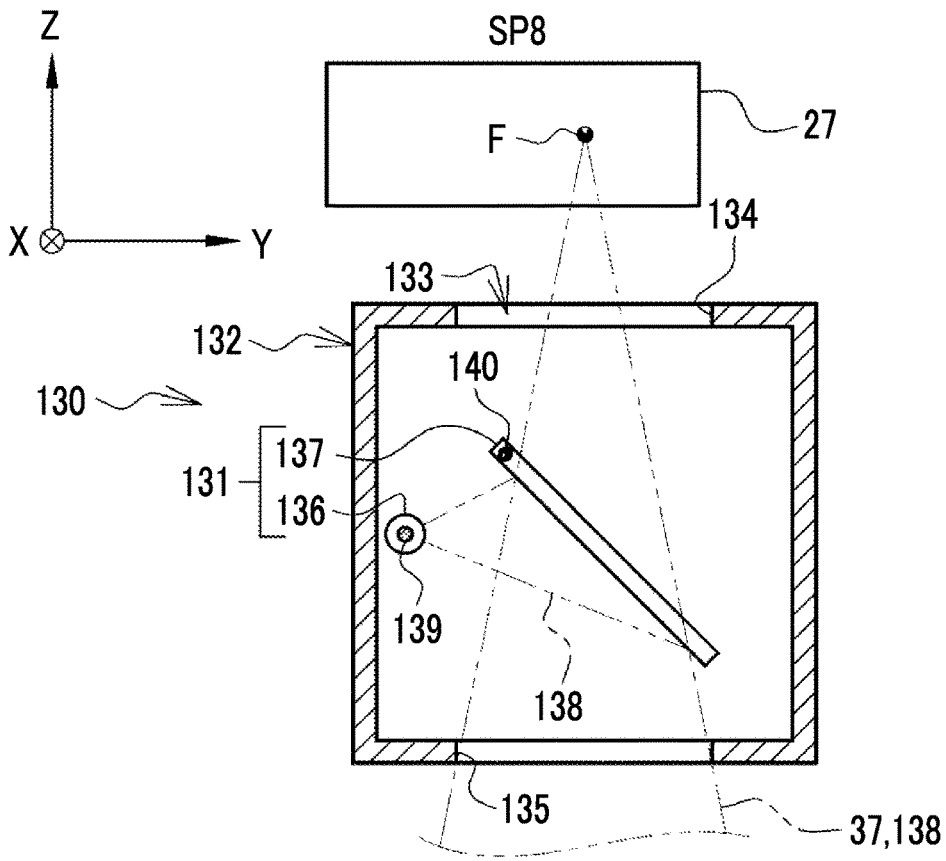
FIG. 28 is a partial cross-sectional view illustrating an irradiation field limiter in which a visible light emitting unit is provided in a first rotating member.
Figure 29:
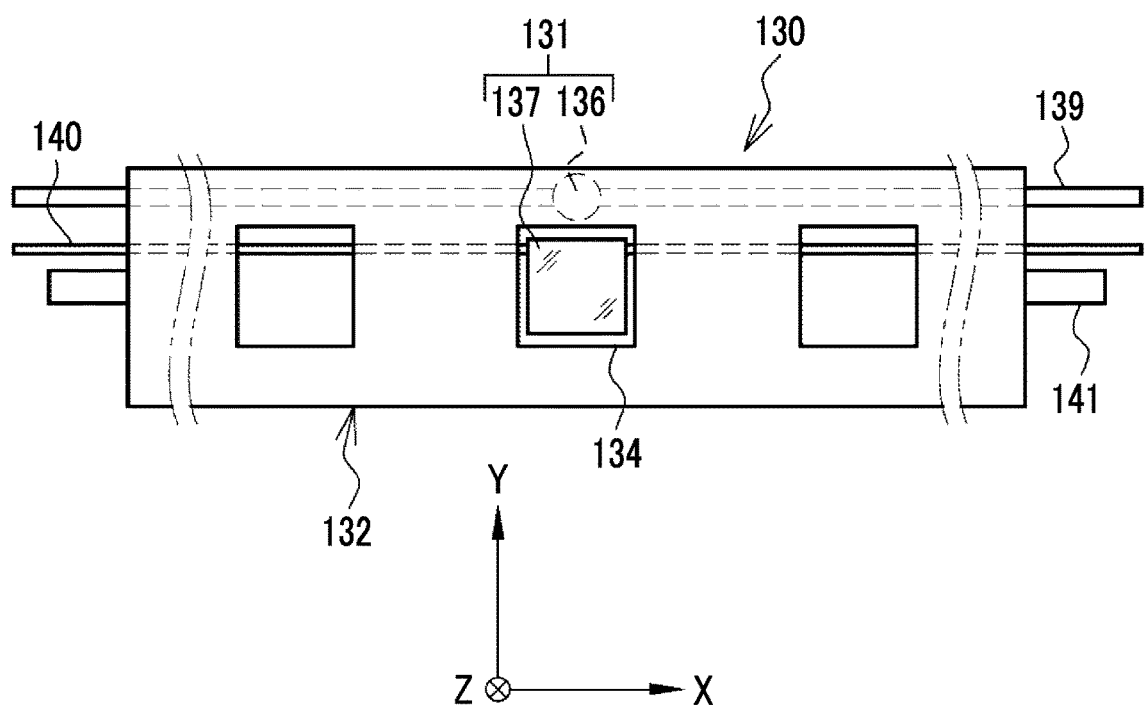
FIG. 29 is a plan view illustrating the irradiation field limiter in which the visible light emitting unit is provided in the first rotating member.

In FIGS. 28 to 30, the irradiation field limiter 130 has a configuration in which the visible light emitting unit 131 is disposed in the first rotating member 132. The visible light emitting unit 131 is disposed, for example, immediately below the radiation tube 27 at the position SP8. A first irradiation opening portion 133 of the first rotating member 132 faces the radiation tube 27 at the position SP8. The first irradiation opening portion 133 is configured by a pair of a first opening 134 and a second opening 135.

The visible light emitting unit 131 has a lamp 136 and a mirror 137. The lamp 136 emits, for example, orange visible light 138 to the mirror 137. The mirror 137 transmits the radiation 37 from the radiation tube 27 and reflects the visible light 138 from the lamp 136. For example, the mirror 137 is formed by depositing an aluminum film on an acrylic plate. The visible light 138 reflected by the mirror 137 is emitted to the radiation detector 26 through the second opening 135.

The lamp 136 is attached to an attachment rod 139 that extends in the X direction. Similarly, the mirror 137 is attached to an attachment rod 140 that extends in the X direction. The attachment rods 139 and 140 are disposed at positions that do not interfere with the radiation 37. The attachment rods 139 and 140 pass through the first rotating member 132 and are fixed to the inner wall surface of the radiation source accommodation portion 22. Therefore, the lamp 136 and the mirror 137 do not follow the first rotating member 132. That is, the positional relationship between the radiation tube 27 and the visible light emitting unit 131 does not change.

As illustrated in FIG. 30, a cutout portion 145 is formed in the side surface of the first rotating member 132 to which a rotating shaft 141 is attached. The cutout portion 145 is provided to prevent the rotation of the first rotating member 132 from being hindered by the attachment rods 139 and 140. (A) of FIG. 30 illustrates a case in which the first rotating member 132 is at the first rotation position and (B) of FIG. 30 illustrates a case in which the first rotating member 132 is rotated by 90° from the first rotation position and is at the second rotation position.

As such, in the fifth embodiment, the irradiation field limiter 130 in which the visible light emitting unit 131 that emits the visible light 138 indicating the irradiation field is disposed in the first rotating member 132 is used. Therefore, it is possible to inform the operator of the irradiation field for imaging through the first rotating member 132 while effectively utilizing the space inside the first rotating member 132.

Sixth Embodiment

Figure 31:
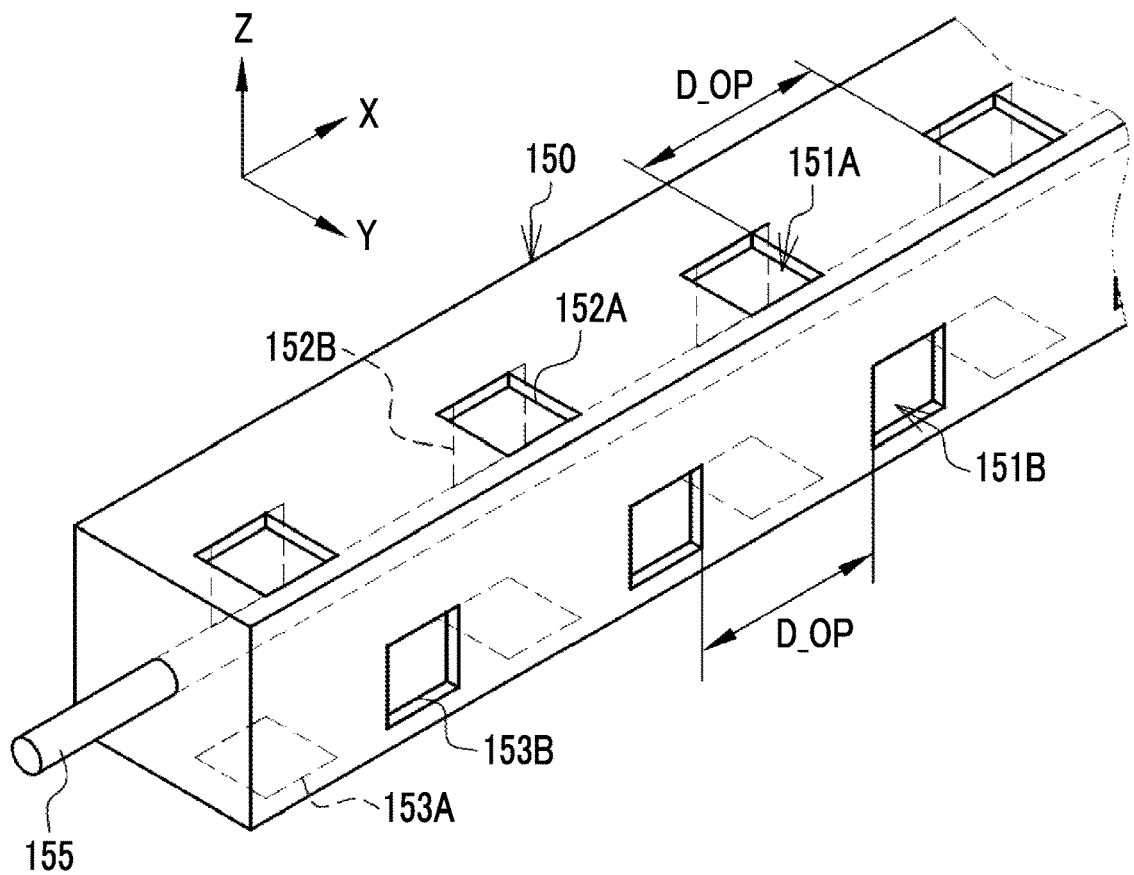
FIG. 31 is a perspective view illustrating a first rotating member to which a rotating shaft is attached so as to be offset.
Figure 32:
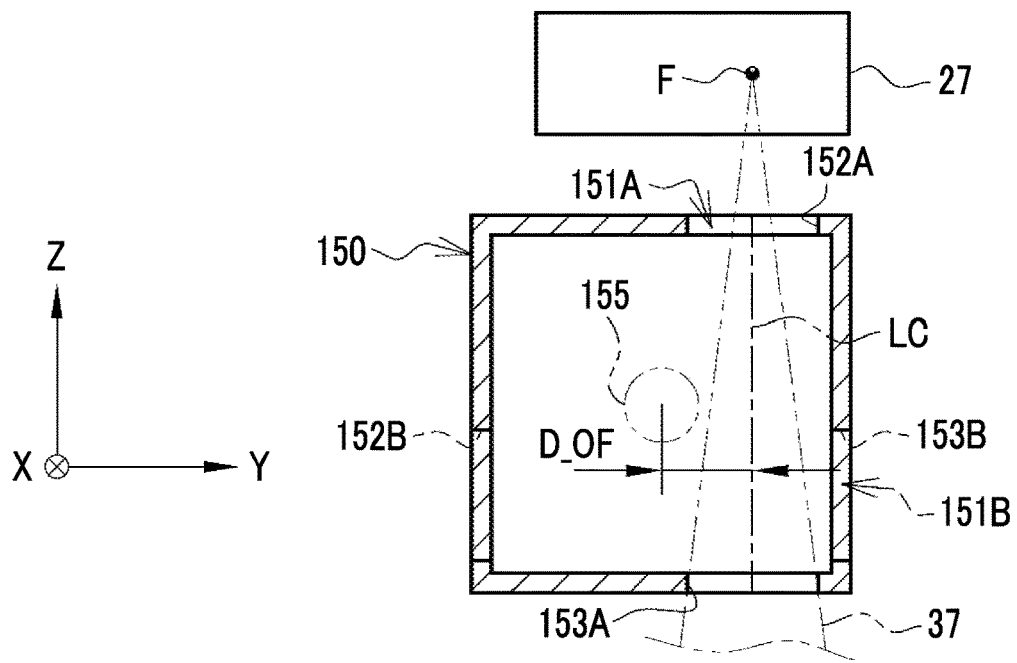
FIG. 32 is a partial cross-sectional view illustrating the first rotating member to which the rotating shaft that is attached so as to be offset.

In a sixth embodiment illustrated in FIGS. 31 and 32, a rotating shaft 155 is offset.

In FIG. 31, a first rotating member 150 has first irradiation opening portions 151A and 151B. The first irradiation opening portion 151A is configured by a pair of a first opening 152A and a second opening 153A. The first irradiation opening portion 151B is configured by a pair of a first opening 152B and a second opening 153B. The first opening 152A and the second opening 153A are formed in two opposite rectangular surfaces of the first rotating member 150 so as to be biased to one side. Similarly, the first opening 152B and the second opening 153B are formed in two opposite rectangular surfaces of the first rotating member 150 so as to be biased to one side. In addition, adjacent first irradiation opening portions 151A are arranged at an interval D_OP that is equal to an interval of one radiation tube 27. This holds for adjacent first irradiation opening portions 151B.

The rotating shaft 155 parallel to the X direction is attached to the first rotating member 150. The rotating shaft 155 extends from the center of one side surface of the first rotating member 150 which is orthogonal to the X direction to the center of the other opposite side surface and protrudes from both side surfaces.

As illustrated in FIG. 32, the rotating shaft 155 is offset from the centers of the first opening 152 and the second opening 153 (the first opening 152A and the second opening 153A are illustrated in FIG. 32) in a plan view from the X direction. Specifically, the rotating shaft 155 is offset from a line LC connecting the centers of the first opening 152 and the second opening 153 by the interval D_OF. The interval D_OF is a distance that does not interfere with the radiation 37 which is incident through the first opening 152 and exits from the second opening 153.

As such, in the sixth embodiment, the rotating shaft 155 of the first rotating member 150 is offset from the centers of the first opening 152 and the second opening 153 in a plan view from the X direction. Therefore, the rotating shaft 155 can be configured to pass through the first rotating member 150. In a case in which the rotating shaft 155 can be configured to pass through the first rotating member 150, it is possible to attach a component, such as the visible light emitting unit 131 according to the fifth embodiment, to the rotating shaft 155 in the first rotating member 150 and to increase flexibility in design.

In each of the above-described embodiments, the first rotating member having a square shape in a cross-sectional view taken along the Y direction is given as an example. However, the present disclosure is not limited thereto.

Figure 33:
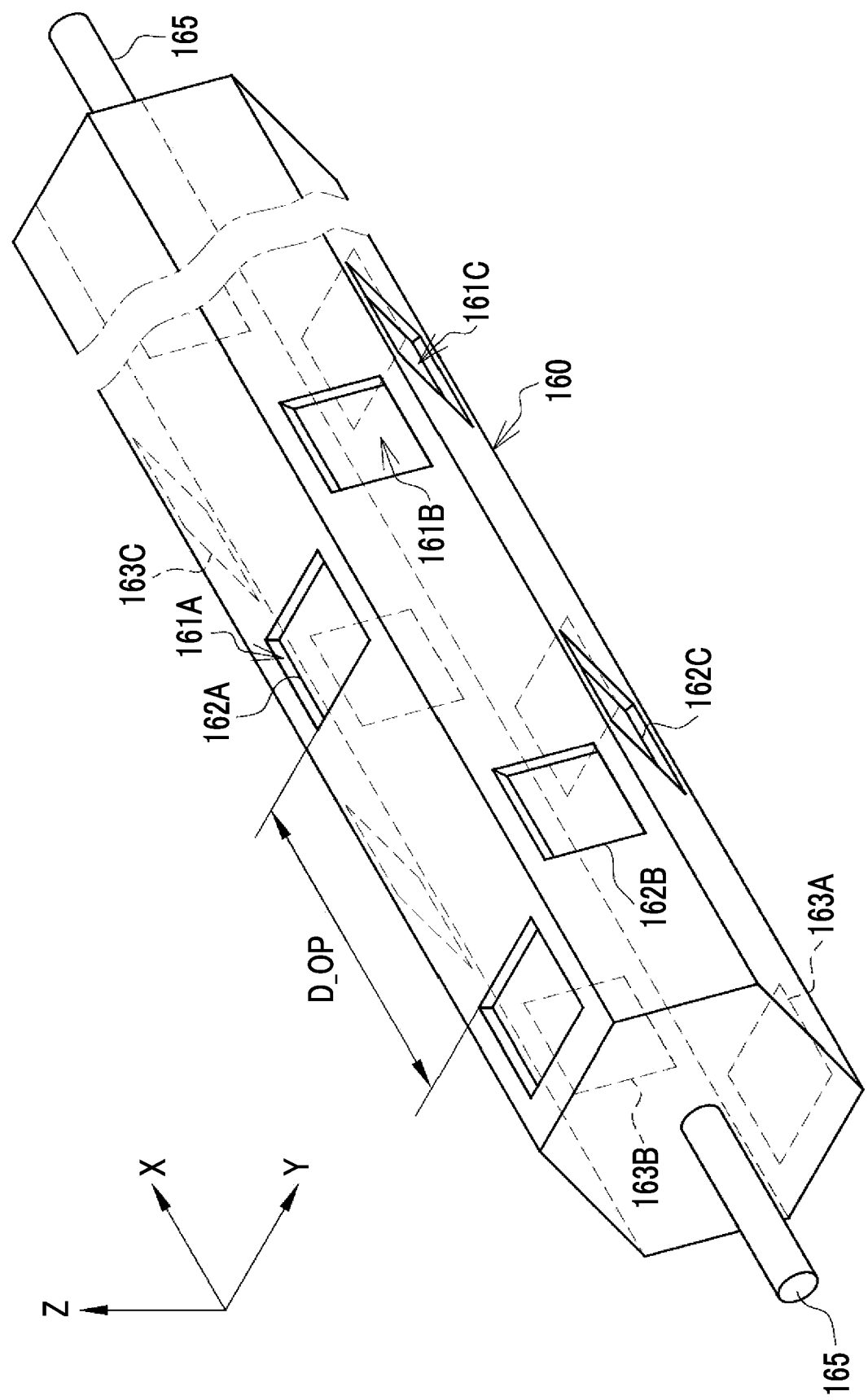
FIG. 33 is a perspective view illustrating a first rotating member having a regular hexagonal shape in a cross-sectional view taken along the lateral direction.

A first rotating member 160 illustrated in FIG. 33 has a regular hexagonal shape (N=6) in a cross-sectional view taken along the Y direction. The first rotating member 160 has first irradiation opening portions 161A, 161B, and 161C. The first irradiation opening portion 161A is configured by a pair of a first opening 162A and a second opening 163A. The first irradiation opening portion 161B is configured by a pair of a first opening 162B and a second opening 163B. The first irradiation opening portion 161C is configured by a pair of a first opening 162C and a second opening 163C. Each of the pairs of the first opening 162A and the second opening 163A, the first opening 162B and the second opening 163B, and the first opening 162C and the second opening 163C is formed in two opposite rectangular surfaces of the first rotating member 160 at positions that face each other in the irradiation direction of the radiation 37.

Adjacent first irradiation opening portions 161A are separated by an interval D_OP which is nearly equal to an interval of two radiation tubes 27. This holds for adjacent first irradiation opening portions 161B and adjacent first irradiation opening portions 161C, which is not illustrated.

A pair of rotating shafts 165 parallel to the X direction are attached to the centers of both side surfaces of the first rotating member 160 which are opposite to each other in the X direction. The first rotating member 160 is rotated about the rotating shaft 165 by the operation of a motor (not illustrated) that is attached to the rotating shaft 165.

Figure 34:
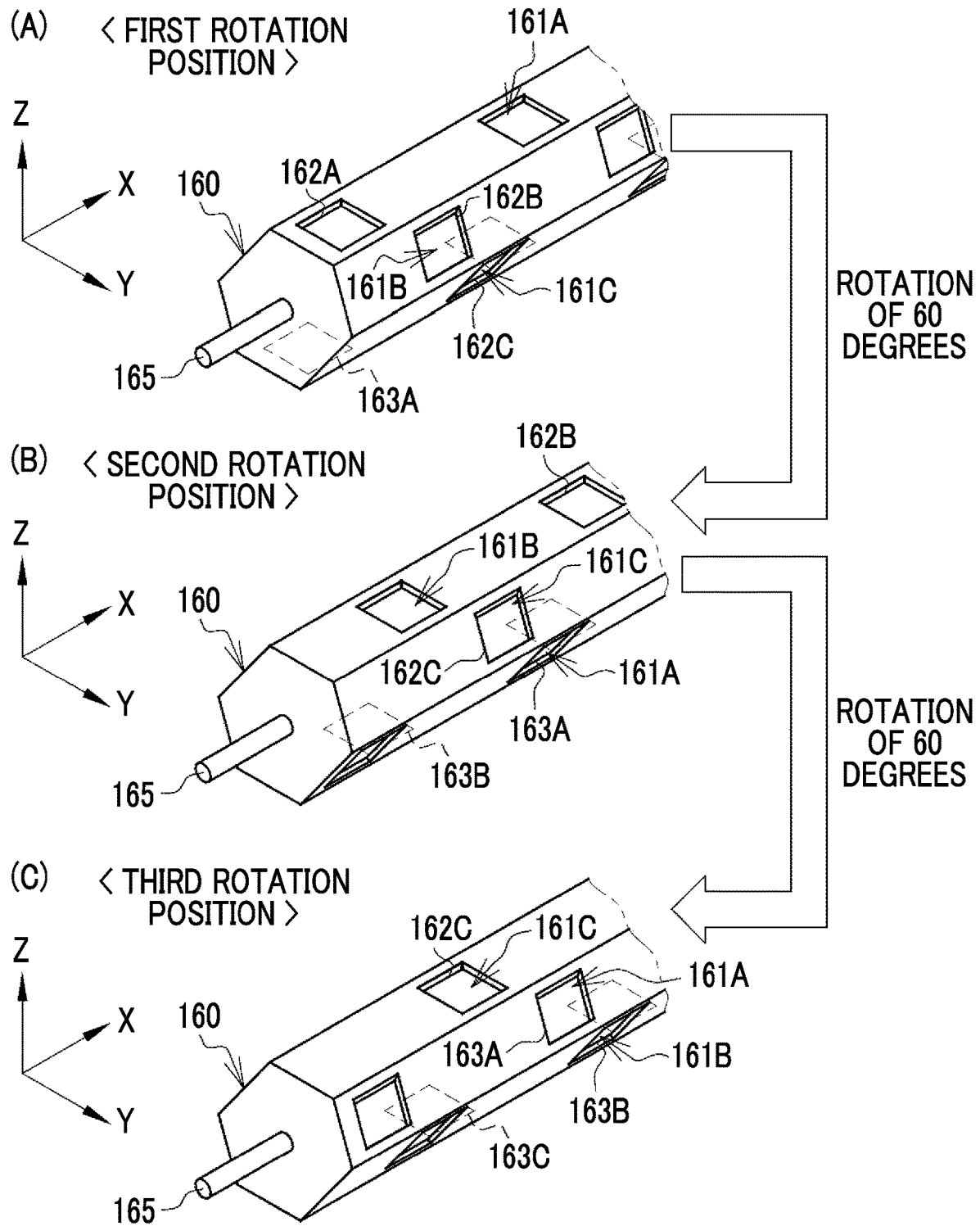
FIG. 34 is a diagram illustrating the first rotating member at each rotation position. (A) of FIG. 34 illustrates a first rotation position, (B) of FIG. 34 illustrates a second rotation position, and (C) of FIG. 34 illustrates a third rotation position.

As illustrated in FIG. 34, the first rotating member 160 is rotated to three rotation positions, that is, a first rotation position ((A) of FIG. 34), a second rotation position ((B) of FIG. 34), and a third rotation position ((C) of FIG. 34). At the first rotation position illustrated in (A) of FIG. 34, the first irradiation opening portion 161A faces the radiation tube 27. The second rotation position illustrated in (B) of FIG. 34 is a position which is rotated by 60° (=360°/6) from the first rotation position and where the first irradiation opening portion 161B faces the radiation tube 27. The third rotation position illustrated in (C) of FIG. 34 is a position which is rotated by 60° from the second rotation position and where the first irradiation opening portion 161C faces the radiation tube 27. At the first rotation position, the second rotation position, and the third rotation position, the first irradiation opening portion 161A, the first irradiation opening portion 161B, and the first irradiation opening portion 161C deviate from each other in the X direction so as to face different radiation tubes 27 in the irradiation direction of the radiation 37.

FIG. 35 illustrates a table 168 showing the radiation tube IDs of the radiation tubes 27 that emit the radiation 37 at each of the first rotation position, the second rotation position, and the third rotation position. At the first rotation position, the first irradiation opening portions 161A define the irradiation field of the radiation 37 emitted from the radiation tubes 27 having the radiation tube IDs RT01, RT04, RT07, RT10, and RT13. That is, the radiation tubes 27 having the radiation tube IDs RT01, RT04, RT07, RT10, and RT13 are an example of "the first radiation tubes facing the first irradiation opening portions at the first rotation position" according to the technique of the present disclosure. In addition, the radiation tubes 27 having the radiation tube IDs RT02, RT03, RT05, RT06, RT08, RT09, RT11, RT12, RT14, and RT15 are an example of "the second radiation tubes that do not face the first irradiation opening portions and are other than the first radiation tubes facing the first irradiation opening portions at the first rotation position" according to the technique of the present disclosure. In FIG. 35, the radiation tubes 27 having the radiation tube IDs RT03, RT06, RT09, RT12, and RT15 which emit the radiation 37 at the third rotation position are referred to as third radiation tubes for convenience.

At the second rotation position, the first irradiation opening portions 161B define the irradiation field of the radiation 37 emitted from the radiation tubes 27 having the radiation tube IDs RT02, RT05, RT08, RT11, and RT14. At the third rotation position, the first irradiation opening portions 161C define the irradiation field of the radiation 37 emitted from the radiation tubes 27 having the radiation tube IDs RT03, RT06, RT09, RT12, and RT15.

The first rotating member 160 may be divided into two rotating members such as the first rotating members 51_1 and 51_2 according to the second embodiment. Further, the first opening 162 and the second opening 163 of the first irradiation opening portion 161 in the first rotating member 160 may have different sizes like the first opening 102 and the second opening 103 according to the third embodiment. Further, the first opening 162 and the second opening 163 may not be formed in one of the two opposite rectangular surfaces of the first rotating member 160.

Figure 36:
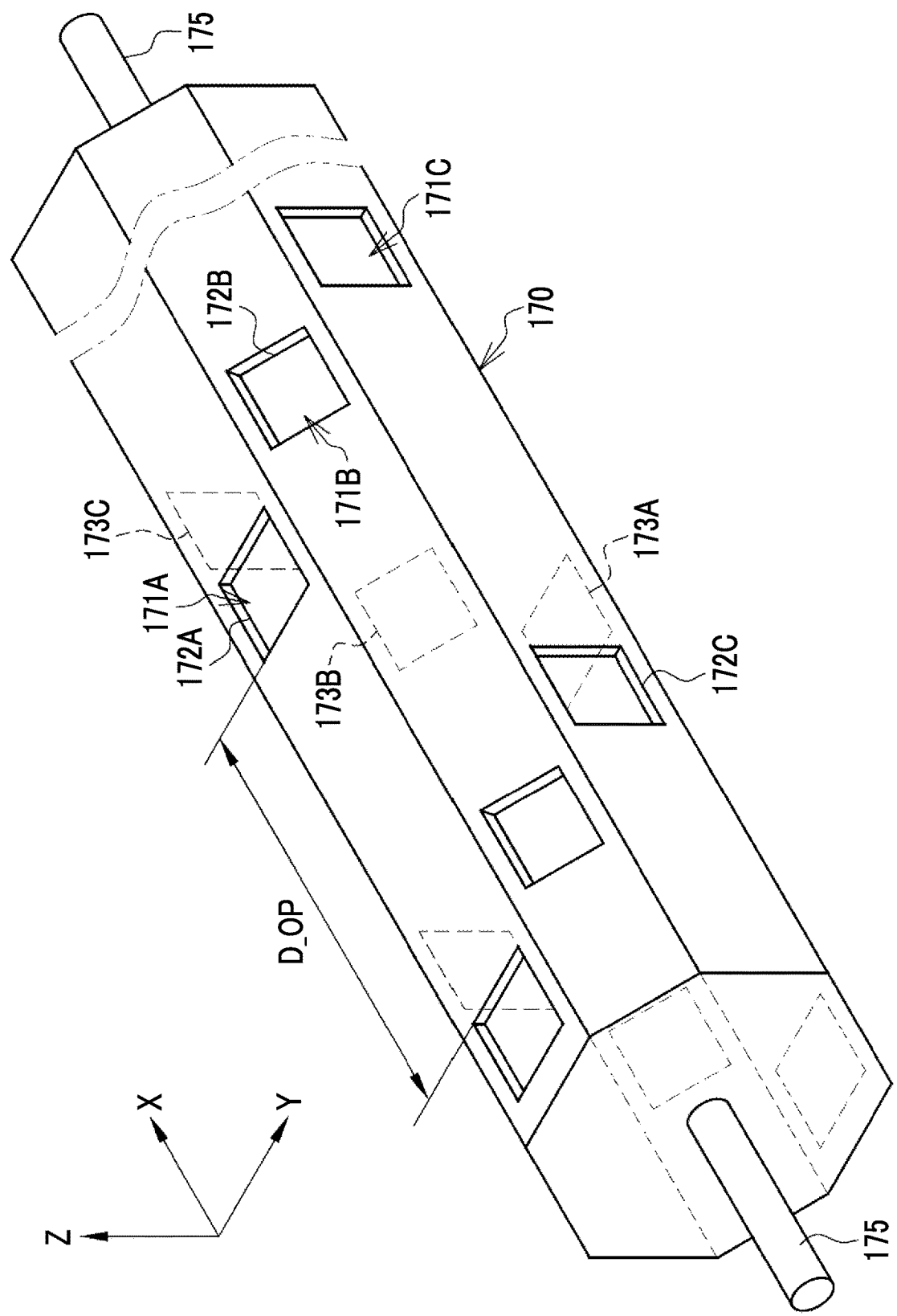
FIG. 36 is a perspective view illustrating a first rotating member having a regular octagonal shape in a cross-sectional view taken along the lateral direction.

A first rotating member 170 illustrated in FIG. 36 has a regular octagonal shape (N=8) in a cross-sectional view taken along the Y direction. The first rotating member 170 has first irradiation opening portions 171A, 171B, 171C, and 171D (see, for example, (D) of FIG. 37 for the first irradiation opening portions 171D). The first irradiation opening portion 171A is configured by a pair of a first opening 172A and a second opening 173A. The first irradiation opening portion 171B is configured by a pair of a first opening 172B and a second opening 173B. The first irradiation opening portion 171C is configured by a pair of a first opening 172C and a second opening 173C. The first irradiation opening portion 171D is configured by a pair of a first opening 172D and a second opening 173D. Each of the pairs of the first opening 172A and the second opening 173A, the first opening 172B and the second opening 173B, the first opening 172C and the second opening 173C, and the first opening 172D and the second opening 173D is formed in two opposite rectangular surfaces of the first rotating member 170 at positions that face each other in the irradiation direction of the radiation 37.

Adjacent first irradiation opening portions 171A are separated by an interval D_OP which is nearly equal to an interval of three radiation tubes 27. This holds for adjacent first irradiation opening portions 171B, adjacent first irradiation opening portions 171C, and adjacent first irradiation opening portions 171D, which is not illustrated.

A pair of rotating shafts 175 parallel to the X direction are attached to the centers of both side surfaces of the first rotating member 170 which are opposite to each other in the X direction. The first rotating member 170 is rotated about the rotating shaft 175 by the operation of a motor (not illustrated) that is attached to the rotating shaft 175.

Figure 37:
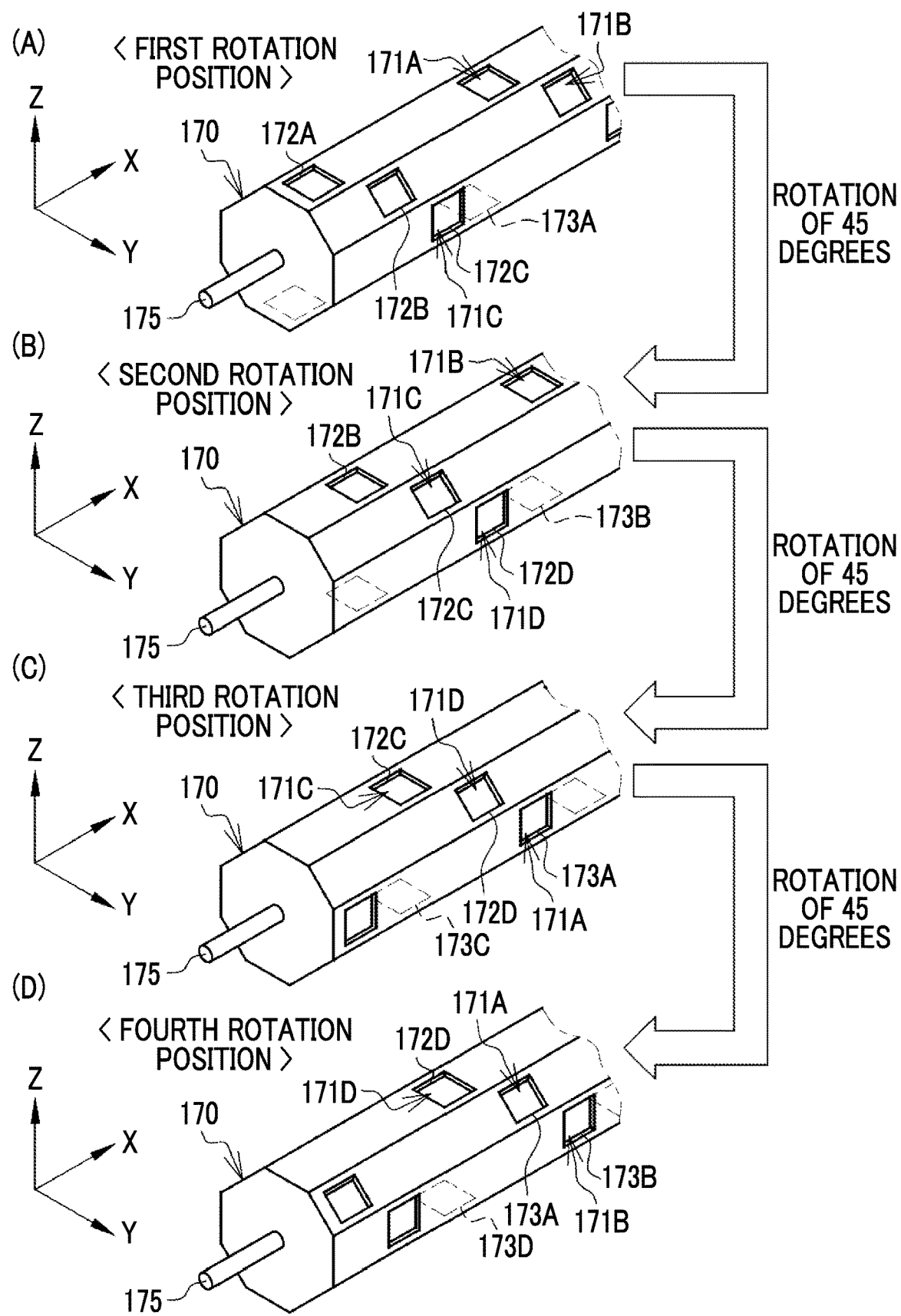
FIG. 37 is a diagram illustrating the first rotating member at each rotation position. (A) of FIG. 37 illustrates a first rotation position, (B) of FIG. 37 illustrates a second rotation position, (C) of FIG. 37 illustrates a third rotation position, and (D) of FIG. 37 illustrates a fourth rotation position.

As illustrated in FIG. 37, the first rotating member 170 is rotated to four rotation positions, that is, a first rotation position ((A) of FIG. 37), a second rotation position ((B) of FIG. 37), a third rotation position ((C) of FIG. 37), and a fourth rotation position ((D) of FIG. 37). At the first rotation position illustrated in (A) of FIG. 37, the first irradiation opening portion 171A faces the radiation tube 27. The second rotation position illustrated in (B) of FIG. 37 is a position which is rotated by 45° (=360°/8) from the first rotation position and where the first irradiation opening portion 171B faces the radiation tube 27. The third rotation position illustrated in (C) of FIG. 37 is a position which is rotated by 45° from the second rotation position and where the first irradiation opening portion 171C faces the radiation tube 27. The fourth rotation position illustrated in (D) of FIG. 37 is a position which is rotated by 45° from the third rotation position and where the first irradiation opening portion 171D faces the radiation tube 27. At the first rotation position, the second rotation position, the third rotation position, and the fourth rotation position, the first irradiation opening portion 171A, the first irradiation opening portion 171B, the first irradiation opening portion 171C, and the first irradiation opening portion 171D deviate from each other in the X direction so as to face different radiation tubes 27 in the irradiation direction of the radiation 37.

FIG. 38 is a table 178 showing the radiation tube IDs of the radiation tubes 27 that emit the radiation 37 at each of the first rotation position, the second rotation position, the third rotation position, and the fourth rotation position. At the first rotation position, the first irradiation opening portions 171A define the irradiation field of the radiation 37 emitted from the radiation tubes 27 having the radiation tube IDs RT01, RT05, RT09, and RT13. That is, the radiation tubes 27 having the radiation tube IDs RT01, RT05, RT09, and RT13 are an example of "the first radiation tubes facing the first irradiation opening portions at the first rotation position"

according to the technique of the present disclosure. In addition, the radiation tubes 27 having the radiation tube IDs RT02 to RT04, RT06 to RT08, RT10 to RT12, RT14, and RT15 are an example of "the second radiation tubes that do not face the first irradiation opening portions and are other than the first radiation tubes facing the first irradiation opening portions at the first rotation position" according to the technique of the present disclosure. In FIG. 38, similarly to FIG. 35, the radiation tubes 27 having the radiation tube IDs RT03, RT07, RT11, and RT15 which emit the radiation 37 at the third rotation position are referred to as third radiation tubes for convenience. Further, the radiation tubes 27 having the radiation tube IDs RT04, RT08, and RT12 which emit the radiation 37 at the fourth rotation position are referred to as fourth radiation tubes for convenience.

At the second rotation position, the first irradiation opening portions 171B define the irradiation field of the radiation 37 emitted from the radiation tubes 27 having the radiation tube IDs RT02, RT06, RT10, and RT14. At the third rotation position, the first irradiation opening portions 171C define the irradiation field of the radiation 37 emitted from the radiation tubes 27 having the radiation tube IDs RT03, RT07, RT11, and RT15. At the fourth rotation position, the first irradiation opening portions 171D define the irradiation field of the radiation 37 emitted from the radiation tubes 27 having the radiation tube IDs RT04, RT08, and RT12.

The first rotating member 170 may be divided into two rotating members such as the first rotating members 51_1 and 51_2 according to the second embodiment. Further, like the first opening 102 and the second opening 103 according to the third embodiment, the first opening 172 and the second opening 173 of the first irradiation opening portion 171 in the first rotating member 170 may have different sizes. Further, the first opening 172 and the second opening 173 may not be formed in one of two opposite rectangular surfaces of the first rotating member 170.

Figure 39:
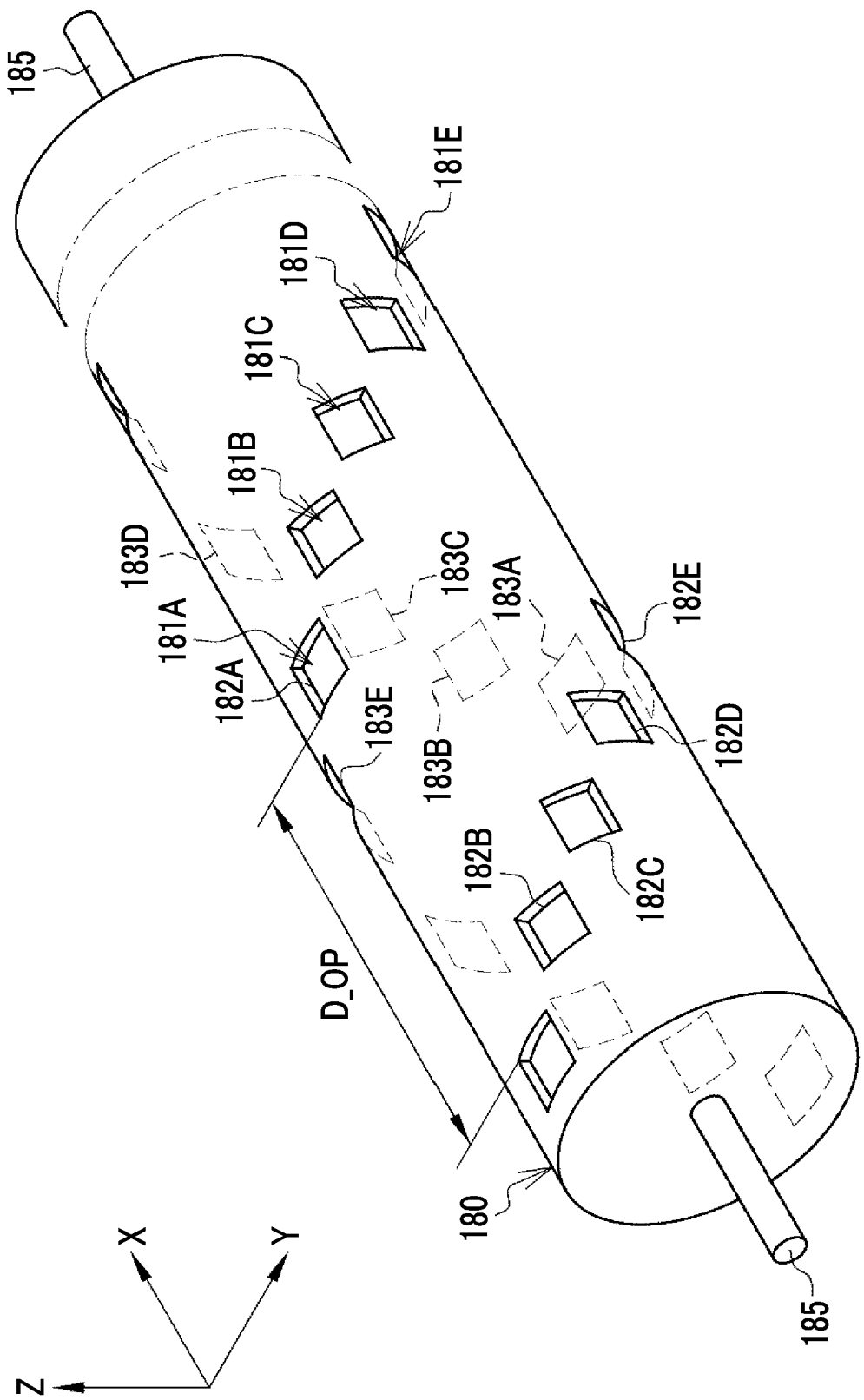
FIG. 39 is a perspective view illustrating a first rotating member having a circular shape in a cross-sectional view taken along the lateral direction.

A first rotating member 180 illustrated in FIG. 39 has a circular shape in a cross-sectional view taken along the Y direction. The first rotating member 180 has first irradiation opening portions 181A, 181B, 181C, 181D, and 181E. The first irradiation opening portion 181A is configured by a pair of a first opening 182A and a second opening 183A. The first irradiation opening portion 181B is configured by a pair of a first opening 182B and a second opening 183B. The first irradiation opening portion 181C is configured by a pair of a first opening 182C and a second opening 183C. The first irradiation opening portion 181D is configured by a pair of a first opening 182D and a second opening 183D. The first irradiation opening portion 181E is configured by a pair of a first opening 182E and a second opening 183E. The first opening 182A and the second opening 183A, the first opening 182B and the second opening 183B, the first opening 182C and the second opening 183C, the first opening 182D and the second opening 183D, and the first opening 182E and the second opening 183E are formed in the surface of the first rotating member 180 at positions that face each other in the irradiation direction of the radiation 37.

Adjacent first irradiation opening portions 181A are separated by an interval D_OP which is nearly equal to an interval of four radiation tubes 27. This holds for adjacent first irradiation opening portions 181B, adjacent first irradiation opening portions 181C, adjacent first irradiation opening portions 181D, and adjacent first irradiation opening portions 181E, which is not illustrated.

A pair of rotating shafts 185 parallel to the X direction are attached to the centers of both side surfaces of the first rotating member 180 which are opposite to each other in the X direction. The first rotating member 180 is rotated about the rotating shaft 185 by the operation of a motor (not illustrated) that is attached to the rotating shaft 185.

Figure 40:
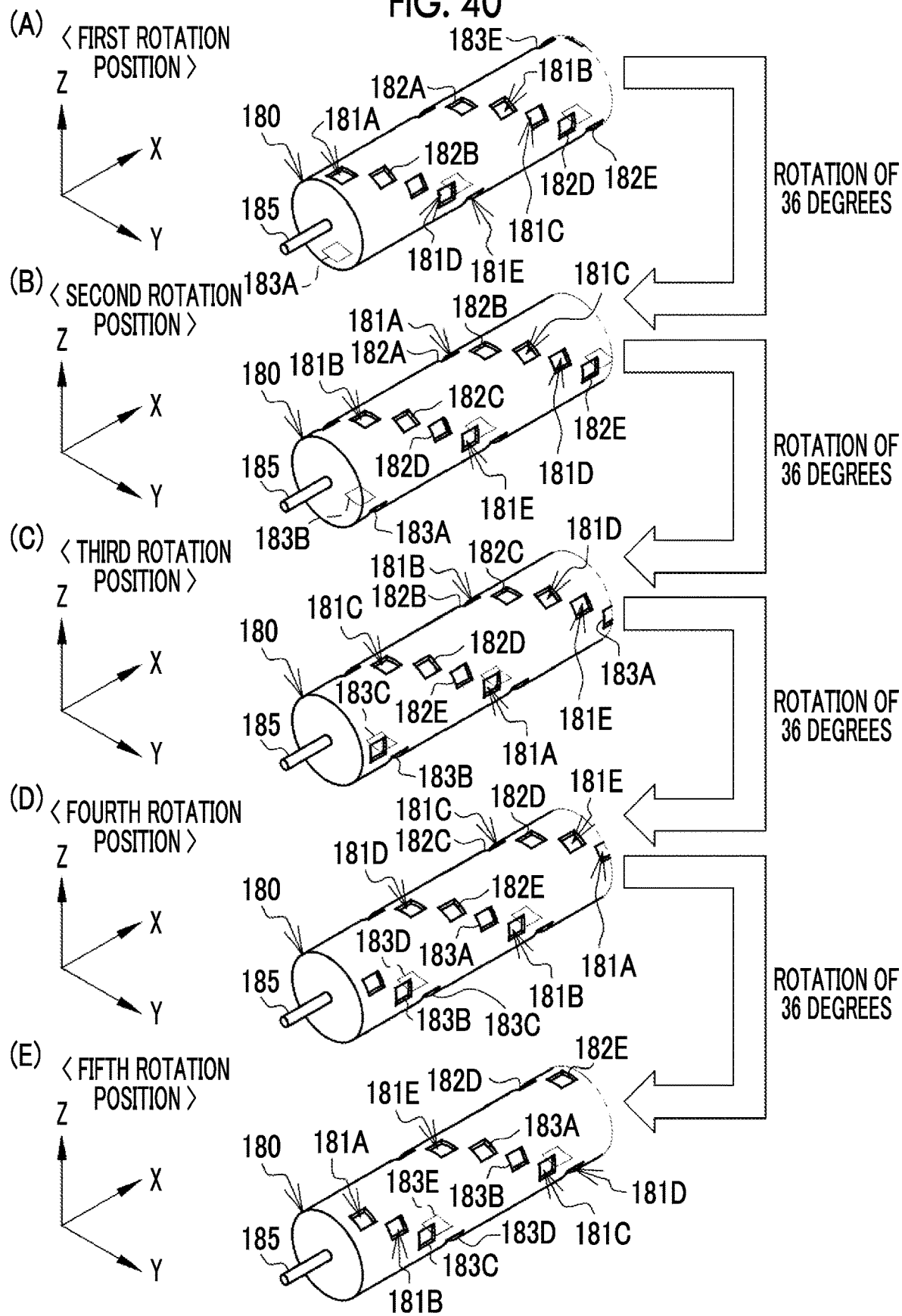
FIG. 40 is a diagram illustrating the first rotating member at each rotation position. (A) of FIG. 40 illustrates a first rotation position, (B) of FIG. 40 illustrates a second rotation position, (C) of FIG. 40 illustrates a third rotation position, (D) of FIG. 40 illustrates a fourth rotation position, and (E) of FIG. 40 illustrates a fifth rotation position.

As illustrated in FIG. 40, the first rotating member 180 is rotated to five rotation positions, that is, a first rotation position ((A) of FIG. 40), a second rotation position ((B) of FIG. 40), a third rotation position ((C) of FIG. 40), a fourth rotation position ((D) of FIG. 40), and a fifth rotation position ((E) of FIG. 40). At the first rotation position illustrated in (A) of FIG. 40, the first irradiation opening portion 181A faces the radiation tube 27. The second rotation position illustrated in (B) of FIG. 40 is a position which is rotated by 36° (=360°/10) from the first rotation position and where the first irradiation opening portion 181B faces the radiation tube 27. The third rotation position illustrated in (C) of FIG. 40 is a position which is rotated by 36° from the second rotation position and where the first irradiation opening portion 181C faces the radiation tube 27. The fourth rotation position illustrated in (D) of FIG. 40 is a position which is rotated by 36° from the third rotation position and where the first irradiation opening portion 181D faces the radiation tube 27. The fifth rotation position illustrated in (E) of FIG. 40 is a position which is rotated 36° from the fourth rotation position and where the first irradiation opening portion 181E faces the radiation tube 27. At the first rotation position, the second rotation position, the third rotation position, the fourth rotation position, and the fifth rotation position, the first irradiation opening portion 181A, the first irradiation opening portion 181B, the first irradiation opening portion 181C, the first irradiation opening portion 181D, and the first irradiation opening portion 181E deviate from each other in the X direction so as to face different radiation tubes 27 in the irradiation direction of the radiation 37.

FIG. 41 illustrates a table 188 showing the radiation tube IDs of the radiation tubes 27 that emit the radiation 37 at each of the first rotation position, the second rotation position, the third rotation position, the fourth rotation position, and the fifth rotation position. At the first rotation position, the first irradiation opening portions 181A define the irradiation field of the radiation 37 emitted from the radiation tubes 27 having the radiation tube IDs RT01, RT06, and RT11. That is, the radiation tubes 27 having the radiation tube IDs RT01, RT06, and RT11 are an example of the "first radiation tubes facing the first irradiation opening portions at the first rotation position" according to the technique of the present disclosure. Further, the radiation tubes 27 having the radiation tube IDs RT02 to RT05, RT07 to RT10, and RT12 to RT15 are an example of "the second radiation tubes that do not face the first irradiation opening portions and are other than the first radiation tubes facing the first irradiation opening portions at the first rotation position" according to the technique of the present disclosure. In FIG. 41, similarly to FIGS. 35 and 38, the radiation tubes 27 having the radiation tube IDs RT03, RT08, and RT13 which emit the radiation 37 at the third rotation position are referred to as third radiation tubes for convenience. Further, the radiation tubes 27 having the radiation tube IDs RT04, RT09, and RT14 which emits the radiation 37 at the fourth rotation position are referred to as fourth radiation tubes for convenience. Furthermore, the radiation tubes 27 having the radiation tube IDs RT05, RT10, and RT15 which emits the radiation 37 at the fifth rotation position are referred to as fifth radiation tubes for convenience.

At the second rotation position, the first irradiation opening portions 181B define the irradiation field of the radiation 37 emitted from the radiation tubes 27 having the radiation tube IDs RT02, RT07, and RT12. At the third rotation position, the first irradiation opening portions 181C define the irradiation field of the radiation 37 emitted from the radiation tubes 27 having the radiation tube IDs RT03, RT08, and RT13. At the fourth rotation position, the first irradiation opening portions 181D define the irradiation field of the radiation 37 emitted from the radiation tubes 27 having the radiation tube IDs RT04, RT09, and RT14. At the fifth rotation position, the first irradiation opening portions 181E define the irradiation field of the radiation 37 emitted from the radiation tubes 27 having the radiation tube IDs RT05, RT10, and RT15.

The first rotating member 180 may be divided into two rotating members such as the first rotating members 51_1 and 51_2 according to the second embodiment. Further, like the first opening 102 and the second opening 103 according to the third embodiment, the first opening 182 and the second opening 183 of the first irradiation opening portion 181 in the first rotating member 180 may have different sizes.

Figure 42:
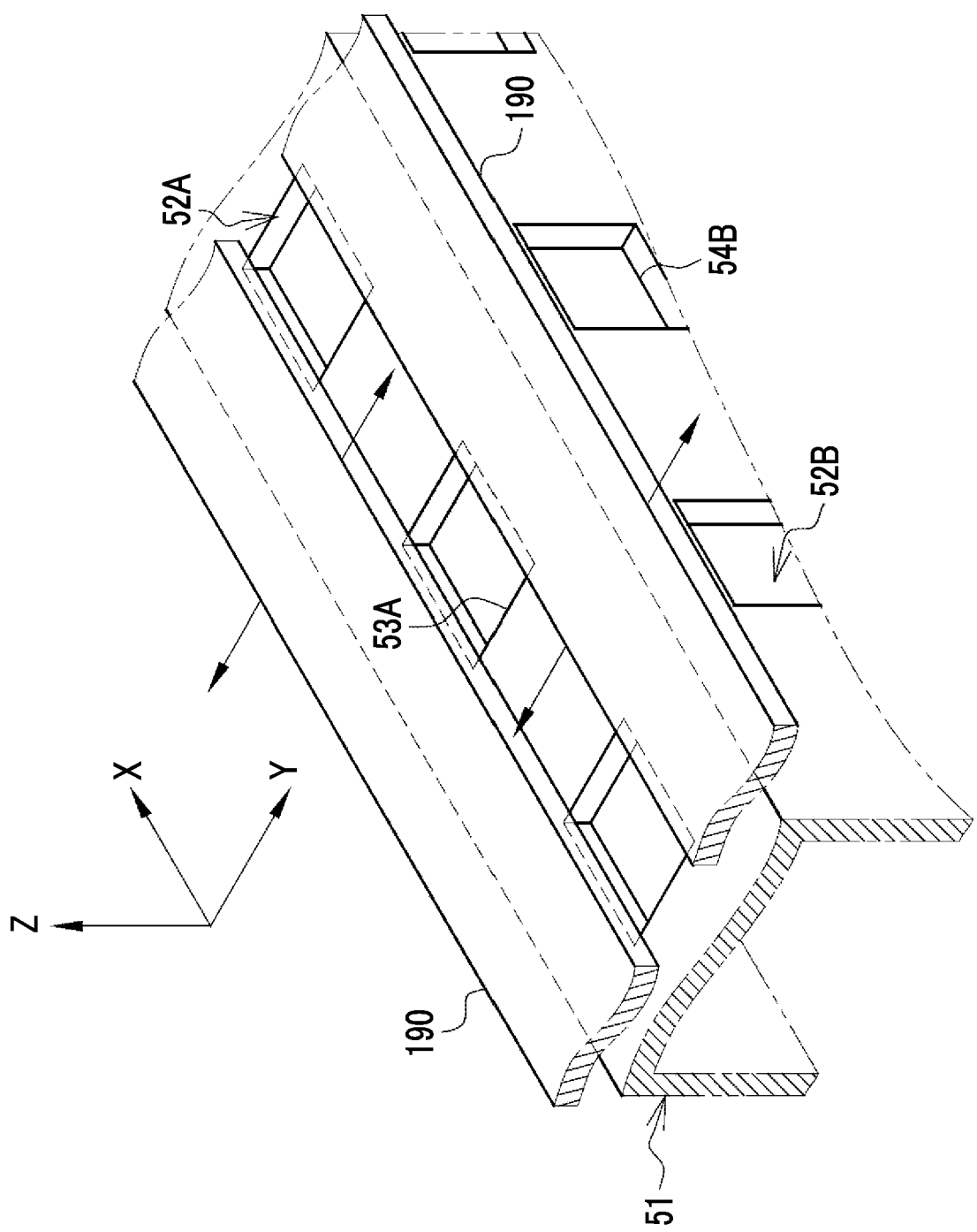
FIG. 42 is a perspective view illustrating an aspect in which the width of an opening in the Y direction is adjusted.
Figure 43:
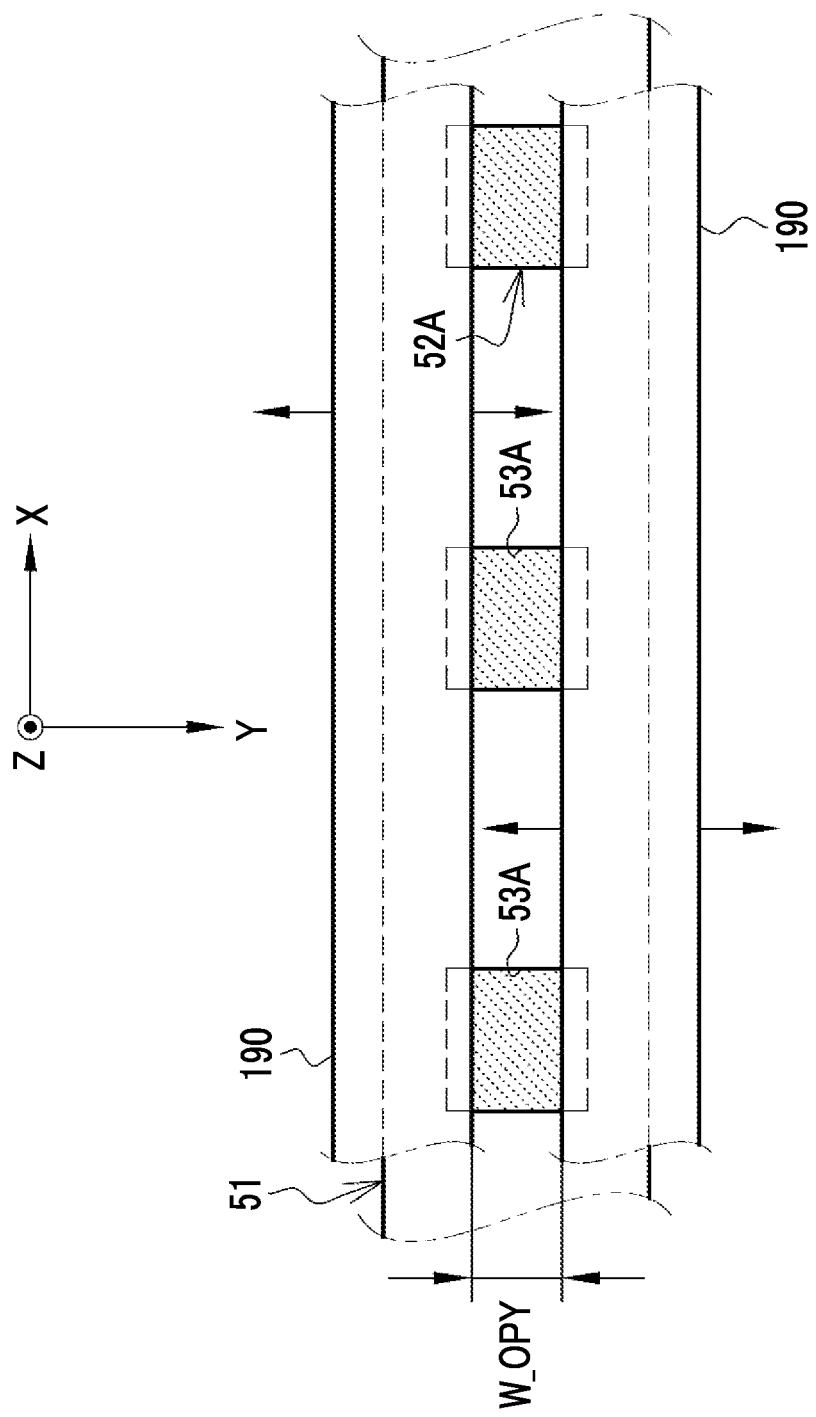
FIG. 43 is a plan view illustrating an aspect in which the width of the opening in the Y direction is adjusted.

As illustrated in FIGS. 42 and 43, the width of an opening in the Y direction which is a direction intersecting the arrangement direction of the radiation tubes 27 may be adjusted.

FIGS. 42 and 43 illustrate a case in which the first rotating member 51 according to the first embodiment is used. In FIGS. 42 and 43, a pair of adjustment members 190 are disposed above the first rotating member 51 so as to cover the first rotating member 51. The adjustment member 190 is a rectangular plate that is long in the X direction and has long sides arranged along the X direction. The adjustment member 190 can be reciprocated in the Y direction by a movement mechanism (not illustrated). As illustrated in FIG. 43, the adjustment members 190 are moved in the Y direction to adjust the widths W_OPY of a plurality of openings (the first openings 53A are illustrated in FIG. 43) at once as represented by hatching. The provision of the adjustment members 190 makes it possible to easily adjust the width W_OPY of the opening in the Y direction.

The application of the adjustment members 190 is not limited to the first rotating member 51 according to the first embodiment. For example, the adjustment members 190 may be provided in the first rotating members according to other embodiments to adjust the width W_OPY of the opening in the Y direction.

Figure 44:
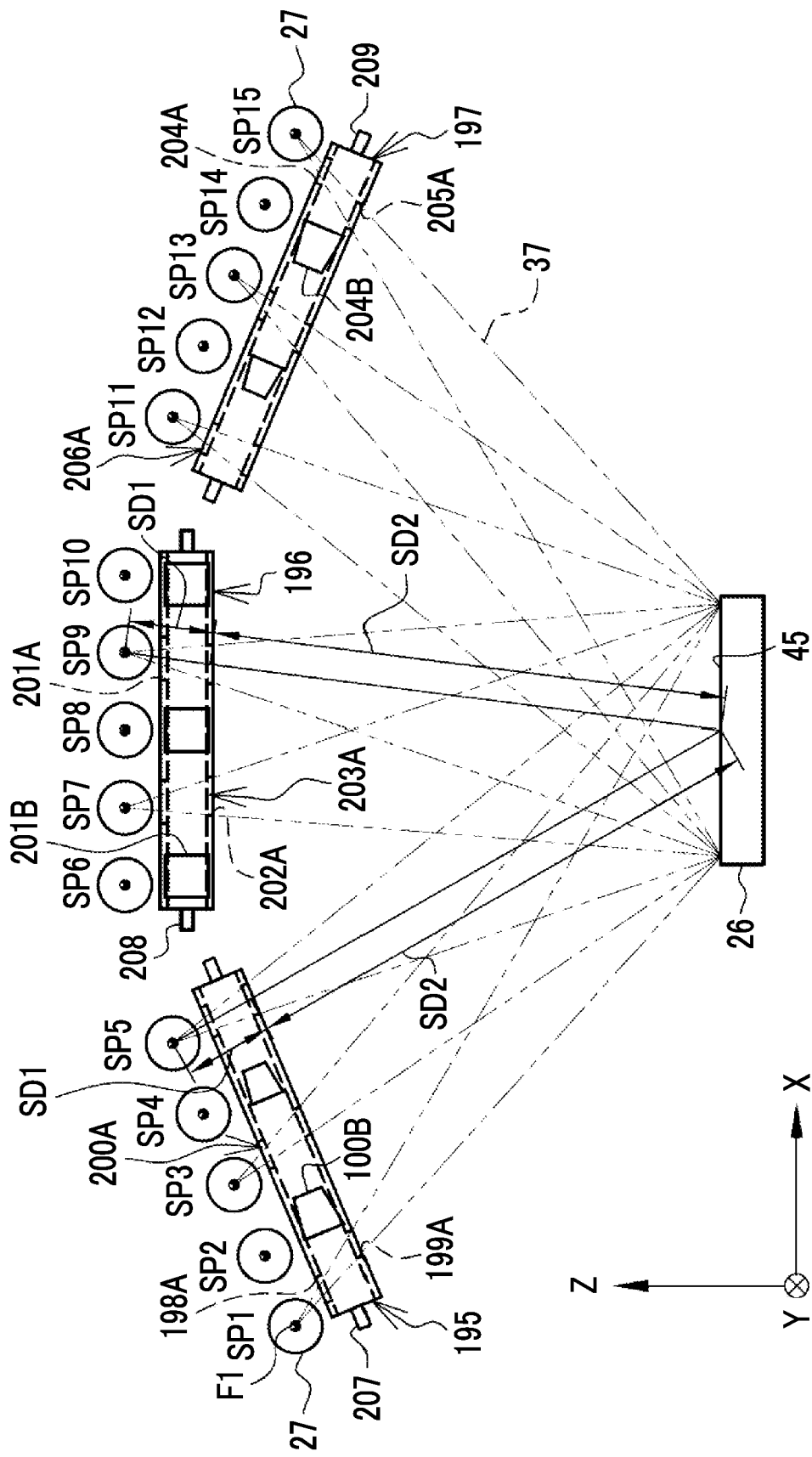
FIG. 44 is a diagram illustrating an example in which a plurality of radiation tubes are divided into a plurality of groups and the radiation tubes in the groups at the ends are disposed so as to be inclined at a predetermined angle with respect to an imaging surface.
Figure 45:
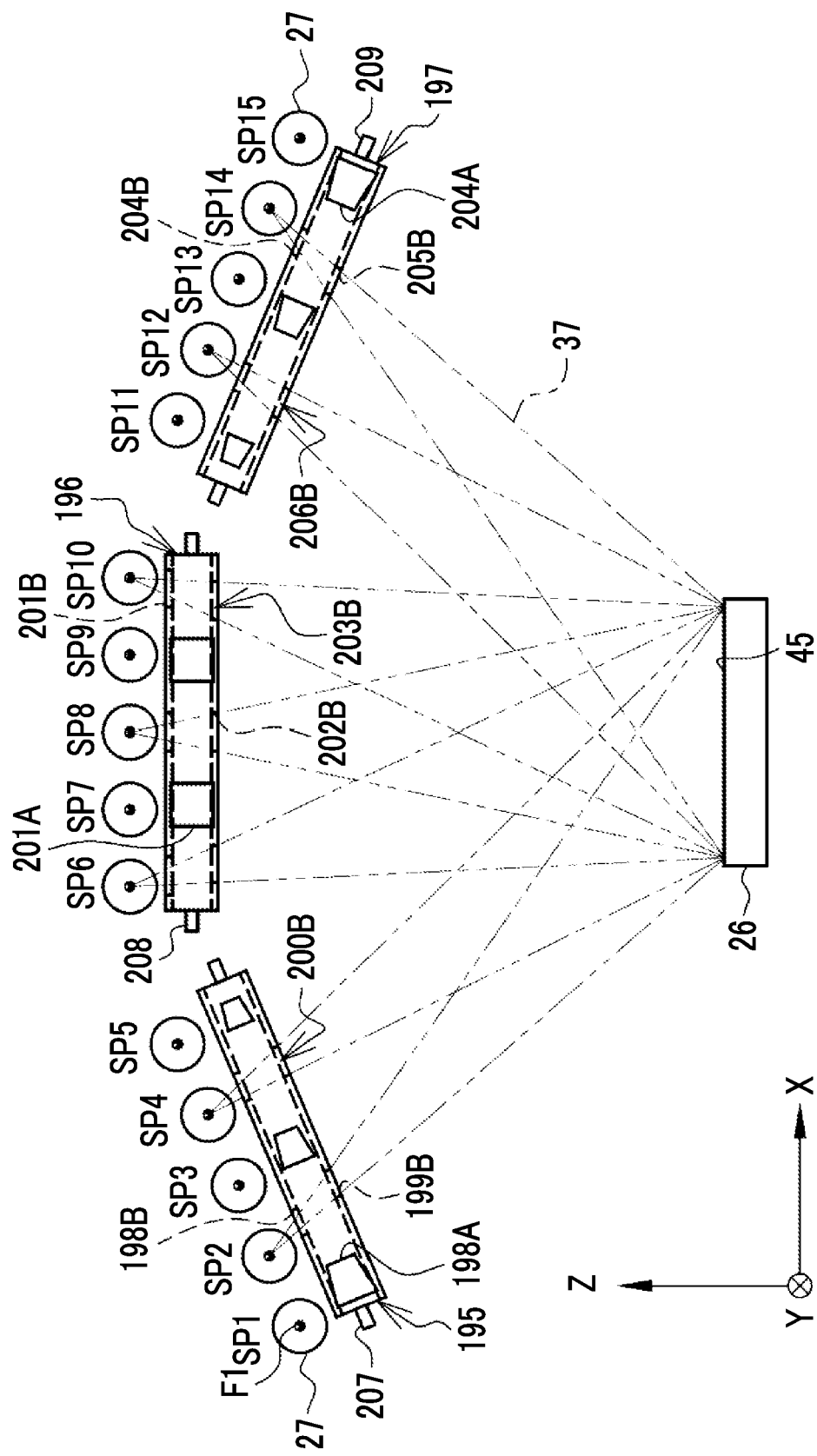
FIG. 45 is a diagram illustrating an example in which a plurality of radiation tubes are divided into a plurality of groups and the radiation tubes in the groups at the ends are disposed so as to be inclined at a predetermined angle with respect to the imaging surface.

As illustrated in FIGS. 44 and 45, the radiation tubes 27 may be divided into a first group of the radiation tubes 27 disposed at the positions SP1 to SP5, a second group of the radiation tubes 27 disposed at the positions SP6 to SP10, and a third group of the radiation tubes 27 disposed at the positions SP11 to SP15. The radiation tubes 27 in the first group and the third group may be arranged so as to be inclined at a predetermined angle with respect to the imaging surface 45.

In this case, it is preferable to prepare first rotating members 195 to 197 for each group. That is, the first rotating member 195 is prepared for the first group, the first rotating member 196 is prepared for the second group, and the first rotating member 197 is prepared for the third group. A first irradiation opening portion 200A configured by a pair of a first opening 198A and a second opening 199A and a first irradiation opening portion 200B configured by a pair of a first opening 198B and a second opening 199B are formed in the first rotating member 195. A first irradiation opening portion 203A configured by a pair of a first opening 201A and a second opening 202A and a first irradiation opening portion 203B configured by a pair of a first opening 201B and a second opening 202B are formed in the first rotating member 196. A first irradiation opening portion 206A configured by a pair of a first opening 204A and a second opening 205A and a first irradiation opening portion 206B configured by a pair of a first opening 204B and a second opening 205B are formed in the first rotating member 197.

A pair of rotating shafts 207 to 209 are attached to the centers of opposite side surfaces of the first rotating members 195 to 197, respectively. The first rotating members 195 to 197 are rotated about the rotating shafts 207 to 209 by the operation of motors (not illustrated) that are attached to the rotating shafts 207 to 209, respectively.

The first rotating members 195 to 197 are rotated to a first rotation position illustrated in FIG. 44 and a second rotation position illustrated in FIG. 45. As illustrated in FIG. 44, at the first rotation position, the first irradiation opening portions 200A, 203A, and 206A define the irradiation field of the radiation 37 emitted from the radiation tubes 27 disposed at the positions SP1, SP3, SP5, SP7, SP9, SP11, SP13, and SP15. In contrast, as illustrated in FIG. 45, at the second rotation position, the first irradiation opening portions 200B, 203B, and 206B define the irradiation field of the radiation 37 emitted from the radiation tubes 27 disposed at the positions SP2, SP4, SP6, SP8, SP10, SP12, and SP14. In this case, the adjacent first irradiation opening portions 200A, 203A, and 206A and the adjacent first irradiation opening portions 200B, 203B, and 206B are separated by an interval D_OP that is nearly equal to an interval of one radiation tube 27, which is not illustrated.

In the second group, a ratio SD1/SD2 of a distance SD1 between the radiation tube 27 and the first rotating member 196 to a distance SD2 between the first rotating member 196 and the imaging surface 45 is the same for all of the radiation tubes 27 forming the group. Further, the arrangement direction of the radiation tubes 27 is parallel to the direction of the long side of the first rotating member 196. Furthermore, the side of the imaging surface 45 in the X direction is parallel to the direction of the long side of the first rotating member 196. Therefore, the first openings 201A and 201B and the second openings 202A and 202B of the first rotating member 196 have the same size and the same rectangular shape. The distance SD1 is the length of a line connecting the focus F of the radiation tube 27 and the center of the second openings 202A and 202B facing each other. The distance SD2 is the length of a line connecting the centers of the second openings 202A and 202B and the center of the imaging surface 45.

In contrast, the first group is the same as the second group in that the arrangement direction of the radiation tubes 27 is parallel to the direction of the long side of the first rotating member 195. However, in the first group, the ratio SD1/SD2 varies depending on the radiation tubes 27 forming the group. Further, as described above, since the radiation tubes 27 are arranged so as to be inclined at a predetermined angle with respect to the imaging surface 45, the side of the imaging surface 45 in the X direction is not parallel to the direction of the long side of the first rotating member 195. Therefore, the first openings 198A and 198B and the second openings 199A and 199B of the first rotating member 195 have different sizes. Specifically, the sizes of the first openings 198A and 198B and the second openings 199A and 199B increase toward the end. Further, the first openings 198A and 198B and the second openings 199A and 199B have a trapezoidal shape in which the base is widened toward the end. Since the first rotating member 197 in the third group is mirror-symmetric to the first rotating member 195, the description thereof will be omitted.

As illustrated in FIGS. 46A and 46B, in the first group, the radiation tubes 27 may be disposed so as to become further away from the first rotating member 195 as becoming closer to the center such that the ratio SD1/SD2 is the same for all of the radiation tubes 27 forming the group. FIG. 46A illustrates the first rotation position and FIG. 46B illustrates the second rotation position. In this case, the first openings 198A and 198B and the second openings 199A and 199B have the same trapezoidal shape as in FIG. 45, but have the same size. In this case, in the third group, the radiation tubes 27 are disposed so as to become further away from the first rotating member 197 as becoming closer to the center such that the ratio SD1/SD2 is the same for all of the radiation tubes 27 forming the group, which is not illustrated.

As such, a plurality of radiation tubes 27 may be divided into a plurality of groups, each group may be regarded as one radiation source, and the first rotating members 195 to 197 may be arranged in each group.

Figure 47:
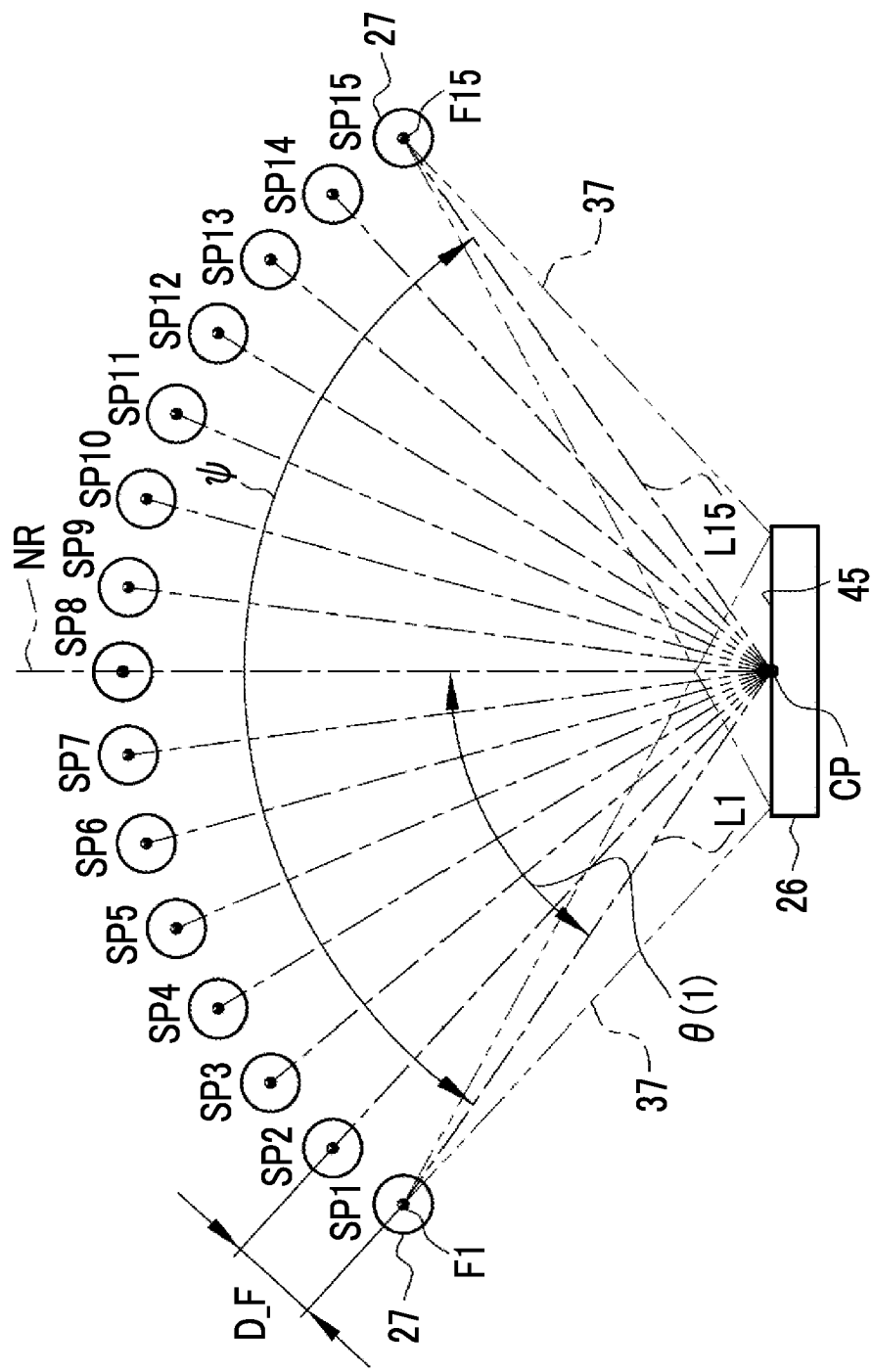
FIG. 47 is a diagram illustrating an example in which the radiation tubes are disposed at a plurality of positions where the focuses of radiation are set so as to be arranged in an arc shape at equal intervals.

In each of the above-described embodiments, the positions where the focuses F are disposed are arranged in a straight line. However, the present disclosure is not limited thereto. As illustrated in FIG. 47, the plurality of positions SP1 to SP15 where the focuses F1 to F15 are disposed may be arranged in an arc shape at equal intervals D_F. In this case, for example, a first rotating member 215 illustrated in FIG. 48 is used as the irradiation field limiter.

A first irradiation opening portion 218A configured by a pair of a first opening 216A and a second opening 217A and a first irradiation opening portion 218B configured by a pair of a first opening 216B and a second opening 217B are formed in the first rotating member 215. The first rotating member 215 is rotated about a rotating shaft 219 by the operation of a motor (not illustrated) that is attached to the rotating shaft 219. In this case, the ratio SD1/SD2 varies depending on the radiation tube 27. However, the side of the imaging surface 45 in the X-direction is parallel to the direction of the long side of the first rotating member 215. Therefore, the sizes of the first openings 216A and 216B and the second openings 217A and 217B decrease toward the end. Further, the first openings 216A and 216B and the second openings 217A and 217B have the same rectangular shape.

Figure 48:
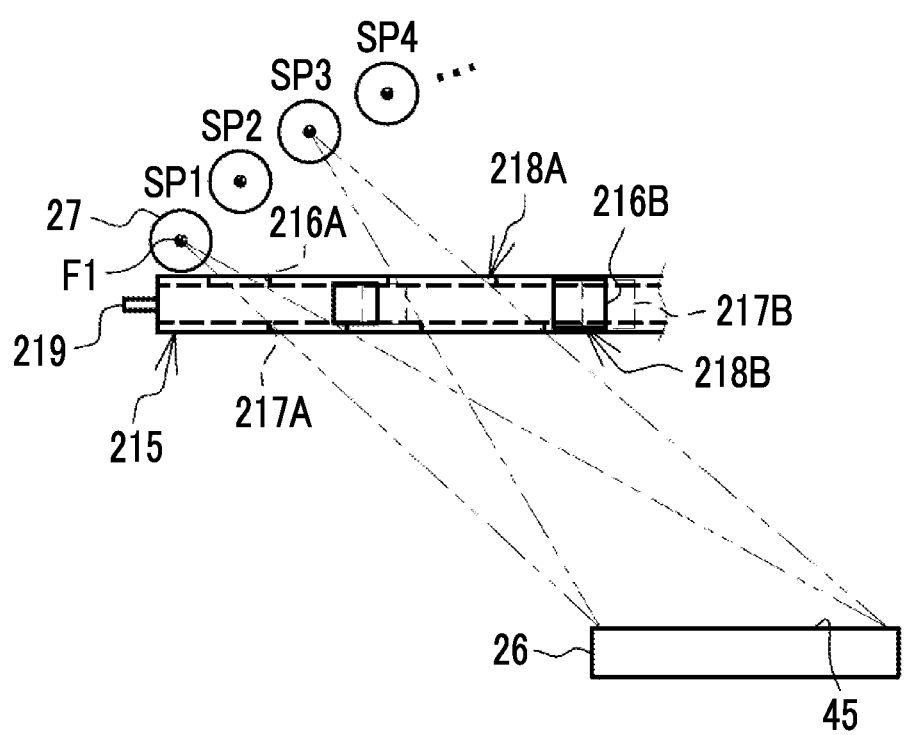
FIG. 48 is a diagram illustrating the sizes and shapes of the first opening and the second opening of the first rotating member in the example illustrated in FIG. 47.
Figure 49:
FIG. 49 is a table summarizing the sizes and shapes of the first opening and the second opening in the aspects illustrated in FIGS. 44 to 48.

FIG. 49 is a table 220 summarizing the sizes and shapes of the first and second openings in the aspects illustrated in FIGS. 44 to 48. Patterns 1 to 3 indicate cases in which the radiation tubes 27 are arranged in a linear shape and pattern 4 indicates a case in which the radiation tubes 27 are arranged in an arc shape. Pattern 1 indicates an aspect of the first rotating member 196 illustrated in FIGS. 44 and 45. In this case, the first openings 201A and 201B and the second openings 202A and 202B have the same size and have the same rectangular shape. Pattern 2 indicates an aspect of the first rotating members 195 and 197 illustrated in FIGS. 44 and 45. In this case, the first openings 198A, 198B, 204A, 204B, and the second openings 199A, 199B, 205A, and 205B have different sizes, but have the same trapezoidal shape. Pattern 3 indicates an aspect of the first rotating member 195 illustrated in FIGS. 46A and 46B. In this case, the first openings 198A and 198B and the second openings 199A and 199B have the same size and have the same trapezoidal shape.

Pattern 4 indicates an aspect of the first rotating member 215 illustrated in FIG. 48. In this case, the first openings 216A and 216B and the second openings 217A and 217B have different sizes, but have the same rectangular shape.

Instead of the simple imaging in which the CC imaging illustrated in FIG. 5 and the MLO imaging illustrated in FIG. 6 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images P obtained by the tomosynthesis imaging or a plurality of tomographic images T generated by the generation unit 83.

In each of the above-described embodiments, the mammography apparatus 10 has been exemplified. In the related art, performing tomosynthesis imaging in the mammography apparatus 10 has been found to be useful as a method for easily finding lesions such as microcalcifications of the breast M. Therefore, it is preferable to apply the technique of the present disclosure to the mammography apparatus 10.

Figure 50:
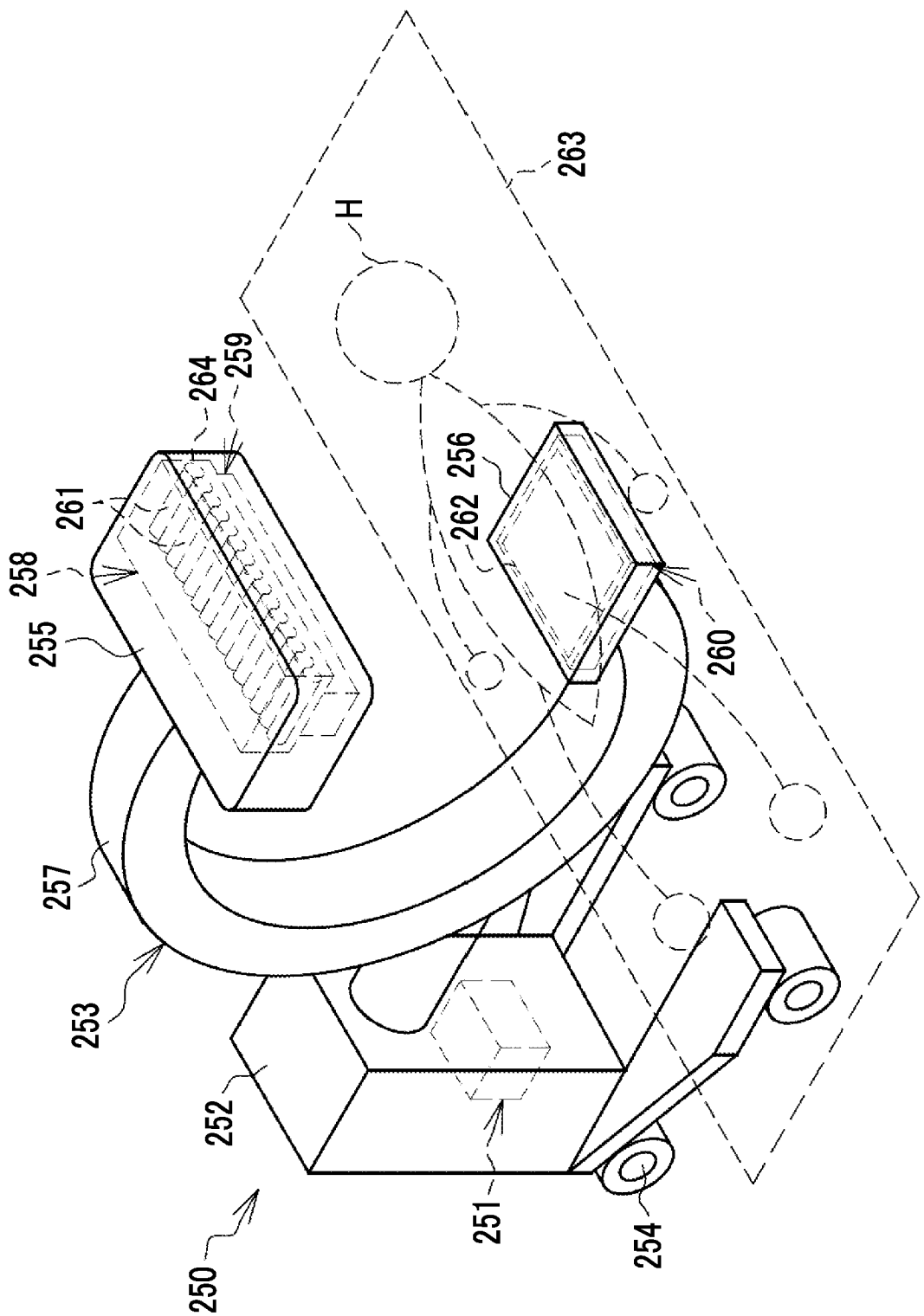
FIG. 50 is a diagram illustrating an imaging apparatus for surgery.

Of course, the technology of the present disclosure is not limited to the mammography apparatus 10 and may be applied to other imaging apparatuses. For example, the technology of the present disclosure may be applied to an imaging apparatus 250 illustrated in FIG. 50 which captures the image of the subject H during surgery.

The imaging apparatus 250 comprises an apparatus main body 252 having a control device 251 provided therein and an arm 253 having a substantially C-shape in a side view. A carriage 254 is attached to the apparatus main body 252 such that the apparatus main body 252 can be moved. The arm 253 includes a radiation source accommodation portion 255, a detector accommodation portion 256, and a main body portion 257. As in the mammography apparatus 10 illustrated in FIG. 1, the radiation source accommodation portion 255 accommodates a radiation source 258 and an irradiation field limiter 259. In addition, the detector accommodation portion 256 accommodates a radiation detector 260. The radiation source accommodation portion 255 and the detector accommodation portion 256 are held by the main body portion 257 at a posture where they face each other.

The radiation source 258 and the radiation detector 260 have the same basic configurations as the radiation source 25 and the radiation detector 26 illustrated in FIG. 1, respectively. However, the imaging apparatus 250 captures an image of an object, such as the entire chest of the subject H, which is larger than the breast M. Therefore, a radiation tube 261 forming the radiation source 258 has a larger diameter than each radiation tube 27 of the mammography apparatus 10. In addition, the radiation detector 260 has an imaging surface 262 whose area is larger than that of the imaging surface 45 of the radiation detector 26. The number of radiation tubes 261 arranged may increase in order to correspond to the capture of the image of a large object.

The detector accommodation portion 256 is inserted below a bed 263 on which the subject H lies supine. The bed 263 is made of a material that transmits the radiation 37. The radiation source accommodation portion 255 is provided above the subject H at a position that faces the detector accommodation portion 256 with the subject H interposed therebetween.

The irradiation field limiter 259 of the imaging apparatus 250 includes a first rotating member, like the irradiation field limiter 29 of the mammography apparatus 10. The imaging apparatus 250 can perform simple imaging using one radiation tube 261, in addition to the tomosynthesis imaging. In addition, instead of the simple imaging, the imaging apparatus may generate a composite radiographic image. Further, the imaging apparatus 250 may capture both still radiographic images and moving radiographic images. Furthermore, reference numeral 264 indicates a housing for the radiation source 258.

The technology of the present disclosure may be applied to a general radiography apparatus configured by combining a ceiling-suspended radiation source and an upright imaging table or a decubitus imaging table in which a radiation detector is set, in addition to the imaging apparatus 250 for surgery. Further, the technology of the present disclosure may be applied to, for example, a cart-type mobile radiography apparatus which is moved to each hospital room and is used to capture the image of the subject H.

In each of the above-described embodiments, the example in which the irradiation field is defined by the first opening or the second opening has been described. However, the irradiation field may be defined by both the first opening and the second opening. Further, in each of the above-described embodiments, the radiation tube 27 having one focal point F is given as an example. However, the technology of the present disclosure is not limited thereto. A radiation tube having a plurality of focuses F may be used.

In the technology of the present disclosure, the above-described various embodiments and/or various modification examples may be combined with each other. In addition, the present disclosure is not limited to the above-described embodiments and various configurations can be used without departing from the scope and spirit of the present disclosure.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the scope and spirit of the technology of the present disclosure. In addition, in the above-described content and the above-illustrated content, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A tomosynthesis imaging apparatus comprising:
   a radiation source in which three or more radiation tubes emitting radiation are arranged to perform tomosynthesis imaging which irradiates an object with the radiation at a plurality of different irradiation angles; and
   an irradiation field limiter having a plurality of first irradiation opening portions which are provided along a direction of a straight line connecting focuses of the radiation tubes at both ends where the radiation is emitted and each of which is configured by a pair of a first opening and a second opening facing each other in an irradiation direction of the radiation and defines an irradiation field of the radiation,
   wherein the irradiation field limiter includes a first rotating member that is rotated to a plurality of rotation positions including at least a first rotation position and a second rotation position about a rotating shaft that is parallel to the direction of the straight line,
   at the rotation positions, two or more of the first irradiation opening portions which are arranged at an interval of at least one radiation tube face the radiation tubes in the irradiation direction,
   the first irradiation opening portions deviate from each other in the direction of the straight line, and
   among the three or more radiation tubes, at least some of second radiation tubes, which are other than first radiation tubes facing the first irradiation opening portions at the first rotation position and do not face the first irradiation opening portions, face the first irradiation opening portions at the second rotation position.

2. The tomosynthesis imaging apparatus according to claim 1,
   wherein the irradiation field is defined by the first opening or the second opening.

3. The tomosynthesis imaging apparatus according to claim 1,
   wherein a plurality of the first rotating members are arranged along the direction of the straight line and are independently rotated.

4. The tomosynthesis imaging apparatus according to claim 1,
   wherein the first rotating member has a regular N-gonal shape in a cross-sectional view taken along a lateral direction, and
   N is an even number that is equal to or greater than 4.

5. The tomosynthesis imaging apparatus according to claim 4,
   wherein the rotation positions are positions corresponding to 360°/N.

6. The tomosynthesis imaging apparatus according to claim 1,
   wherein the first rotating member has a circular shape in a cross-sectional view taken along a lateral direction.

7. The tomosynthesis imaging apparatus according to claim 1,
   wherein the first opening and the second opening have different sizes.

8. The tomosynthesis imaging apparatus according to claim 1,
   wherein the first rotating member is hollow.

9. The tomosynthesis imaging apparatus according to claim 8,
   wherein the irradiation field limiter has a configuration in which a second rotating member that is rotated about a rotating shaft parallel to the direction of the straight line independently of the first rotating member and has a second irradiation opening portion with a size different from that of the first irradiation opening portion is provided in the first rotating member.

10. The tomosynthesis imaging apparatus according to claim 8, wherein the irradiation field limiter has a configuration in which a visible light emitting unit that emits visible light indicating the irradiation field is provided in the first rotating member.

11. The tomosynthesis imaging apparatus according to claim 1,
wherein the rotating shaft of the first rotating member is offset from centers of the first and second openings in a plan view from the direction of the straight line.

12. The tomosynthesis imaging apparatus according to claim 1,
wherein the plurality of radiation tubes are arranged at equal intervals in a linear shape or an arc shape.

* * * * *

UNITED STATES PATENT AND TRADEMARK OFFICE
CERTIFICATE OF CORRECTION

| | |
|---|---|
| PATENT NO. | : 11,219,417 B2 |
| APPLICATION NO. | : 16/988860 |
| DATED | : January 11, 2022 |
| INVENTOR(S) | : Shinichiro Konno et al. |

It is certified that error appears in the above-identified patent and that said Letters Patent is hereby corrected as shown below:

On the Title Page

Foreign Application Priority Data (30) should be added:
(30) Foreign Application Priority Data
Sep. 6, 2019 (JP) .......................JP2019-162950

Signed and Sealed this
Third Day of May, 2022

Katherine Kelly Vidal
*Director of the United States Patent and Trademark Office*